US010761098B2

(12) United States Patent
Storry et al.

(10) Patent No.: US 10,761,098 B2
(45) Date of Patent: Sep. 1, 2020

(54) METHODS AND TOOLS FOR VEL BLOOD GROUP TYPING

(71) Applicant: LU License AB, Lund (SE)

(72) Inventors: Jill R. Storry, Bjärred (SE); Magnus Jöud, Hjärup (SE); Björn Nilsson, Lund (SE); Martin L. Olsson, Bjärred (SE)

(73) Assignee: LU License AB, Lund (SE)

( * ) Notice: Subject to any disclaimer, the term of this patent is extended or adjusted under 35 U.S.C. 154(b) by 36 days.

(21) Appl. No.: 15/949,200

(22) Filed: Apr. 10, 2018

(65) Prior Publication Data

US 2018/0299465 A1 Oct. 18, 2018

Related U.S. Application Data

(62) Division of application No. 14/431,424, filed as application No. PCT/EP2013/070403 on Oct. 1, 2013, now Pat. No. 9,989,537.

(Continued)

(30) Foreign Application Priority Data

Oct. 1, 2012 (SE) ...................................... 1251099

(51) Int. Cl.

| | |
|---|---|
| ***G01N 33/68*** | (2006.01) |
| ***G01N 33/80*** | (2006.01) |
| ***C07K 16/34*** | (2006.01) |
| ***C12N 15/113*** | (2010.01) |
| ***C12Q 1/6827*** | (2018.01) |
| ***C12Q 1/6881*** | (2018.01) |
| ***A61K 35/18*** | (2015.01) |
| ***C07K 7/08*** | (2006.01) |
| ***C07K 14/00*** | (2006.01) |

(52) U.S. Cl.

CPC ......... *G01N 33/6854* (2013.01); *A61K 35/18* (2013.01); *C07K 7/08* (2013.01); *C07K 14/00* (2013.01); *C07K 16/34* (2013.01); *C12N 15/1138* (2013.01); *C12Q 1/6827* (2013.01); *C12Q 1/6881* (2013.01); *G01N 33/80* (2013.01); *C07K 2317/34* (2013.01); *C12N 2310/14* (2013.01); *C12N 2310/531* (2013.01); *C12Q 2600/106* (2013.01); *C12Q 2600/156* (2013.01)

(58) Field of Classification Search

CPC ............ C12Q 1/6881; C12Q 2600/106; C12Q 1/6827; C12N 15/1138; C12N 2310/14; C12N 2310/531; C12N 2310/05; G01N 33/6854; C07K 16/34; C07K 2317/34; C07K 7/08; C07K 14/00; A61K 35/18

See application file for complete search history.

(56) References Cited

U.S. PATENT DOCUMENTS

| | | | | |
|---|---|---|---|---|
| 8,198,027 | B2 | 6/2012 | Brentano et al. | |
| 2009/0181380 | A1* | 7/2009 | Belouchi ............. | C12Q 1/6883 435/6.11 |

OTHER PUBLICATIONS

Issitt et al., (Vox Sang. 15: 125-132 (1968). (Year: 1968).*

(Continued)

*Primary Examiner* — Jana A Hines

(74) *Attorney, Agent, or Firm* — Suzannah K. Sundby, Esq.; Canady + Lortz LLP

(57) ABSTRACT

The present invention relates to methods and tools for discriminating between Vel negative and Vel positive phenotypes. The invention is thus useful for determining Vel blood group status of individuals about to receive blood transfusion.

16 Claims, 11 Drawing Sheets

Specification includes a Sequence Listing.

Related U.S. Application Data

(60) Provisional application No. 61/731,556, filed on Nov. 30, 2012.

(56) References Cited

OTHER PUBLICATIONS

Csorba, et al., "Development of an ELISA for sensitive and specific detection of IgA autoantibodies against BP180 in pemphigoid disease", May 28, 2011, pp. 1-10, vol. 6, No. 31, Publisher: Orphanet Journal of Rare Diseases.
Avent et al. 2007 "The BloodGen project: toward mass-scale comprehensive genotyping of blood donors in the European Union and beyond" TRANSFUSION vol. 47, Supplement. pp. 40S-46S.
Edvardsson et al. 2004 "Clonogenicity, gene expression and phenotype during neutrophil versus erythroid differentiation of cytokinestimulated CD34+ human marrow cells in vitro" British Journal of Haematology, 127, 451-463.
EM_EST:AI078360, Aug. 11, 1998, XP055089388.
EM_EST:AW593551, Mar. 23, 2000, XP055089389.
EM_EST:HY032469, May 20, 2012, XP055089382.
EM_GSS:DQ045780, Jun. 3, 2005, XP055089381.
EM_GSS:DQ045780, Jun. 3, 2005, XP055089384.
EM_STD:BC146945, May 13, 2008, XP055089484.
Gassner et al. 2013 "Matrix-Assisted Laser Desorption/lonisation, Time-of-Flight Mass Spectrometry-Based Blood Group Genotyping—The Alternative Approach" Transfusion Medicine Reviews 27, 2-9.
Gene: Expression Probeset for SMIM1 on affymetrix HG-U133_PLUS_2, Jan. 1, 2005, XP55089356.
Gregory et al. 2006 "The DNA sequence and biological annotation of human chromosome 1" Nature, vol. 441, No. 7901, 315-321.
GSN:A0H52488, Feb. 3, 2011, XP055089482.
GSN:AFS84630, Sep. 2, 2007, XP055089516.
GSN:AGH67528, Oct. 18, 2007, XP055089385.
Issitt et al. 1968 "Anti-Vel 2, a New Antibody Showing Heterogeneity of Vel System Antibodies" Vox Sang. 15:125-132.
Kasamatsu et al. 2005 "Identification of candidate genes associated with salivary adenoid cystic carcinomas using combined comparative genomic hybrydization and oligonucleotide microarray analyses" International Journal of Biochemistry and Cell Biology, vol. 37, No. 9, 1869-1880.
Miller et al. 1988 "A simple salting out procedure for extracting DNA from human nucleated cells" Nucleic Acids Research, vol. 16 No. 3.
Sandler et al. 1979 "Autologous blood transfusions and pregnancy" Obstetrics & Gynecology, vol. 53, No. 3 Suppl., 62S-66S.
SMIM_1 UniProt B2RUZ4, belongs to XP002498948, Jan. 1, 2006.
Storry and Mallory, 1994 "Misidentification of anti-Vel due to inappropriate use of prewarming and adsorption techniques" Immunohematology, vol. 10, No. 3, 83-86.
Storry et al. 2011 "International Society of Blood Transfusion Working Party on red cell immunogenetics and blood group terminology: Berlin report" Vox Sanguinis, 101, 77-82.
Storry et al. 2013 "Homozygosity for a null allele of SMIM1 defines the Vel-negative blood group phenotype" Nature Genetics, vol. 45, No. 5, 537-541.
Wester et al. 2011 "Characterization of Jk(a+weak): a new blood group phenotype associated with an altered JK*01 allele" TRANSFUSION vol. 51, pp. 380-392.

* cited by examiner

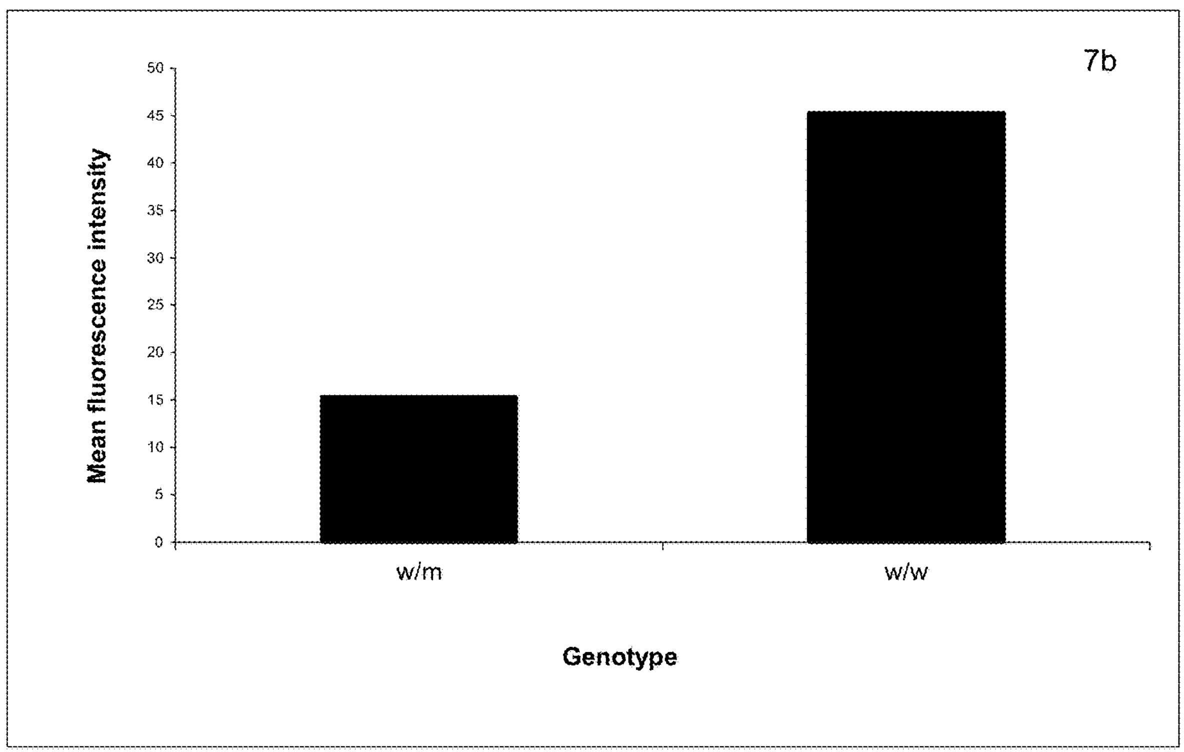
Fig. 7, cont

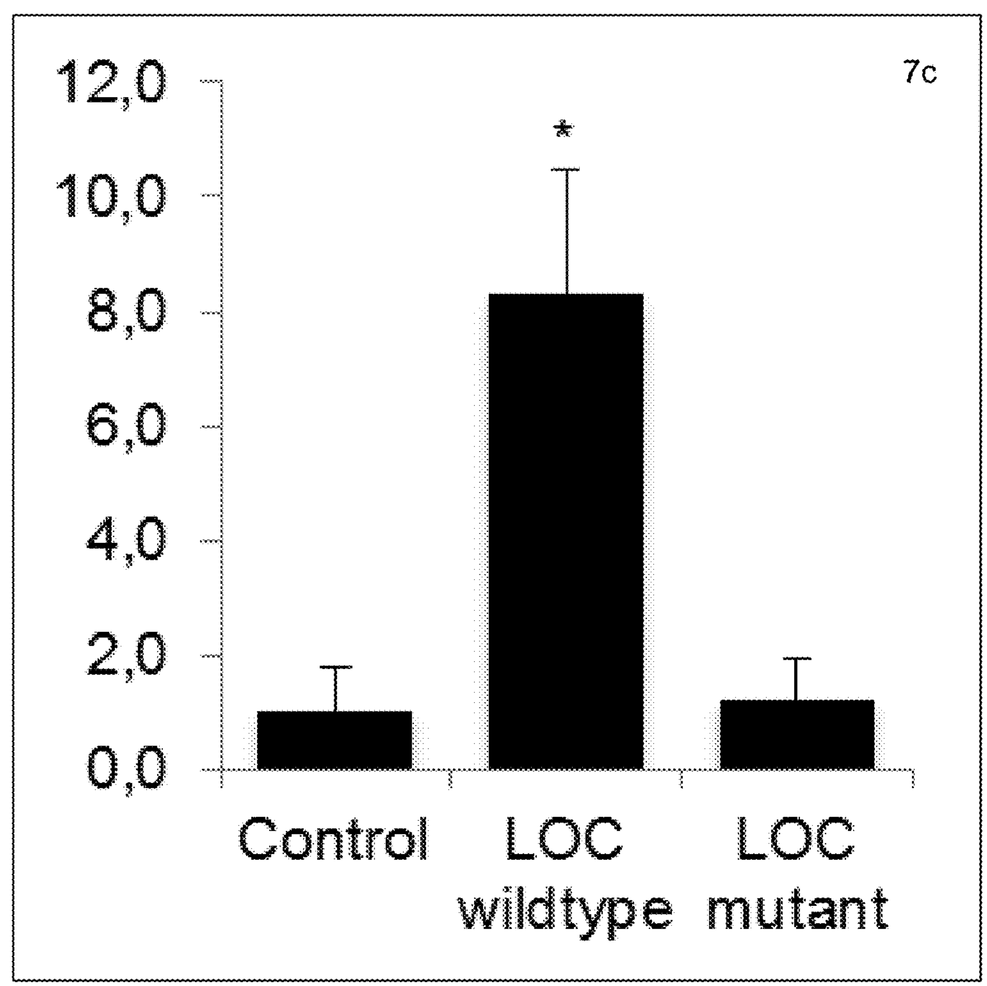
Fig. 7, cont.

SEQUENCE LISTING

```
<160> NUMBER OF SEQ ID NOS: 36

<210> SEQ ID NO 1
<211> LENGTH: 3187
<212> TYPE: DNA
<213> ORGANISM: Homo sapiens

<400> SEQUENCE: 1

cagagacgcg gggacacagg tgaggcgcgc ggggtccggg ctgcggcttc ccggtgcggc      60

cgcagtgggc aggtgcgact gtgcgcggcc tcgctggctg agaactggcg ggggtggggg     120

cgtgccctgg actgaccccc accggcctaa cccgcggtgc ggggccaggg ccggaactgc     180

ccgcccggct ccttgcccgg ctccttgtgg ctgctgggga cccccgacac cagccacttt     240

cccttcccgg cccttagcaa gatcggcttc tccggtcacc tttatttttt taggctcgag     300

gcgtctgccg cacctcagcc cacgacctgc cccgctggga ggtgcgggcc gctggccagg     360
```

```
ccctgaccgc aacctggccc agaggcccca gccctcaggc aaggttctcc gggtaagtgt    420
ggggccctga ggcgctgtgg ggtgaagagg tctatggagg ggcgcctgtg tacctagggc    480
cttcctgcac tcacaagccc ccaggaggtg ccaggatccg ggagcctccc agggcctgga    540
ggggagtccc tgatgggttc ctgccgccac acctgtgacc atcacatgag tgtggagaga    600
cgtttactga gcaagtgagg gaggccagcc tcaagggccg gctctggtgg ctgtgcaccg    660
gggtgacttg ggaacaacgt gttctacgtc agcaagacag gaacccatga tcccagagtt    720
gaacacactg ggcttgaccc ctcccaccgg gaggcccatg gtgggctgct gctgtggact    780
tggagcctca gcactcccga gactaatgct gcgtggatgt cgggttgcaa ggcggctgct    840
gcagctccag cagctccagc catcacgtcg agtctggaag aaggaggtgg ctgctgctgc    900
tttcacagaa gcaaactctc ccatcccctg ctgcaccctg gctcctggac cccagctggg    960
tgacttggga aagcaggggt ggtggtatta agcttgtctt acccgggtca tggctgttac   1020
ctggggctgg cacattgctg ctgggaccag aatgggattc tgcacaccag gcaagagggc   1080
gtgaacctcg ggtaggcagc tgaccgctcc acatgctccg ggaaaacagc acccatactc   1140
cagtagaggc tgggcctctc cggcctgag tgccaggctg cactgagcca gggctcccac   1200
cgaaggcaca ctttatggct ttgagacagc tccttctgcc tctctgggct ttgggggaag   1260
gcagacatgg aagtgccggg agtctcagaa ctgcctgggg cctgagtttc tgagctggct   1320
tcttgcaggg gagtggctgc tgtgccttta ggcctctgtg ccgatgacct gggaggaagg   1380
tcagccttcc ccgctggagg gggcccagca aagcctcagc tcctagaagt gaggggcctg   1440
ccattgcctg cccgaggacc ccactcctgg gggccagatg ctgagagggg acactggggg   1500
cccagcagac cagagagctg accccagtcc cacagcctgg gtgggttgtc aacttctcgt   1560
gccccctcca actcctccac ccccacaccc ccttaggtaa ataggaggtc gaaacagagg   1620
ccagagggta aaggaggtgc ttagagtccg ggctggctca ggccggccgg gcagctgtgc   1680
tagtgcttgg agttcctgct cagtccccgt ggtctcctcg cccctctggg cacttgggct   1740
gccaggcacc gagctgagtg ccgagatgca aagatgagtc ccaggtctgc aggagttgga   1800
gcccagcagg gagctggcct tggggccggg cccctcctgc tctgggcagc cacccagccc   1860
tacgaccctc ctgtctctgt agggcctccc caaggccttg aatccacccc ggccccgtgc   1920
tcagtgcatc atgcccccca agccccagcc ctcctagagg tgtgggtggg ggaggggctg   1980
caacccacac aggctgagga cacagctgct gccactgcct ggggccagcc acgcatcctc   2040
cccagacagg gaccggtcta gctgtaccag ccgctgcccc ggacctgctg ccctgcccca   2100
cccccccctc ccctggccag cctccccaga ggccagaagg cgccttatcg ggcagggtta   2160
aggaggggga cagttatcag ggctgcagc ctagattggg ccacaatgtc ctcgtctctt   2220
gagggtggca ggctgtgcag gctccctgat aaaagcaccg gggaagggag gctcctggag   2280
tgtgctggaa ggaaacactg gcctcccaca tgcctgaggt cagggcttgg cctgagatgg   2340
aattctcgct tggtcccatc ctcccggcct gaccctgggc aaatgactct accactttgt   2400
gtctaggtca cctgttaagt caggcgacag acccggtgag ggagtcagcc cccgaccctt   2460
agtgcccctc tcctaacagc agcctcagag ggggtcttga ctgccgccct ccatccgctt   2520
gttttacagt gaagccacag cctggccacc tgtcttgatc tccccaccga gaaggccccg   2580
cccctcccgc tgcagcccca cagcatgcag ccccaggaga gccacgtcca ctatagtagg   2640
tgggaggacg gcagcaggga cggagtcagc ctaggggctg tgtccagcac agaagaggcc   2700
```

```
tcacgctgcc gcaggtgagg ggcctgaggg cagcctgcca gccatagcag gctggtgtct   2760

ccctccagag acgcctgccc taacccctgc taccggcccc atcaccctcc accccatcct   2820

ggctgggagc ccacggtcca gcagctcagc aaaccgcagc ctttggcctt ccctctggtt   2880

ggctgtgggc ggggagagct tcctcttgac tccagcagag cgcccaggcc cctccccctg   2940

acccagacca acggccacag tccacttagg gggcccctca tgcggccctg gcctggggct   3000

cacctccagt tggttctcac cccaggatct cccagaggct gtgcacgggc aagctgggca   3060

tcgccatgaa ggtgctgggc ggcgtggccc tcttctggat catcttcatc ctgggctacc   3120

tcacaggcta ctatgtgcac aagtgcaaat aaatgctgcc ccgcatgcac gcggggggct   3180

ggccgca                                                             3187
```

<210> SEQ ID NO 2
<211> LENGTH: 3170
<212> TYPE: DNA
<213> ORGANISM: Homo sapiens

<400> SEQUENCE: 2

```
cagagacgcg gggacacagg tgaggcgcgc ggggtccggg ctgcggcttc ccggtgcggc     60

cgcagtgggc aggtgcgact gtgcgcggcc tcgctggctg agaactggcg ggggtggggg    120

cgtgccctgg actgaccccc accggcctaa cccgcggtgc ggggccaggg ccggaactgc    180

ccgcccggct ccttgcccgg ctccttgtgg ctgctgggga cccccgacac cagccacttt    240

cccttcccgg cccttagcaa gatcggcttc tccggtcacc tttatttttt taggctcgag    300

gcgtctgccg cacctcagcc cacgacctgc cccgctggga ggtgcgggcc gctggccagg    360

ccctgaccgc aacctggccc agaggcccca gccctcaggc aaggttctcc gggtaagtgt    420

ggggccctga ggcgctgtgg ggtgaagagg tctatggagg ggcgcctgtg tacctagggc    480

cttcctgcac tcacaagccc ccaggaggtg ccaggatccg ggagcctccc agggcctgga    540

ggggagtccc tgatgggttc ctgccgccac acctgtgacc atcacatgag tgtggagaga    600

cgtttactga gcaagtgagg gaggccagcc tcaagggccg gctctggtgg ctgtgcaccg    660

gggtgacttg ggaacaacgt gttctacgtc agcaagacag gaacccatga tcccagagtt    720

gaacacactg ggcttgaccc ctcccaccgg gaggcccatg gtgggctgct gctgtggact    780

tggagcctca gcactcccga gactaatgct gcgtggatgt cgggttgcaa ggcggctgct    840

gcagctccag cagctccagc catcacgtcg agtctggaag aaggaggtgg ctgctgctgc    900

tttcacagaa gcaaactctc ccatcccctg ctgcaccctg gctcctggac cccagctggg    960

tgacttggga aagcaggggt ggtggtatta agcttgtctt acccgggtca tggctgttac   1020

ctggggctgg cacattgctg ctgggaccag aatgggattc tgcacaccag gcaagagggc   1080

gtgaacctcg ggtaggcagc tgaccgctcc acatgctccg ggaaaacagc acccatactc   1140

cagtagaggc tgggcctctc cgggcctgag tgccaggctg cactgagcca gggctcccac   1200

cgaaggcaca ctttatggct ttgagacagc tccttctgcc tctctgggct ttgggggaag   1260

gcagacatgg aagtgccggg agtctcagaa ctgcctgggg cctgagtttc tgagctggct   1320

tcttgcaggg gagtggctgc tgtgccttta ggcctctgtg ccgatgacct gggaggaagg   1380

tcagccttcc ccgctggagg gggcccagca aagcctcagc tcctagaagt gaggggcctg   1440

ccattgcctg cccgaggacc ccactcctgg gggccagatg ctgagagggg acactggggg   1500

cccagcagac cagagagctg accccagtcc cacagcctgg gtgggttgtc aacttctcgt   1560

gccccctcca actcctccac ccccacaccc ccttaggtaa ataggaggtc gaaacagagg   1620
```

```
ccagagggta aaggaggtgc ttagagtccg ggctggctca ggccggccgg gcagctgtgc   1680
tagtgcttgg agttcctgct cagtccccgt ggtctcctcg cccctctggg cacttgggct   1740
gccaggcacc gagctgagtg ccgagatgca aagatgagtc ccaggtctgc aggagttgga   1800
gcccagcagg gagctggcct tggggccggg cccctcctgc tctgggcagc cacccagccc   1860
tacgaccctc ctgtctctgt agggcctccc caaggccttg aatccacccc ggccccgtgc   1920
tcagtgcatc atgcccccca agccccagcc ctcctagagg tgtgggtggg ggaggggctg   1980
caacccacac aggctgagga cacagctgct gccactgcct ggggccagcc acgcatcctc   2040
cccagacagg gaccggtcta gctgtaccag ccgctgcccc ggacctgctg ccctgcccca   2100
cccccccctc ccctggccag cctccccaga ggccagaagg cgccttatcg ggcagggtta   2160
aggaggggga cagttatcag gggctgcagc ctagattggg ccacaatgtc ctcgtctctt   2220
gagggtggca ggctgtgcag gctccctgat aaaagcaccg gggaagggag gctcctggag   2280
tgtgctggaa ggaaacactg gcctcccaca tgcctgaggt cagggcttgg cctgagatgg   2340
aattctcgct tggtcccatc ctcccggcct gaccctgggc aaatgactct accactttgt   2400
gtctaggtca cctgttaagt caggcgacag acccggtgag ggagtcagcc cccgaccctt   2460
agtgcccctc tcctaacagc agcctcagag ggggtcttga ctgccgccct ccatccgctt   2520
gttttacagt gaagccacag cctggccacc tgtcttgatc tccccaccga gaaggccccg   2580
cccctcccgc tgcagcccca cagcatgcag ccccaggaga gccacgtcca ctatagtagg   2640
tgggaggacg gcagcaggga cggagtccag cacagaagag gcctcacgct gccgcaggtg   2700
aggggcctga gggcagcctg ccagccatag caggctggtg tctccctcca gagacgcctg   2760
ccctaacccc tgctaccggc cccatcaccc tccaccccat cctggctggg agcccacggt   2820
ccagcagctc agcaaaccgc agcctttggc cttccctctg gttggctgtg ggcggggaga   2880
gcttcctctc aactccagca gagcgcccag gcccctcccc ctgacccaga ccaacggcca   2940
cagtccactt agggggcccc tcatgcggcc ctggcctggg gctcacctcc agttggttct   3000
caccccagga tctcccagag gctgtgcacg ggcaagctgg gcatcgccat gaaggtgctg   3060
ggcggcgtgg ccctcttctg gatcatcttc atcctgggct acctcacagg ctactatgtg   3120
cacaagtgca aataaatgct gccccgcatg cacgcggggg gctggccgca              3170
```

<210> SEQ ID NO 3
<211> LENGTH: 530
<212> TYPE: DNA
<213> ORGANISM: Homo sapiens

<400> SEQUENCE: 3

```
ggtgaggcgc gcggggtccg ggctgcggct tcccggtgcg gccgcagtgg gcaggctcga     60
ggcgtctgcc gcacctcagc ccacgacctg ccccgctggg aggtgcgggc cgctggccag    120
gccctgaccg caacctggcc cagaggcccc agccctcagg caaggttctc cggtgaagcc    180
acagcctggc cacctgtctt gatctcccca ccgagaaggc cccgcccctc ccgctgcagc    240
cccacagcat gcagccccag gagagccacg tccactatag taggtgggag gacggcagca    300
gggacggagt cagcctaggg gctgtgtcca gcacagaaga ggcctcacgc tgccgcagga    360
tctcccagag gctgtgcacg ggcaagctgg gcatcgccat gaaggtgctg ggcggcgtgg    420
ccctcttctg gatcatcttc atcctgggct acctcacagg ctactatgtg cacaagtgca    480
aataaatgct gccccgcatg cacgcggggg gctggccgca aaaaaaaaaa               530
```

<210> SEQ ID NO 4
<211> LENGTH: 513
<212> TYPE: DNA
<213> ORGANISM: Homo sapiens

<400> SEQUENCE: 4

```
ggtgaggcgc gcggggtccg ggctgcggct tcccggtgcg gccgcagtgg gcaggctcga     60

ggcgtctgcc gcacctcagc ccacgacctg ccccgctggg aggtgcgggc cgctggccag    120

gccctgaccg caacctggcc cagaggcccc agccctcagg caaggttctc cggtgaagcc    180

acagcctggc cacctgtctt gatctcccca ccgagaaggc cccgcccctc ccgctgcagc    240

cccacagcat gcagccccag gagagccacg tccactatag taggtgggag gacggcagca    300

gggacggagt ccagcacaga agaggcctca cgctgccgca ggatctccca gaggctgtgc    360

acgggcaagc tgggcatcgc catgaaggtg ctgggcggcg tggccctctt ctggatcatc    420

ttcatcctgg gctacctcac aggctactat gtgcacaagt gcaaataaat gctgccccgc    480

atgcacgcgg ggggctggcc gcaaaaaaaa aaa                                 513
```

<210> SEQ ID NO 5
<211> LENGTH: 78
<212> TYPE: PRT
<213> ORGANISM: Homo sapiens

<400> SEQUENCE: 5

```
Met Gln Pro Gln Glu Ser His Val His Tyr Ser Arg Trp Glu Asp Gly
1               5                   10                  15

Ser Arg Asp Gly Val Ser Leu Gly Ala Val Ser Ser Thr Glu Glu Ala
            20                  25                  30

Ser Arg Cys Arg Arg Ile Ser Gln Arg Leu Cys Thr Gly Lys Leu Gly
        35                  40                  45

Ile Ala Met Lys Val Leu Gly Gly Val Ala Leu Phe Trp Ile Ile Phe
    50                  55                  60

Ile Leu Gly Tyr Leu Thr Gly Tyr Tyr Val His Lys Cys Lys
65                  70                  75
```

<210> SEQ ID NO 6
<211> LENGTH: 15
<212> TYPE: PRT
<213> ORGANISM: Homo sapiens

<400> SEQUENCE: 6

```
Met Gln Pro Gln Glu Ser His Val His Tyr Ser Arg Trp Glu Asp
1               5                   10                  15
```

<210> SEQ ID NO 7
<211> LENGTH: 15
<212> TYPE: PRT
<213> ORGANISM: Homo sapiens

<400> SEQUENCE: 7

```
Ser Arg Trp Glu Asp Gly Ser Arg Asp Gly Val Ser Leu Gly Ala
1               5                   10                  15
```

<210> SEQ ID NO 8
<211> LENGTH: 15
<212> TYPE: PRT
<213> ORGANISM: Homo sapiens

<400> SEQUENCE: 8

```
Gly Val Ser Leu Gly Ala Val Ser Ser Thr Glu Glu Ala Ser Arg
1               5                   10                  15


<210> SEQ ID NO 9
<211> LENGTH: 15
<212> TYPE: PRT
<213> ORGANISM: Homo sapiens

<400> SEQUENCE: 9

Glu Ala Ser Arg Cys Arg Arg Ile Ser Gln Arg Leu Cys Thr Gly
1               5                   10                  15


<210> SEQ ID NO 10
<211> LENGTH: 16
<212> TYPE: PRT
<213> ORGANISM: Homo sapiens

<400> SEQUENCE: 10

Cys Pro Glu Ser Trp His Ser Tyr Met Arg Val Gln His Glu Gln Asp
1               5                   10                  15


<210> SEQ ID NO 11
<211> LENGTH: 18
<212> TYPE: DNA
<213> ORGANISM: Artificial Sequence
<220> FEATURE:
<223> OTHER INFORMATION: cDNA primer 388588cDNAf

<400> SEQUENCE: 11

cgcacctcag cccacgac                                                  18


<210> SEQ ID NO 12
<211> LENGTH: 19
<212> TYPE: DNA
<213> ORGANISM: Artificial Sequence
<220> FEATURE:
<223> OTHER INFORMATION: cDNA primer 388588cDNAr

<400> SEQUENCE: 12

tccaggcctg tgctctcac                                                 19


<210> SEQ ID NO 13
<211> LENGTH: 33
<212> TYPE: DNA
<213> ORGANISM: Artificial Sequence
<220> FEATURE:
<223> OTHER INFORMATION: Vel negativeF PCR primer

<400> SEQUENCE: 13

gccgaattcg ccaccatgca gccccaggag agc                                 33


<210> SEQ ID NO 14
<211> LENGTH: 33
<212> TYPE: DNA
<213> ORGANISM: Artificial Sequence
<220> FEATURE:
<223> OTHER INFORMATION: Vel negativeR2 PCR primer

<400> SEQUENCE: 14

gccggatccc ccttatttgc acttgtgcac ata                                 33


<210> SEQ ID NO 15
<211> LENGTH: 20
<212> TYPE: DNA
<213> ORGANISM: Artificial Sequence
<220> FEATURE:
```

<223> OTHER INFORMATION: 388588int2f PCR primer

<400> SEQUENCE: 15
tctcctaaca gcagcctcag 20

<210> SEQ ID NO 16
<211> LENGTH: 19
<212> TYPE: DNA
<213> ORGANISM: Artificial Sequence
<220> FEATURE:
<223> OTHER INFORMATION: 388588ex4r PCR primer

<400> SEQUENCE: 16
tgtctccagg cctgtgctc 19

<210> SEQ ID NO 17
<211> LENGTH: 19
<212> TYPE: DNA
<213> ORGANISM: Artificial Sequence
<220> FEATURE:
<223> OTHER INFORMATION: 388588int3f PCR primer

<400> SEQUENCE: 17
cagctcagca aaccgcagc 19

<210> SEQ ID NO 18
<211> LENGTH: 18
<212> TYPE: DNA
<213> ORGANISM: Artificial Sequence
<220> FEATURE:
<223> OTHER INFORMATION: 388588int3r PCR primer

<400> SEQUENCE: 18
ggcgctctgc tggagtca 18

<210> SEQ ID NO 19
<211> LENGTH: 18
<212> TYPE: DNA
<213> ORGANISM: Artificial Sequence
<220> FEATURE:
<223> OTHER INFORMATION: 388588int3r2 PCR primer

<400> SEQUENCE: 19
ctgggcgctc tgctggag 18

<210> SEQ ID NO 20
<211> LENGTH: 18
<212> TYPE: DNA
<213> ORGANISM: Artificial Sequence
<220> FEATURE:
<223> OTHER INFORMATION: Allele specific PCR primer - 388588wtex3f

<400> SEQUENCE: 20
cggagtcagc ctaggggc 18

<210> SEQ ID NO 21
<211> LENGTH: 18
<212> TYPE: DNA
<213> ORGANISM: Artificial Sequence
<220> FEATURE:
<223> OTHER INFORMATION: Allele specific PCR primer - 388588mutex3f

<400> SEQUENCE: 21
ggacggagtc cagcacag 18

<210> SEQ ID NO 22
<211> LENGTH: 21
<212> TYPE: DNA
<213> ORGANISM: Artificial Sequence
<220> FEATURE:
<223> OTHER INFORMATION: LOCex3f_screen PCR primer

<400> SEQUENCE: 22
acagcctggc cacctgtctt g 21

<210> SEQ ID NO 23
<211> LENGTH: 17
<212> TYPE: DNA
<213> ORGANISM: Artificial Sequence
<220> FEATURE:
<223> OTHER INFORMATION: LOCex3r_screen PCR primer

<400> SEQUENCE: 23
ctgcggcagc gtgaggc 17

<210> SEQ ID NO 24
<211> LENGTH: 19
<212> TYPE: DNA
<213> ORGANISM: Artificial Sequence
<220> FEATURE:
<223> OTHER INFORMATION: RACE primer Vel 59F

<400> SEQUENCE: 24
ggccgcagtg ggcaggctc 19

<210> SEQ ID NO 25
<211> LENGTH: 22
<212> TYPE: DNA
<213> ORGANISM: Artificial Sequence
<220> FEATURE:
<223> OTHER INFORMATION: RACE primer Vel 176F

<400> SEQUENCE: 25
ctcaggcaag gttctccggt ga 22

<210> SEQ ID NO 26
<211> LENGTH: 22
<212> TYPE: DNA
<213> ORGANISM: Artificial Sequence
<220> FEATURE:
<223> OTHER INFORMATION: RACE primer Vel 280F

<400> SEQUENCE: 26
aggagagcca cgtccactat ag 22

<210> SEQ ID NO 27
<211> LENGTH: 22
<212> TYPE: DNA
<213> ORGANISM: Artificial Sequence
<220> FEATURE:
<223> OTHER INFORMATION: RACE primer Vel 332R

<400> SEQUENCE: 27
gcagcgtgag gcctcttctg tg 22

<210> SEQ ID NO 28
<211> LENGTH: 22
<212> TYPE: DNA
<213> ORGANISM: Artificial Sequence
<220> FEATURE:
<223> OTHER INFORMATION: RACE primer Vel 355R

<400> SEQUENCE: 28
cacagcctct gggagatcct gc 22

<210> SEQ ID NO 29
<211> LENGTH: 20
<212> TYPE: DNA
<213> ORGANISM: Artificial Sequence
<220> FEATURE:
<223> OTHER INFORMATION: RACE primer Vel 376R

<400> SEQUENCE: 29
gatgcccagc ttgcccgtgc 20

<210> SEQ ID NO 30
<211> LENGTH: 185
<212> TYPE: DNA
<213> ORGANISM: Homo sapiens
<220> FEATURE:
<221> NAME/KEY: misc_feature
<222> LOCATION: (1)..(185)
<223> OTHER INFORMATION: Exon 3 of SMIM1

<400> SEQUENCE: 30
tgaagccaca gcctggccac ctgtcttgat ctccccaccg agaaggcccc gcccctcccg 60
ctgcagcccc acagcatgca gccccaggag agccacgtcc actatagtag gtgggaggac 120
ggcagcaggg acggagtcag cctaggggct gtgtccagca cagaagaggc ctcacgctgc 180
cgcag 185

<210> SEQ ID NO 31
<211> LENGTH: 17
<212> TYPE: DNA
<213> ORGANISM: Homo sapiens
<220> FEATURE:
<221> NAME/KEY: misc_feature
<222> LOCATION: (1)..(17)
<223> OTHER INFORMATION: Sequence of 17bp deletion

<400> SEQUENCE: 31
agcctagggg ctgtgtc 17

<210> SEQ ID NO 32
<211> LENGTH: 3778
<212> TYPE: DNA
<213> ORGANISM: Homo sapiens
<220> FEATURE:
<221> NAME/KEY: misc_feature
<222> LOCATION: (1)..(3778)
<223> OTHER INFORMATION: SMIM1-mutant phenotype extended to subsequent stop codon

<400> SEQUENCE: 32
ggtgaggcgc gcggggtccg ggctgcggct tcccggtgcg gccgcagtgg gcaggtgcga 60
ctgtgcgcgg cctcgctggc tgagaactgg cgggggtggg ggcgtgccct ggactgaccc 120
ccaccggcct aacccgcggt gcggggccag ggccggaact gcccgcccgg ctccttgccc 180
ggctccttgt ggctgctggg gacccccgac accagccact ttcccttccc ggcccttagc 240
aagatcggct tctccggtca cctttatttt tttaggctcg aggcgtctgc cgcacctcag 300
cccacgacct gccccgctgg gaggtgcggg ccgctggcca ggccctgacc gcaacctggc 360
ccagaggccc cagccctcag gcaaggttct ccgggtaagt gtggggccct gaggcgctgt 420
ggggtgaaga ggtctatgga ggggcgcctg tgtacctagg gccttcctgc actcacaagc 480

-continued

```
ccccaggagg tgccaggatc cgggagcctc ccagggcctg gaggggagtc cctgatgggt    540
tcctgccgcc acacctgtga ccatcacatg agtgtggaga gacgtttact gagcaagtga    600
gggaggccag cctcaagggc cggctctggt ggctgtgcac cggggtgact tgggaacaac    660
gtgttctacg tcagcaagac aggaacccat gatcccagag ttgaacacac tgggcttgac    720
ccctcccacc gggaggccca tggtgggctg ctgctgtgga cttggagcct cagcactccc    780
gagactaatg ctgcgtggat gtcgggttgc aaggcggctg ctgcagctcc agcagctcca    840
gccatcacgt cgagtctgga agaaggaggt ggctgctgct gctttcacag aagcaaactc    900
tcccatcccc tgctgcaccc tggctcctgg accccagctg ggtgacttgg gaaagcaggg    960
gtggtggtat taagcttgtc ttacccgggt catggctgtt acctggggct ggcacattgc   1020
tgctgggacc agaatgggat tctgcacacc aggcaagagg gcgtgaacct cgggtaggca   1080
gctgaccgct ccacatgctc cgggaaaaca gcacccatac tccagtagag gctgggcctc   1140
tccgggcctg agtgccaggc tgcactgagc cagggctccc accgaaggca cactttatgg   1200
ctttgagaca gctccttctg cctctctggg ctttggggga aggcagacat ggaagtgccg   1260
ggagtctcag aactgcctgg ggcctgagtt tctgagctgg cttcttgcag gggagtggct   1320
gctgtgcctt taggcctctg tgccgatgac ctgggaggaa ggtcagcctt ccccgctgga   1380
gggggcccag caaagcctca gctcctagaa gtgaggggcc tgccattgcc tgcccgagga   1440
ccccactcct gggggccaga tgctgagagg ggacactggg ggcccagcag accagagagc   1500
tgaccccagt cccacagcct gggtgggttg tcaacttctc gtgccccctc caactcctcc   1560
acccccacac ccccttaggt aaataggagg tcgaaacaga ggccagaggg taaaggaggt   1620
gcttagagtc cgggctggct caggccggcc gggcagctgt gctagtgctt ggagttcctg   1680
ctcagtcccc gtggtctcct cgcccctctg ggcacttggg ctgccaggca ccgagctgag   1740
tgccgagatg caaagatgag tcccaggtct gcaggagttg gagcccagca gggagctggc   1800
cttggggccg ggcccctcct gctctgggca gccacccagc cctacgaccc tcctgtctct   1860
gtagggcctc cccaaggcct tgaatccacc ccggccccgt gctcagtgca tcatgccccc   1920
caagccccag ccctcctaga ggtgtgggtg ggggaggggc tgcaacccac acaggctgag   1980
gacacagctg ctgccactgc ctggggccag ccacgcatcc tccccagaca gggaccggtc   2040
tagctgtacc agccgctgcc ccggacctgc tgccctgccc cacccccccc tcccctggcc   2100
agcctcccca gaggccagaa ggcgccttat cgggcagggt taaggagggg gacagttatc   2160
aggggctgca gcctagattg ggccacaatg tcctcgtctc ttgagggtgg caggctgtgc   2220
aggctccctg ataaaagcac cggggaaggg aggctcctgg agtgtgctgg aaggaaacac   2280
tggcctccca catgcctgag gtcagggctt ggcctgagat ggaattctcg cttggtccca   2340
tcctcccggc ctgaccctgg gcaaatgact ctaccacttt gtgtctaggt cacctgttaa   2400
gtcaggcgac agacccggtg agggagtcag cccccgaccc ttagtgcccc tctcctaaca   2460
gcagcctcag agggggtctt gactgccgcc ctccatccgc ttgttttaca gtgaagccac   2520
agcctggcca cctgtcttga tctccccacc gagaaggccc cgcccctccc gctgcagccc   2580
cacagcatgc agccccagga gagccacgtc cactatagta ggtgggagga cggcagcagg   2640
gacggagtcc agcacagaag aggcctcacg ctgccgcagg tgaggggcct gagggcagcc   2700
tgccagccat agcaggctgg tgtctccctc cagagacgcc tgccctaacc cctgctaccg   2760
gccccatcac cctccacccc atcctggctg ggagcccacg gtccagcagc tcagcaaacc   2820
gcagcctttg gccttccctc tggttggctg tgggcgggga gagcttcctc tcaactccag   2880
```

```
cagagcgccc aggcccctcc ccctgaccca gaccaacggc cacagtccac ttagggggcc   2940

cctcatgcgg ccctggcctg gggctcacct ccagttggtt ctcaccccag gatctcccag   3000

aggctgtgca cgggcaagct gggcatcgcc atgaaggtgc tgggcggcgt ggccctcttc   3060

tggatcatct tcatcctggg ctacctcaca ggctactatg tgcacaagtg caaataaatg   3120

ctgccccgca tgcacgcggg gggctggccg cacacgtgag agcacaggcc tggagacaca   3180

ccccttgtac acatggaccc ccccacagac acggaccctg cggcacacac agcgcacagg   3240

gcacacgcgc tggcagccag gcacacgaag acaccaggtg cacagctgtc atcggcccca   3300

cacgggggcg cacaaacacc tggcacacag cccttcaaag gacctacaaa cagctgggca   3360

cacgtggctg ggaggcctgg gcccagcctc agcaggagct gcaggacaca cccaggctgg   3420

gccctgcggc ctggagcccc cagctacagc ctcctctctc ccagggccca gccccttccc   3480

ttgtgaaggc caggatgagg ggttccttca gcggacaaac cgagcccacc tccctggcag   3540

ccccccgggg tgggatcctc ccggctgctt tcctccgtgg gagcagtgtg cagagctgtg   3600

tggccctggg caggcccctg tcctctctgg gcctttctga ctcctggttt tgtaagggtg   3660

gctatgtgtc cccgcccctt gtctcagatg caccatatct tccttagtaa gtgggcacag   3720

ttcttcctag gcagcccacc acgcgcagag gctgggtgtg tccctcttgg ggccggcg     3778
```

<210> SEQ ID NO 33
<211> LENGTH: 3195
<212> TYPE: DNA
<213> ORGANISM: Homo sapiens
<220> FEATURE:
<221> NAME/KEY: misc_feature
<222> LOCATION: (1)..(3195)
<223> OTHER INFORMATION: SMIM1 var 1 (chr1:3691980 A/G)

<400> SEQUENCE: 33

```
ggtgaggcgc gcggggtccg ggctgcggct tcccggtgcg gccgcagtgg gcaggtgcga     60

ctgtgcgcgg cctcgctggc tgagaactgg cgggggtggg ggcgtgccct ggactgaccc    120

ccaccggcct aacccgcggt gcggggccag ggccggaact gcccgcccgg ctccttgccc    180

ggctccttgt ggctgctggg gacccccgac accagccact ttcccttccc ggcccttagc    240

aagatcggct tctccggtca cctttatttt tttaggctcg aggcgtctgc cgcacctcag    300

cccacgacct gccccgctgg gaggtgcggg ccgctggcca ggccctgacc gcaacctggc    360

ccagaggccc cagccctcag gcaaggttct ccgggtaagt gtggggccct gaggcgctgt    420

ggggtgaaga ggtctatgga ggggcgcctg tgtacctagg gccttcctgc actcacaagc    480

ccccaggagg tgccaggatc cgggagcctc ccagggcctg gaggggagtc cctgatgggt    540

tcctgccgcc acacctgtga ccatcacatg agtgtggaga gacgtttact gagcaagtga    600

gggaggccag cctcaagggc cggctctggt ggctgtgcac cggggtgact tgggaacaac    660

gtgttctacg tcagcaagac aggaacccat gatcccagag ttgaacacac tgggcttgac    720

ccctcccacc gggaggccca tggtgggctg ctgctgtgga cttggagcct cagcactccc    780

gagactaatg ctgcgtggat gtcgggttgc aaggcggctg ctgcagctcc agcagctcca    840

gccatcacgt cgagtctgga agaaggaggt ggctgctgct gctttcacag aagcaaactc    900

tcccatcccc tgctgcaccc tggctcctgg accccagctg ggtgacttgg gaaagcaggg    960

gtggtggtat taagcttgtc ttacccgggt catggctgtt acctggggct ggcacattgc   1020

tgctgggacc agaatgggat tctgcacacc aggcaagagg gcgtgaacct cgggtaggca   1080
```

```
gctgaccgct ccacatgctc cgggaaaaca gcacccatac tccagtagag gctgggcctc   1140
tccgggcctg agtgccaggc tgcactgagc cagggctccc accgaaggca cactttatgg   1200
ctttgagaca gctccttctg cctctctggg ctttgggga aggcagacat ggaagtgccg   1260
ggagtctcag aactgcctgg ggcctgagtt tctgagctgg cttcttgcag gggagtggct   1320
gctgtgcctt taggcctctg tgccgatgac ctgggaggaa ggtcagcctt ccccgctgga   1380
gggggcccag caaagcctca gctcctagaa gtgaggggcc tgccattgcc tgcccgagga   1440
ccccactcct gggggccaga tgctgagagg ggacactggg ggcccagcag accagagagc   1500
tgaccccagt cccacagcct gggtgggttg tcaacttctc gtgcccctc caactcctcc   1560
acccccacac ccccttaggt aaataggagg tcgaaacaga ggccagaggg taaaggaggt   1620
gcttagagtc cgggctggct caggccggcc gggcagctgt gctagtgctt ggagttcctg   1680
ctcagtcccc gtggtctcct cgcccctctg ggcacttggg ctgccaggca ccgagctgag   1740
tgccgagatg caaagatgag tcccaggtct gcaggagttg gagcccagca gggagctggc   1800
cttggggccg ggcccctcct gctctgggca gccacccagc cctacgaccc tcctgtctct   1860
gtagggcctc cccaaggcct tgaatccacc ccggccccgt gctcagtgca tcatgccccc   1920
caagccccag ccctcctaga ggtgtgggtg ggggaggggc tgcaacccac acaggctgag   1980
gacacagctg ctgccactgc ctggggccag ccacgcatcc tccccagaca gggaccggtc   2040
tagctgtacc agccgctgcc ccggacctgc tgccctgccc caccccccc tcccctggcc   2100
agcctcccca gaggccagaa ggcgccttat cgggcagggt taaggagggg gacagttatc   2160
aggggctgca gcctagattg ggccacaatg tcctcgtctc ttgagggtgg caggctgtgc   2220
aggctccctg ataaaagcac cggggaaggg aggctcctgg agtgtgctgg aaggaaacac   2280
tggcctccca catgcctgag gtcagggctt ggcctgagat ggaattctcg cttggtccca   2340
tcctcccggc ctgaccctgg gcaaatgact ctaccacttt gtgtctaggt cacctgttaa   2400
gtcaggcgac agacccggtg agggagtcag cccccgaccc ttagtgcccc tctcctaaca   2460
gcagcctcag agggggtctt gactgccgcc ctccatccgc ttgttttaca gtgaagccac   2520
agcctggcca cctgtcttga tctccccacc gagaaggccc cgcccctccc gctgcagccc   2580
cacagcatgc agccccagga gagccacgtc cactatagta ggtgggagaa cggcagcagg   2640
gacggagtca gcctaggggc tgtgtccagc acagaagagg cctcacgctg ccgcaggtga   2700
ggggcctgag ggcagcctgc cagccatagc aggctggtgt ctccctccag agacgcctgc   2760
cctaacccct gctaccggcc ccatcaccct ccaccccatc ctggctggga gcccacggtc   2820
cagcagctca gcaaaccgca gcctttggcc ttccctctgg ttggctgtgg gcggggagag   2880
cttcctcttg actccagcag agcgcccagg cccctccccc tgacccagac caacggccac   2940
agtccactta gggggcccct catgcggccc tggcctgggg ctcacctcca gttggttctc   3000
accccaggat ctcccagagg ctgtgcacgg gcaagctggg catcgccatg aaggtgctgg   3060
gcggcgtggc cctcttctgg atcatcttca tcctgggcta cctcacaggc tactatgtgc   3120
acaagtgcaa ataaatgctg ccccgcatgc acgcgggggg ctggccgcac acgtgagagc   3180
acaggcctgg agaca                                                    3195
```

```
<210> SEQ ID NO 34
<211> LENGTH: 3195
<212> TYPE: DNA
<213> ORGANISM: Homo sapiens
<220> FEATURE:
<221> NAME/KEY: misc_feature
```

<222> LOCATION: (1)..(3195)
<223> OTHER INFORMATION: SMIM1 var 2 (chr1:3691980 A/G)

<400> SEQUENCE: 34
ggtgaggcgc gcggggtccg ggctgcggct tcccggtgcg gccgcagtgg gcaggtgcga 60
ctgtgcgcgg cctcgctggc tgagaactgg cgggggtggg ggcgtgccct ggactgaccc 120
ccaccggcct aacccgcggt gcggggccag ggccggaact gcccgcccgg ctccttgccc 180
ggctccttgt ggctgctggg gacccccgac accagccact ttcccttccc ggcccttagc 240
aagatcggct tctccggtca cctttatttt tttaggctcg aggcgtctgc cgcacctcag 300
cccacgacct gccccgctgg gaggtgcggg ccgctggcca ggccctgacc gcaacctggc 360
ccagaggccc cagccctcag gcaaggttct ccgggtaagt gtggggccct gaggcgctgt 420
ggggtgaaga ggtctatgga ggggcgcctg tgtacctagg gccttcctgc actcacaagc 480
ccccaggagg tgccaggatc cgggagcctc ccagggcctg gaggggagtc cctgatgggt 540
tcctgccgcc acacctgtga ccatcacatg agtgtggaga gacgtttact gagcaagtga 600
gggaggccag cctcaagggc cggctctggt ggctgtgcac cggggtgact tgggaacaac 660
gtgttctacg tcagcaagac aggaacccat gatcccagag ttgaacacac tgggcttgac 720
ccctcccacc gggaggccca tggtgggctg ctgctgtgga cttggagcct cagcactccc 780
gagactaatg ctgcgtggat gtcgggttgc aaggcggctg ctgcagctcc agcagctcca 840
gccatcacgt cgagtctgga agaaggaggt ggctgctgct gctttcacag aagcaaactc 900
tcccatcccc tgctgcaccc tggctcctgg accccagctg ggtgacttgg gaaagcaggg 960
gtggtggtat taagcttgtc ttacccgggt catggctgtt acctggggct ggcacattgc 1020
tgctgggacc agaatgggat tctgcacacc aggcaagagg gcgtgaacct cgggtaggca 1080
gctgaccgct ccacatgctc cgggaaaaca gcacccatac tccagtagag gctgggcctc 1140
tccgggcctg agtgccaggc tgcactgagc cagggctccc accgaaggca cactttatgg 1200
ctttgagaca gctccttctg cctctctggg ctttggggga aggcagacat ggaagtgccg 1260
ggagtctcag aactgcctgg ggcctgagtt tctgagctgg cttcttgcag gggagtggct 1320
gctgtgcctt taggcctctg tgccgatgac ctgggaggaa ggtcagcctt ccccgctgga 1380
gggggcccag caaagcctca gctcctagaa gtgaggggcc tgccattgcc tgcccgagga 1440
ccccactcct gggggccaga tgctgagagg ggacactggg ggcccagcag accagagagc 1500
tgaccccagt cccacagcct gggtgggttg tcaacttctc gtgccccctc caactcctcc 1560
acccccacac ccccttaggt aaataggagg tcgaaacaga ggccagaggg taaaggaggt 1620
gcttagagtc cgggctggct caggccggcc gggcagctgt gctagtgctt ggagttcctg 1680
ctcagtcccc gtggtctcct cgcccctctg ggcacttggg ctgccaggca ccgagctgag 1740
tgccgagatg caaagatgag tcccaggtct gcaggagttg gagcccagca gggagctggc 1800
cttggggccg ggcccctcct gctctgggca gccacccagc cctacgaccc tcctgtctct 1860
gtagggcctc cccaaggcct tgaatccacc ccggccccgt gctcagtgca tcatgccccc 1920
caagccccag ccctcctaga ggtgtgggtg ggggaggggc tgcaacccac acaggctgag 1980
gacacagctg ctgccactgc ctggggccag ccacgcatcc tccccagaca gggaccggtc 2040
tagctgtacc agccgctgcc ccggacctgc tgccctgccc caccccccc tcccctggcc 2100 agcctcccca gaggccagaa ggcgccttat cgggcagggt taaggagggg gacagttatc 2160
aggggctgca gcctagattg ggccacaatg tcctcgtctc ttgagggtgg caggctgtgc 2220

```
aggctccctg ataaaagcac cggggaaggg aggctcctgg agtgtgctgg aaggaaacac   2280

tggcctccca catgcctgag gtcagggctt ggcctgagat ggaattctcg cttggtccca   2340

tcctcccggc ctgaccctgg gcaaatgact ctaccacttt gtgtctaggt cacctgttaa   2400

gtcaggcgac agacccggtg agggagtcag cccccgaccc ttagtgcccc tctcctaaca   2460

gcagcctcag agggggtctt gactgccgcc ctccatccgc ttgttttaca gtgaagccac   2520

agcctggcca cctgtcttga tctccccacc gagaaggccc cgcccctccc gctgcagccc   2580

cacagcatgc agccccagga gagccacgtc cactatagta ggtgggagga cggcagcagg   2640

gacggagtca gcctaggggc tgtgtccagc acagaagagg cctcacgctg ccgcaggtga   2700

ggggcctgag ggcagcctgc cagccatagc aggctggtgt ctccctccag agacgcctgc   2760

cctaacccct gctaccggcc ccatcaccct ccaccccatc ctggctggga gcccacggtc   2820

cagcagctca gcaaaccgca gcctttggcc ttccctctgg ttggctgtgg gcggggagag   2880

cttcctcttg actccagcag agcgcccagg cccctccccc tgacccagac caacggccac   2940

agtccactta gggggcccct catgcggccc tggcctgggg ctcacctcca gttggttctc   3000

accccaggat ctcccagagg ctgtgcacgg gcaagctggg catcgccatg aaggtgctgg   3060

gcggcgtggc cctcttctgg atcatcttca tcctgggcta cctcacaggc tactatatgc   3120

acaagtgcaa ataaatgctg ccccgcatgc acgcgggggg ctggccgcac acgtgagagc   3180

acaggcctgg agaca                                                    3195
```

```
<210> SEQ ID NO 35
<211> LENGTH: 497
<212> TYPE: DNA
<213> ORGANISM: Homo sapiens
<220> FEATURE:
<221> NAME/KEY: misc_feature
<222> LOCATION: (1)..(497)
<223> OTHER INFORMATION: cDNA of SMIM1 variant (transcript according to
      5' and 3' RACE in blood)

<400> SEQUENCE: 35

cagagacgcg gggacacagg ctcgaggcgt ctgccgcacc tcagcccacg acctgccccg     60

ctgggaggtg cgggccgctg gccaggccct gaccgcaacc tggcccagag gccccagccc    120

tcaggcaagg ttctccggtg aagccacagc ctggccacct gtcttgatct ccccaccgag    180

aaggccccgc ccctcccgct gcagccccac agcatgcagc cccaggagag ccacgtccac    240

tatagtaggt gggaggacgg cagcagggac ggagtcagcc taggggctgt gtccagcaca    300

gaagaggcct cacgctgccg caggatctcc cagaggctgt gcacgggcaa gctgggcatc    360

gccatgaagg tgctgggcgg cgtggccctc ttctggatca tcttcatcct gggctacctc    420

acaggctact atgtgcacaa gtgcaaataa atgctgcccc gcatgcacgc ggggggctgg    480

ccgcaaaaaa aaaaaaa                                                   497
```

```
<210> SEQ ID NO 36
<211> LENGTH: 480
<212> TYPE: DNA
<213> ORGANISM: Homo sapiens
<220> FEATURE:
<221> NAME/KEY: misc_feature
<222> LOCATION: (1)..(480)
<223> OTHER INFORMATION: cDNA of SMIM1 variant (transcript according to
      5' and 3' RACE in blood; 17bp deletion)

<400> SEQUENCE: 36

cagagacgcg gggacacagg ctcgaggcgt ctgccgcacc tcagcccacg acctgccccg     60
```

-continued

```
ctgggaggtg cgggccgctg gccaggccct gaccgcaacc tggcccagag gccccagccc    120

tcaggcaagg ttctccggtg aagccacagc ctggccacct gtcttgatct ccccaccgag    180

aaggccccgc ccctcccgct gcagccccac agcatgcagc cccaggagag ccacgtccac    240

tatagtaggt gggaggacgg cagcagggac ggagtccagc acagaagagg cctcacgctg    300

ccgcaggatc tcccagaggc tgtgcacggg caagctgggc atcgccatga aggtgctggg    360

cggcgtggcc ctcttctgga tcatcttcat cctgggctac ctcacaggct actatgtgca    420

caagtgcaaa taaatgctgc cccgcatgca cgcggggggc tggccgcaaa aaaaaaaaaa    480
```

METHODS AND TOOLS FOR VEL BLOOD GROUP TYPING

REFERENCE TO A SEQUENCE LISTING SUBMITTED VIA EFS-WEB

The content of the ASCII text file of the sequence listing named "20150326_310000_001US1_seq" which is 31.3 kb in size has a creation date of Mar. 26, 2015, and electronically submitted via EFS-Web herewith the application is the same as that provided in PCT/EP2013/070403 and is incorporated herein by reference in its entirety.

FIELD OF INVENTION

The present invention relates to the technical field of blood group determination, in particular to Vel blood group typing and specifically to tools and methods for discriminating between Vel positive and Vel negative individuals.

BACKGROUND OF INVENTION

In addition to the human blood group systems, erythrocyte antigens exist which do not yet meet the definition of a blood group system. Most of these antigens are either nearly universal in human blood (high-prevalence antigens) or extremely rare (low-prevalence antigens). Reagents to test for these antigens are difficult to find and many cannot be purchased commercially to date.

The molecular genetic identity of many blood group antigens is well established and a variety of polymerase chain reaction (PCR)-based techniques exist for their detection. Many laboratories have developed in-house protocols or adopted the test systems of others for predicting blood group antigens by deoxyribonucleic acid (DNA) typing on a routine basis.

DNA-based assays can readily determine homozygosity and heterozygosity, and in some cases, hemizygosity of a blood group allele, which is beyond the capability of conventional serology. Another added benefit of DNA-based blood group typing beyond the capabilities of traditional serology is the possibility to determine the foetal blood group by testing DNA derived from foetal cells in amniotic fluid or chorionic villus biopsies, or increasingly common even from cell-free foetal DNA in maternal plasma.

It is a great frustration to end users and manufacturers alike that the limiting factor in providing phenotype information on patients, blood donors and reagent red blood cells (RBCs) is the availability of reliable antisera.

There are monoclonal antibodies to many blood group antigens and thus supply is somewhat assured. However, for specificities for which monoclonal antibodies have not been raised, manufacturers still have to rely on human polyclonal antibodies as typing reagents. Many of these are increasingly in short supply, are often only weakly and/or variably-reactive, and are costly to produce. For some blood groups, volunteers have been immunised against a certain blood group antigen for reagent or medical use but raising antibodies against a high-prevalence antigen, for instance Vel as described in Issit et al (1968) Vox Sang. 15: 125-132, is not an option in human volunteers because blood units lacking the corresponding antigen are rare and the procedure could therefore constitute a safety threat.

The Vel blood group antigen, first described by Sussman and Miller (Rev. Hematol. 1952; 7:368-71), is expressed in RBCs and is one of several so-called orphan blood group antigens for which the molecular basis is unknown.

Among the orphan blood groups, Vel is considered one of the most clinically relevant, as Vel negative patients, which have been immunised following transfusion or pregnancy, and subsequently transfused with red blood cells from Vel positive donors are at risk of severe side effects including acute intravascular hemolysis.

There is currently a global lack of Vel negative blood donors available for transfusion medicine purposes. Accordingly it is desirable to provide a test which fast and efficiently can select for Vel negative donors.

The molecular background of Vel has to date been unknown and thus the only possibility to identify blood donors lacking Vel has been through phenotyping using antisera from immunised patients, a suboptimal approach from an ethics, safety and quality perspective. Tools for genetic screening are desirable as they facilitate large-scale, cost-efficient screening of blood donors for the absence of Vel, in order to increase availability of Vel negative blood.

Identification of a gene on which Vel blood group expression is dependent would permit the possible development of a screening assay which could identify Vel negative blood donors, and also means to type patients at risk of producing an unwanted antibody against the Vel antigen, or suspected to have made such antibodies.

SUMMARY OF INVENTION

Almost all humans carry the Vel blood group antigen on the surface of their red blood cells (RBCs). Individuals who lack Vel can form anti-Vel antibodies that may cause severe haemolytic reactions upon blood transfusion, and also cause haemolytic disease of the foetus and newborn in rare pregnancies.

Accordingly, it is essential to identify Vel negative individuals prior to blood transfusion in order to avoid said severe reactions. As discussed herein above, for some blood groups, volunteers have been immunised against a certain blood group antigen for reagent or medical use. However but raising antibodies against a high-prevalence antigen is not an option in human volunteers because blood units lacking the corresponding antigen are rare and the procedure could therefore constitute a safety threat. The present inventors have addressed the problem of applying DNA-based testing to the Vel blood group, to fill the gaps left by the unavailability of appropriate reagent antisera.

The present inventors have uncovered the genetic basis of Vel and found a mutation (specifically, a 17-basepair deletion) in a previously uncharacterized gene (small integral membrane protein 1; Official Gene Symbol SMIM1, previously LOC388588; Entrez Gene ID 388588), for which all tested Vel negative individuals were homozygous, as verified by pedigreed Vel negative and Vel positive controls. Expression of the Vel blood group antigen on RBCs is dependent on expression of the SMIM1 gene, the mRNA of which encodes a type 1 transmembrane protein. The Vel-negative phenotype occurs when this protein cannot be expressed. These results unveil the previously unknown molecular mechanism by which the Vel blood group antigen is expressed.

The present results demonstrate that an individual's Vel blood group is determined by SMIM1, located in a 97-kb haplotype block on chromosome 1p36.32.

This gene encodes an evolutionary conserved type 1 membrane protein that is co-expressed with known RBC genes and contains binding sites for transcription factors linked with erythroid development.

All Vel negative individuals (n=36) examined in the study were homozygous for a 17-basepair deletion in exon 3 that shifts the reading frame 5' of the region coding for the transmembrane domain, resulting in a null phenotype where Vel antigens are not expressed.

Absence of a protein product of SMIM1 in RBC membranes from homozygous deletion carriers was confirmed using Western blot using antibodies raised against the N-terminal domain of the protein.

Overexpression of wild type SMIM1 following transfection of haematopoietic cells increased the reactivity with anti-Vel-containing sera, whereas the mutant allele did not.

Molecular genetic screening for the deletion among blood donors from southern Sweden revealed that 1/17 are heterozygous carriers, corresponding to a homozygote frequency of approximately 1/1150.

In one main aspect the present invention relates to a method of identifying the Vel phenotype of an individual, said method comprising discriminating between Vel positive and Vel negative phenotypes by analysing in a biological sample from said individual the composition of the SMIM1 gene, wherein at least one intact SMIM1 gene is indicative of a Vel positive phenotype, and wherein a SMIM1 gene comprising a mutation resulting in abolished protein expression, or in expression of a non-functional protein, is indicative of a Vel negative phenotype.

The SMIM1 gene is typically defined by a polynucleotide sequence comprising SEQ ID NO. 1, or a sequence variant thereof. The concept SMIM1 gene may however comprise also naturally-occurring regulatory elements such as but not limited to promoters and enhancers.

In one aspect, the present invention concerns a method of detection and/or quantitation of a splice variant of SMIM1 in a sample, the method comprising making complementary DNA (cDNA) from messenger RNA (mRNA) in the sample, amplifying the entire or portions of the cDNA corresponding to the SMIM1 gene, such as SEQ ID NO. 3, 4, 35 or 36, or parts thereof and detecting and quantifying the amplified cDNA in order to detect or quantify the splice variant.

In one aspect, the invention concerns a method of identifying a Vel positive individual, comprising the steps:

a) performing amplification of a polynucleotide of the subject by contacting a polynucleotide from a cell of the subject with an oligonucleotide primer having a sequence being complementary to at least 10 consecutive nucleotides of a polynucleotide encoding the Vel antigen;

b) detecting an amplicon from step (a), whereby the detection of an amplicon identifies the subject as a Vel positive individual.

In another aspect, the invention concerns a method of identifying a Vel negative individual, comprising the steps:

a) performing amplification of a polynucleotide of the subject by contacting a polynucleotide from a cell of the subject with an oligonucleotide primer having a sequence being complementary to at least 10 consecutive nucleotides of a polynucleotide encoding the Vel antigen;

b) detecting an amplicon from step (a), whereby the detection of an amplicon identifies the subject as a Vel negative individual.

In another aspect the present invention concerns a method of detecting in a sample, a cell that expresses a Vel antigen comprising detecting in the sample a polynucleotide that encodes a Vel antigen.

The SMIM1 gene which typically comprises SEQ ID NO. 1 or a sequence variant thereof encodes a polypeptide which is associated with the Vel antigen.

Expression of the Vel blood group antigen on RBCs is dependent on expression of the SMIM1 gene, the mRNA of which encodes a type 1 transmembrane protein. The Vel-negative phenotype occurs when this protein cannot be expressed, for instance due to the 17-bp deletion.

Thus far, the only way to identify Vel negative individuals has been by cell-based phenotyping assays involving antiserum from immunized patients, the supply of which is severely limited. By contrast, the genetic testing of the present method can be performed on virtually unlimited numbers of individuals at low cost, enabling screening of large blood donor populations to identify more Vel negative donors and facilitating the procurement of Vel negative blood units to patients in need.

Hence in one aspect, the present invention concerns a method for blood transfusion comprising the steps:

a) applying the method of discriminating between Vel negative and Vel positive patients as defined herein;

b) electing from a donor or blood bank i) Vel positive blood if the method of a) determines that the patient is Vel positive, or ii) Vel negative blood if the method of a) determines that the patient is Vel negative;

c) transfusing the patient with the blood elected in b).

In one aspect, the method for blood transfusion is applicable to a method of treatment of a disease or disorder associated with erythrocytes, such as, but not limited to anemia.

Pregnant Vel negative females (mothers) may carry Vel positive foetuses. When erythrocytes from the Vel positive foetus are transferred to the Vel negative mother, this may result in an immune response of the mother, thus raising anti-Vel antibodies against the Vel positive erythrocytes. This is potentially lethal for the foetus, especially during a second or subsequent pregnancy of the Vel negative female. Accordingly, in one aspect the present invention concerns a method of prophylactic treatment of a Vel negative pregnant female individual comprising:

a) identifying a Vel negative individual by applying the method as defined in herein above, and b) administering to said Vel negative pregnant female individual a therapeutically effective amount of an anti-Vel antibody, thus neutralizing Vel positive erythrocytes originating from the Vel positive foetus carried by said Vel negative pregnant female individual.

The basis for the method of the present invention is the finding by the present inventors, of the molecular basis discriminating Vel negative and Vel positive individuals, respectively. Accordingly, in an important aspect, the present invention concerns an isolated polynucleotide comprising a sequence variant of SEQ ID NO. 1, or an isolated polynucleotide comprising a sequence variant of a sequence being complementary to said SEQ ID NO. 1, wherein the sequence variant comprises at least one mutation or polymorphism, and wherein the mutation or polymorphism results in abolished transcription and/or protein translation and/or absence of the protein on the cell surface.

In another aspect, the present invention concerns an isolated polynucleotide comprising a sequence variant of SEQ ID NO. 1, or an isolated polynucleotide comprising a sequence variant of a sequence being complementary to said SEQ ID NO. 1, wherein the sequence variant comprises at least one mutation or polymorphism, wherein the mutation or polymorphism results in translation of a Vel antigen having an altered epitope, wherein the altered epitope is not recognised by anti-Vel antibodies.

The present inventors have developed tools for performing the necessary analyses in order to appropriately discriminate between Vel positive and Vel negative samples. One such important tool includes oligonucleotide primers for the production of an amplicon which may be detected by e.g. gel electrophoresis. In one such aspect, the present invention concerns an isolated oligonucleotide having a sequence selected from the group consisting of SEQ ID NO. 11, 12, 13, 14, 15, 16, 17, 18, 19, 20, 21, 22 and 23, as well as use of said isolated oligonucleotide in the method defined herein.

The inventors have identified that the Vel antigen is dependent on and therefore represented by the polypeptide having SEQ ID NO. 5 or a sequence variant or a fragment thereof. The polypeptide is a useful tool in the methods of the present invention. Accordingly in one aspect, the present invention concerns an isolated polypeptide having the sequence of SEQ ID NO. 5, or a fragment or a variant thereof, wherein said fragment comprises at least 20 consecutive amino acid residues of SEQ ID NO. 5, and wherein said variant is at least 80% identical to SEQ ID NO. 5, and wherein said variant comprises at least one Serine and/or Threonine residue, and wherein at least one Serine and/or Threonine residue of said SEQ ID NO. 5 or said fragment or variant thereof, is O-glycosylated.

Important polypeptide fragments defining the Vel antigen are fragments of SEQ ID NO. 5. Thus in one aspect, the present invention concerns an isolated peptide having a sequence selected from the group consisting of SEQ ID NOs. 6, 7, 8, 9 and 10.

An isolated polynucleotide, encoding upon expression a peptide having a sequence selected from the group consisting of SEQ ID NOs. 6, 7, 8, 9 and 10 is also an aspect of the present invention.

The present inventors have raised antibodies capable of recognizing the above defined peptide fragments. Accordingly, in one aspect, the present invention concerns an antibody capable of recognising an epitope of a Vel antigen, wherein the epitope is defined by a peptide sequence selected from the group consisting of SEQ ID NOs. 6, 7, 8, 9 and 10, or an O-glycosylated peptide sequence selected from SEQ ID NOs. 6, 7, 8, 9 and 10.

In another aspect, the invention concerns an antibody capable of recognising an epitope of a Vel antigen, wherein the epitope is defined by a peptide having the SEQ ID NO. 5, or a fragment or variant thereof, wherein the variant is at least 60%, such as at least 70%, such as at least 80%, such as at least 85%, such as at least 90%, such as at least 95%, such as at least 98%, such as at least 99% identical to said SEQ ID NO. 5, or an O-glycosylated variant of SEQ ID NO. 5, such as at least 60%, such as at least 70%, such as at least 80%, such as at least 85%, such as at least 90%, such as at least 95%, such as at least 98%, such as at least 99% identical to a O-glycosylated variant of SEQ ID NO. 5.

Furthermore the present invention also concerns a method of making a polyclonal antibody, the method comprising:

a) immunizing a mammal with the polypeptide or peptide as defined herein above, under conditions to elicit an antibody response;

b) isolating antibodies from said mammal;

c) screening the isolated antibodies with the polypeptide or polypeptide fragment thereby identifying a polyclonal antibody that binds specifically to the polypeptide or polypeptide fragment of step a).

In a further aspect the invention concerns a method of making a monoclonal antibody, the method comprising:

a) immunizing a mammal with the polypeptide or peptide as defined herein above, under conditions to elicit an antibody response;

b) i) isolating antibody producing cells from the mammal, or ii) cloning the antibody coding sequence and express in other cells rendering antibody producing cells;

c) fusing the antibody producing cells with immortalized cells in culture to form monoclonal antibody-producing hybridoma cells;

d) culturing the hybridoma cells;

e) isolating from the culture monoclonal antibodies which bind specifically to the polypeptide or polypeptide fragment of step a).

It is within the scope of the present invention to provide user-friendly tools such as kits, suitable for discriminating between samples from Vel negative and Vel positive individuals.

In another such aspect the invention concerns a kit for detecting a Vel antigen and/or discriminating between samples from Vel negative and Vel positive individuals, said kit comprising at least two isolated oligonucleotide primers selected from the group consisting of SEQ ID NO. 11, 12, 13, 14, 15, 16, 17, 18, 19, 20, 21, 22 and 23.

In one embodiment the present invention concerns an oligonucleotide being complementary to the oligonucleotide primers defined herein above, wherein said oligonucleotide primer is an oligonucleotide primer being complementary to a sequence selected from the group consisting of SEQ ID NO. 11, 12, 13, 14, 15, 16, 17, 18, 19, 20, 21, 22 and 23.

In one embodiment, the oligonucleotide primer is a forward primer of an oligonucleotide primer selected from the group consisting of SEQ ID NO. 11, 12, 13, 14, 15, 16, 17, 18, 19, 20, 21, 22 and 23.

In another embodiment, the oligonucleotide primer is a reverse primer of an oligonucleotide primer selected from the group consisting of SEQ ID NO. 11, 12, 13, 14, 15, 16, 17, 18, 19, 20, 21, 22 and 23.

In another embodiment, the oligonucleotide primer is a sense primer of an oligonucleotide primer selected from the group consisting of SEQ ID NO. 11, 12, 13, 14, 15, 16, 17, 18, 19, 20, 21, 22 and 23.

In another embodiment, the oligonucleotide primer is an antisense primer of an oligonucleotide primer selected from the group consisting of SEQ ID NO. 11, 12, 13, 14, 15, 16, 17, 18, 19, 20, 21, 22 and 23.

The present invention is well suited for adaptation to high-throughput scale by applying oligonucleotides, peptides or antibodies to a surface thus forming a device for detecting Vel antigens or Vel antigen associated molecules.

In one such aspect the present invention concerns a kit comprising a microchip array comprising one or more polynucleotides selected from the group consisting of SEQ ID NO. 1, 2, 3, 4, 11, 12, 13, 14, 15, 16, 17, 18, 19, 20, 21, 22, 23, 32, 33, 34, 35 and 36 or one or more fragments of said polynucleotide.

In another such aspect the invention concerns a kit comprising a microchip array comprising one or more peptides or polypeptides selected from the group consisting of SEQ ID NO. 5, 6, 7, 8, 9 and 10, or one or more fragments of said peptide or polypeptide wherein said fragment comprises at least 5 consecutive amino acids of said SEQ ID NO. 5, 6, 7, 8, 9 and 10.

For certain purposes, such as cytology applications including but not limited to immunohematology and detection of antibodies it may be useful to provide cells presenting a Vel antigen. Thus in one aspect the invention concerns a kit comprising cells presenting a Vel antigen.

In a further aspect the present invention concerns the use of an isolated polynucleotide, which upon expression encodes a polypeptide having the amino acid sequence of SEQ ID NO: 5, or a fragment or variant thereof, as a medicament or as a diagnostic marker.

DESCRIPTION OF DRAWINGS

FIG. 9*b* shows western blotting with the polyclonal rabbit anti-SMIM1 of HEL cells following transduction with a transduction control (HEL wt), and with shRNA clone G at an MOI of 0.5 U, 1.0 U, 2.0 U, 3.0 U, 4.0 U. Knockdown of both mRNA transcript and protein is clearly demonstrated.

DETAILED DESCRIPTION OF THE INVENTION

SMIM1 Gene

Figure 1:
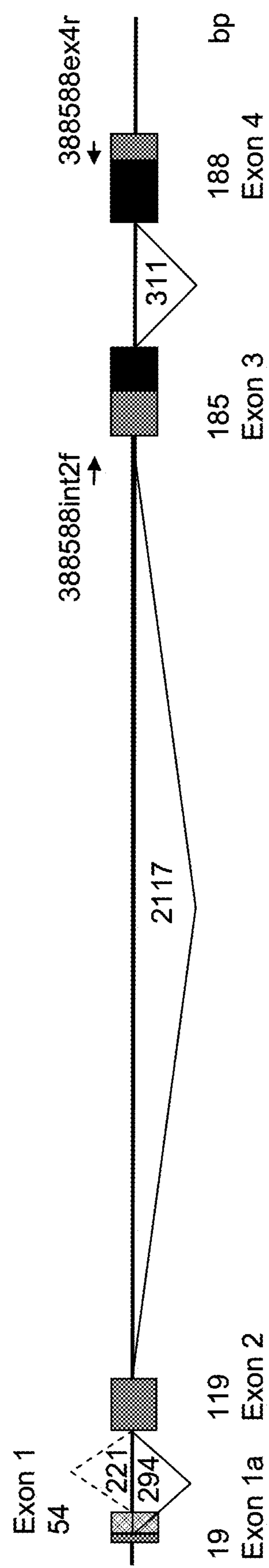
FIG. 1: Genomic organisation of SMIM1. Exons are shown as boxes while intronic sequence is depicted as a line. Dark grey represents non-coding exons, except for the alternative exon 1 (labelled exon 1a in the figure) which is in light grey; black represents the open reading frame. Positions of the genomic DNA amplification primers are shown by the arrows.

The Vel blood group antigen is located on red blood cells (RBCs) and is one of several so-called orphan blood group antigens for which the molecular basis is unknown. It is clinically important and thus identification of the carrier molecule would permit the development of a screening assay to identify blood donors appropriate for donation to immunized Vel negative/negative patients, and also patients at risk of producing an unwanted antibody.

The present inventors provided understanding of the molecular and genetic basis of the Vel blood group antigen. This has been achieved through a range of serological and biochemical investigations, including investigations of candidate genes. These investigations resulted in estimates of the size of the red blood cell protein carrying the Vel antigen and a likely homodimer configuration.

A hypothesis that the gene encoding the Vel blood group antigen could potentially be triangulated via genome-wide genetic screening using single-nucleotide polymorphism (SNP) microarrays was based on three observations:

(a) the Vel negative phenotype is believed to be more common in Sweden (1:1700, compared to approx. 1:4000 in other populations), (b) the Vel negative phenotype is inherited in an apparently autosomal-recessive manner, and (c) the gene encoding the Vel antigen, like several other blood group genes, could be preferentially expressed on erythrocytes.

Together, these observations made the inventors suggest that the Vel negative phenotype could be caused by a single founder mutation in the Swedish population, in which case a genome-wide genetic screen could succeed despite the relatively limited number of DNA samples from Vel negative individuals available.

Accordingly, genome-wide SNP profiles of Vel negative donors were collected using Illumina Human Omni 2.5M-Quad microarrays. Using a computational strategy conceived and executed collaboratively by the present inventors, a region on chromosome 1 containing 5 genes was identified.

Following review of the characteristics of these genes, it was determined that SMIM1 was the most promising because:

(a) its predicted structure corresponded to a transmembrane protein, (b) its predicted size matched the size estimates of the inventor's earlier biochemical studies, and (c) analyses of pre-existing gene expression microarray data retrieved from public data bases indicated that it was preferentially expressed in red blood cell precursors.

With this information in hand, the inventors determined the DNA sequence of SMIM1 in Vel negative donors and found a 17-basepair deletion that is predicted to destroy the transmembrane domain of the protein, providing sufficient explanation for a so-called null or knock-out phenotype.

Subsequent genetic studies have identified the exact same 17-base-pair deletion in all 36 Vel negative donors from Sweden, UK and the USA tested to date, suggesting that it is indeed the predominating cause of the Vel negative phenotype. This has set the stage for identification of Vel negative blood donors by genetic testing.

The basis for the method of the present invention is the finding by the present inventors, of the molecular basis discriminating Vel negative and Vel positive individuals, respectively. Accordingly, in an important aspect, the present invention concerns an isolated polynucleotide comprising a sequence variant of SEQ ID NO. 1, or an isolated polynucleotide comprising a sequence variant of a sequence being complementary to said SEQ ID NO. 1, wherein the sequence variant comprises at least one non-sense mutation, and wherein the nonsense mutation results in abolished transcription and/or protein translation thus resulting in absence of the protein on the cell surface.

In one embodiment the non-sense mutation is a deletion, such as a deletion of between 1 and 100 nucleotides, such as between 2 and 90 nucleotides, such as between 3 and 80 nucleotides, such as between 4 and 70 nucleotides, such as between 5 and 60 nucleotides, such as between 6 and 50 nucleotides, such as between 7 and 40 nucleotides, such as between 8 and 30 nucleotides, such as between 9 and 25 nucleotides, such as between 10 and 20 nucleotides, such as between 15 and 19 nucleotides, such as between 16 and 18 nucleotides, such as 17 nucleotides.

In an important embodiment, the deletion is a deletion of 17 nucleotides.

In one embodiment, the sequence variant of the above defined polynucleotide is between 60% and 99.9% identical, such as between 70% and 99.8% identical, such as between 80% and 99.7% identical, such as between 90% and 99.8% identical, such as between 95% and 99.56% identical, such as between 96% and 99.55% identical, such as between 97% and 99.54% identical, such as between 98% and 99.9% identical, such as at least 60%, such as at least 70%, such as at least 80%, such as at least 90%, such as at least 95%, such as at least 96%, such as at least 97%, such as at least 98%, such as at least 99%, such as at least 99.1, at least 99.9%, such as 100% identical to SEQ ID NO. 1 or a sequence being complementary to SEQ ID NO. 1. or a sequence being complementary to SEQ ID NO. 1.

In one embodiment, the sequence variant of the above isolated polynucleotide has the sequence selected from the group consisting of SEQ ID NO. 2 and 4 or a sequence being complementary to SEQ ID NO. 2 or 4.

In one embodiment, the isolated polynucleotide has the sequence of SEQ ID NO: 31, and in another embodiment the isolated polynucleotide comprises the sequence of SEQ ID NO: 31.

Tools for Amplifying SMIM1

The present inventors have developed tools for performing the necessary analyses in order to appropriately discriminate between Vel positive and Vel negative samples, methods which are described herein below. One important tool useful in said methods includes oligonucleotide primers for the production of an amplicon (an amplified polynucleotide sequence) which may be detected by conventional methods, e.g. gel electrophoresis. In one such aspect, the present invention concerns an isolated oligonucleotide having a sequence selected from the group consisting of SEQ ID NO. 11, 12, 13, 14, 15, 16, 17, 18, 19, 20, 21, 22 and 23, as well as use of said isolated oligonucleotide in the method defined herein.

Methods for Vel Negative/Vel Positive Discrimination

The findings of the 17 bp deletion described herein above is clinically very important as the only way to identify Vel negative blood donors before the priority date of the present application has been by cell based phenotyping assays based on serum or plasma from immunized patients, the supply and quality of which are severely limited.

By contrast, genetic testing can be performed on virtually unlimited numbers of patients at low cost, enabling screening of large blood donor populations to identify more Vel negative donors and facilitating the procurement of Vel negative blood units to patients in need.

It is an overall object of the present invention to provide a method comprising:

a) detecting an allele comprising a variation in the SMIM1 gene;
b) determining if the variation of a) is homozygous or heterozygous;
c) determining if the variation of a) and b) is Vel negative or Vel positive.

The analysis can be performed using any suitable method known by those of skill in the art. Non-limiting examples of suitable methods include Gel electrophoresis, Real-time PCR, Mass spectrometry (e.g. MALDI-TOF), Flurochrome-labelled oligonucleotide extention, Fluorochrome-labelled sequence-specific amplification (e.g. xMAP technology), sequencing including dye-termination sequencing, and other next generation sequencing techniques that include but are not limited to Pyrosequencing, sequencing by ligation (SOLiD) and Ion Torrent semiconductor sequencing.

A Vel negative individual according to the present invention has a Vel negative phenotype. A Vel positive individual according to the present invention has a Vel positive phenotype. Accordingly the expressions Vel negative individual and Vel negative phenotype are use interchangeably herein, the meaning of which is well known by the person of skill in the art.

The methods provided in the present invention have the aim of characterizing the Vel antigen phenotype of an individual such as a blood donor or blood recipient (patient receiving blood e.g. via transfusion). A blood group antigen phenotype is defined by the presence or absence of blood group antigens on the surface of the erythrocyte. Blood group antigens are unique, inherited, structural differences found on the proteins, glycoproteins and glycolipids that make up the external surface of the erythrocyte. All blood group antigens have been identified by specific antibodies present in the plasma of different individuals. With the exception of some “naturally-occurring” antibodies, most antibodies to blood group antigens have been made as a response to the introduction e.g. by transfusion or pregnancy, of erythrocytes carrying a blood group antigen that is absent from the patient’s erythrocytes. These antibodies persist in the circulation and may cause clinical sequelae such as a transfusion reaction, or haemolytic disease of the newborn. However, while many antibodies to blood group antigens have the potential to cause accelerated erythrocyte survival and hemolysis, very few antibodies to blood group antigens are encountered in the routine transfusion setting.

Over 300 blood group antigens have been identified. Most of these are catalogued into one of 33 blood group systems, according to the RBC membrane component on which the antigen resides. Antigens that do not belong in a blood group system are assigned to one of six blood group collections (201 series) or to either the 700 series (low frequency antigens) or the 901 series (high frequency antigens) as defined by the International Society for Blood Transfusion (ISBT) Working Party on Red Cell Immunogenetics and Blood Group Terminology.

Thus, if an individual is described as carrying the Vel negative phenotype, this means that the individual's erythrocytes lack the Vel blood group antigen. Phenotype can also be used to summarize the known antigens on a person's erythrocytes, e.g. Patient A's phenotype was D+C−E+c+e+, K−, Fy(a+b+). This means that Patient A's erythrocytes expressed E, c, e, $Fy^a$ and $Fy^b$ blood group antigens but did not express C or K antigens.

In one main aspect, the present invention thus concerns a method of identifying the Vel phenotype of an individual, said method comprising discriminating between Vel positive and Vel negative phenotypes by analysing in a biological sample from said individual the composition of the SMIM1 gene, wherein at least one intact SMIM1 gene is indicative of a Vel positive phenotype, and wherein a SMIM1 gene comprising a mutation resulting in abolished protein expression, or in expression of a non-functional protein, is indicative of a Vel negative phenotype.

The mutation described herein above may be any mutation, however in a preferred embodiment the mutation is a deletion, such as a deletion of SEQ ID NO: 31 from the wild type SMIM1 gene. The mutation may also be a fragment or variant of said SEQ ID NO: 31, wherein said fragment comprises at least 12 consecutive nucleotides of said SEQ ID NO: 31, and wherein in said variant, no more than 5 nucleotides have been altered to 5 different nucleotides.

In one embodiment the mutation is a SNP, such as a dinucleotide exchange 2907t>c and 2908g>a of SEQ ID NO:1.

In one embodiment the SMIM1 gene comprises multiple mutations such as a combination of said deletion and said SNPs.

A heterozygous disruption of the SMIM1 results in a Vel positive phenotype, although that individual would only have weak expression of SMIM1. Vel negative phenotypes are thus homozygous for a disruption in the SMIM1 gene.

In one embodiment the method according to the present invention comprises the steps:

a) providing a sample,
b) detecting in the sample an allele comprising SMIM1,
c) determining whether the sample is from a homozygous or heterozygous subject,
d) determining if the sample is from a subject with a Vel positive or a Vel negative phenotype.

In one aspect the present invention relates to a method of determining the Vel blood group phenotype of an individual, said method comprising discriminating between Vel positive and Vel negative phenotypes by analysing in a biological sample the composition of:

a) a SMIM1 gene, and/or
b) a transcript of a SMIM1 gene, and/or
c) a polypeptide encoded by a SMIM1 gene.

In one embodiment the present invention relates to a method of identifying a Vel negative phenotype said method comprising discriminating between Vel positive and Vel negative phenotypes by analysing in a biological sample the composition of:

a) a SMIM1 gene, and/or
b) a transcript of a SMIM1 gene, and/or
c) a polypeptide encoded by a SMIM1 gene.

In another embodiment the present invention relates to a method of identifying a Vel positive phenotype said method comprising discriminating between Vel positive and Vel negative phenotypes by analysing in a biological sample the composition of:

a) a SMIM1 gene, and/or
b) a transcript of a SMIM1 gene, and/or
c) a polypeptide encoded by a SMIM1 gene.

SMIM1 is typically defined by a polynucleotide sequence comprising SEQ ID NO. 1 or a sequence variant thereof. The concept SMIM1 gene may however comprise naturally occurring regulatory elements such as but not limited to promoters and enhancers.

In one aspect the present invention comprises detecting SMIM1 associated genetic markers located upstream or downstream of SEQ ID NO. 1 in the genome. This may be performed by applying any one of the methods of the present invention where the amplification is performed by:

i) providing a biological sample comprising genomic DNA,
ii) contacting the sample comprising genomic DNA with a first and a second PCR oligonucleotide primer,
 wherein said first primer comprises at least 10 nucleotides being complementary to at least 10 consecutive nucleotides located upstream (5') of nucleotide position 1 of SEQ ID NO. 1, and
 wherein said second primer comprises at least 10 nucleotides being complementary to at least 10 consecutive nucleotides located downstream (3') of nucleotide position 3195 of SEQ ID NO. 1,
 with the proviso that said first and said second primer are not both selected from a sequence being complementary to SEQ ID NO. 31;
iii) obtaining an amplicon;
iv) performing qualitative and/or quantitative analysis of the amplicon of step iii);

comparing the length of the amplicon, to at least one Vel positive control, wherein a length differing from the Vel positive control indicates that the sample is Vel negative.

In one embodiment the SMIM1 gene comprises the sequence of SEQ ID NO: 1 or a sequence variant thereof wherein the sequence variant is between at least 60%, such as at least 70%, such as at least 80%, such as at least 90%, such as at least 95%, such as at least 96%, such as at least 97%, such as at least 98%, such as at least 99%, such as between 99.1 and 99.9%, such as between 99.4 and 99.6%, such as 100% identical to SEQ ID NO. 1 or a sequence being complementary to SEQ ID NO. 1.

In one embodiment the SMIM1 gene comprises the sequence being complementary to SEQ ID NO. 1 or a sequence variant thereof wherein the sequence variant is between at least 60%, such as at least 70%, such as at least 80%, such as at least 90%, such as at least 95%, such as at least 96%, such as at least 97%, such as at least 98%, such as at least 99%, such as between 99.1 and 99.9%, such as between 99.4 and 99.6%, such as 100% identical to the sequence being complementary to SEQ ID NO. 1

The method of the present invention can in principle be applied to any genetic material originating from any organism, however the present invention is particularly useful for detecting Vel negative blood. Thus in one embodiment the method of the present invention is for detection of Vel negative blood.

In one embodiment the method of the present invention is for detection or identification of a Vel negative subject such as a human being.

The 17 bp deletion in exon 3 of SMIM1 results in that most Vel negative individuals carry a SMIM1 gene comprising SEQ ID NO. 2 rather than SEQ ID NO. 1 which is the case for Vel positive individuals tested.

Thus, in one embodiment the method for discriminating between Vel negative and Vel positive samples, or individuals, by analysing the SMIM1 composition comprises identifying subjects whose genome comprises SEQ ID NO. 1, said subjects being Vel positive, and subjects whose genome comprises SEQ ID NO. 2, or a fragment or variant thereof, wherein the variant is at least 90% identical to said SEQ ID NO. 2, said subjects being Vel negative.

In one embodiment the method for discriminating between Vel negative and Vel positive samples, or individuals, by analysing the SMIM1 composition comprises identifying subjects whose genome comprises SEQ ID NO. 1, 3 or 35, said subjects being Vel positive, and subjects whose genome comprises SEQ ID NO. 2, 32, 33, 34 or 36, or a fragment or variant thereof, wherein the variant is at least 90% identical to said SEQ ID NO. 2, 4, 32, 33, 34 or 36, said subjects being Vel negative.

Prior to the priority date of the present application, the only way known for identifying Vel negative blood donors was by cell-based phenotyping assays based on serum or plasma from immunized patients, the supply of which is severely limited. By contrast, the genetic testing of the present method can be performed on virtually unlimited numbers of individuals at low cost, enabling screening of large blood donor populations to identify more Vel negative donors and facilitating the procurement of Vel negative blood units to patients in need.

The methods of the present invention are based on the finding of the present inventors of the molecular basis for Vel negativity. In principle, any method which utilises the differences in the DNA code of the SMIM1 gene can be applied to discriminate between Vel negative and Vel positive individuals. This also includes pre-processing the genomic DNA (gDNA) prior to performing the analysis, as well as preparing cDNA from transcribed mRNA.

Accordingly in one embodiment the method of the present invention comprising discrimination by analysis of the SMIM1 composition comprises the steps of:

a) providing a sample;
b) preparing cDNA;
c) identifying samples wherein the cDNA has the sequence of SEQ ID NO. 3 or 35, or a fragment thereof, wherein the fragment comprises at least the polynucleotide having the sequence of SEQ ID NO. 31;
d) identifying samples wherein the cDNA differs from the cDNA of SEQ ID NO. 3 or 35 by at least one nucleotide;
e) comparing c) and d),
   wherein the sample of c) is from a Vel positive subject, and
   wherein the sample of d), is from a Vel negative subject.

In another embodiment the method of the present invention comprises:

a) providing a biological sample comprising a SMIM1 polynucleotide,
b) amplifying at least a fragment of the SMIM1 polynucleotide, wherein the SMIM1 polynucleotide has a sequence selected from the group consisting of SEQ ID NO. 1, 2, 3, 4, 32, 33, 34, 35 and 36 or a fragment or variant thereof wherein the variant is at least 90% identical to said sequence selected from the group consisting of SEQ ID NO. 1, 2, 3, 4, 32, 33, 34, 35 and 36,
c) obtaining an amplicon,
d) analysing the length of the amplicon, and
e) discriminating between amplified Vel negative and Vel positive polynucleotide fragments based on polynucleotide length.

It is within the scope of the present invention to apply the above methods to any SMIM1 or SMIM1 related polynucleotide such as a polynucleotide being at least at least 50% identical to said SEQ ID NO. 1, 2, 3, 4, 32, 33, 34, 35 or 36, e.g. at least 55% identical to said SEQ ID NO. 1, 2, 3, 4, 32, 33, 34, 35 or 36 e.g. at least 60% identical to said SEQ ID NO. 1, 2, 3, 4, 32, 33, 34, 35 or 36, e.g. at least 65% identical to said SEQ ID NO. 1, 2, 3, 4, 32, 33, 34, 35 or 36, e.g. at least 70% identical to said SEQ ID NO. 1, 2, 3, 4, 32, 33, 34, 35 or 36, e.g. at least 75% identical to said SEQ ID NO. 1, 2, 3, 4, 32, 33, 34, 35 or 36, e.g. at least 80% identical to said SEQ ID NO. 1, 2, 3, 4, 32, 33, 34, 35 or 36, e.g. at least 81% identical to said SEQ ID NO. 1, 2, 3, 4, 32, 33, 34, 35 or 36, e.g. at least 82% identical to said SEQ ID NO. 1, 2, 3, 4, 32, 33, 34, 35 or 36, e.g. at least 83% identical to said SEQ ID NO. 1, 2, 3, 4, 32, 33, 34, 35 or 36, e.g. at least 84% identical to said SEQ ID NO. 1, 2, 3, 4, 32, 33, 34, 35 or 36, e.g. at least 85% identical to said SEQ ID NO. 1, 2, 3, 4, 32, 33, 34, 35 or 36, e.g. at least 86% identical to said SEQ ID NO. 1, 2, 3, 4, 32, 33, 34, 35 or 36, e.g. at least 87% identical to said SEQ ID NO. 1, 2, 3, 4, 32, 33, 34, 35 or 36, e.g. at least 88% identical to said SEQ ID NO. 1, 2, 3, 4, 32, 33, 34, 35 or 36, e.g. at least 89% identical to said SEQ ID NO. 1, 2, 3, 4, 32, 33, 34, 35 or 36, e.g. at least 90% identical to said SEQ ID NO. 1, 2, 3, 4, 32, 33, 34, 35 or 36, e.g. at least 91% identical to said SEQ ID NO. 1, 2, 3, 4, 32, 33, 34, 35 or 36, e.g. at least 92% identical to said SEQ ID NO. 1, 2, 3, 4, 32, 33, 34, 35 or 36, e.g. at least 93% identical to said SEQ ID NO. 1, 2, 3, 4, 32, 33, 34, 35 or 36, e.g. at least 94% identical to said SEQ ID NO. 1, 2, 3, 4, 32, 33, 34, 35 or 36, e.g. at least 95% identical to said SEQ ID NO. 1, 2, 3, 4, 32, 33, 34, 35 or 36, e.g. at least 96% identical to said SEQ ID NO. 1, 2, 3, 4, 32, 33, 34, 35 or 36, e.g. at least 97% identical to said SEQ ID NO. 1, 2, 3, 4, 32, 33, 34, 35 or 36, e.g. at least 98% identical to said SEQ ID NO. 1, 2, 3, 4, 32, 33, 34, 35 or 36, e.g. at least 99% identical to said SEQ ID NO. 1, 2, 3, 4, 32, 33, 34, 35 or 36 such as 100% identical to said SEQ ID NO. 1, 2, 3, 4, 32, 33, 34, 35 or 36.

It is also within the scope of the present invention to apply the above methods to any polynucleotide which is complementary to a SMIM1 or SMIM1-related polynucleotide such as a polynucleotide which is complementary to a polynucleotide which is at least 50% identical to said SEQ ID NO. 1, 2, 3, 4, 32, 33, 34, 35 or 36, e.g. a polynucleotide which is complementary to a polynucleotide which is at least 55% identical to said SEQ ID NO. 1, 2, 3, 4, 32, 33, 34, 35 or 36, e.g. a polynucleotide which is complementary to a polynucleotide which is at least at least 60% identical to said SEQ ID NO. 1, 2, 3, 4, 32, 33, 34, 35 or 36, e.g. a polynucleotide which is complementary to a polynucleotide which is at least at least 65% identical to said SEQ ID NO. 1, 2, 3, 4, 32, 33, 34, 35 or 36, e.g. a polynucleotide which is complementary to a polynucleotide which is at least at least 70% identical to said SEQ ID NO. 1, 2, 3, 4, 32, 33, 34, 35 or 36, e.g. a polynucleotide which is complementary to a polynucleotide which is at least at least 75% identical to said SEQ ID NO. 1, 2, 3, 4, 32, 33, 34, 35 or 36, e.g. a polynucleotide which is complementary to a polynucleotide which is at least at least 80% identical to said SEQ ID NO. 1, 2, 3, 4, 32, 33, 34, 35 or 36, e.g. a polynucleotide which is complementary to a polynucleotide which is at least at least 81% identical to said SEQ ID NO. 1, 2, 3, 4, 32, 33, 34, 35 or 36, e.g. a polynucleotide which is complementary to a polynucleotide which is at least at least 82% identical to said SEQ ID NO. 1, 2, 3, 4, 32, 33, 34, 35 or 36, e.g. a polynucleotide which is complementary to a polynucleotide which is at least at least 83% identical to said SEQ ID NO. 1, 2, 3, 4, 32, 33, 34, 35 or 36, e.g. a polynucleotide which is complementary to a polynucleotide which is at least at least 84% identical to said SEQ ID NO. 1, 2, 3, 4, 32, 33, 34, 35 or 36, e.g. a polynucleotide which is complementary to a polynucleotide which is at least at least 85% identical to said SEQ ID NO. 1, 2, 3, 4, 32, 33, 34, 35 or 36, e.g. a polynucleotide which is complementary to a polynucleotide which is at least at least 86% identical to said SEQ ID NO. 1, 2, 3, 4, 32, 33, 34, 35 or 36, e.g. a polynucleotide which is complementary to a polynucleotide which is at least at least 87% identical to said SEQ ID NO. 1, 2, 3, 4, 32, 33, 34, 35 or 36, e.g. a polynucleotide which is complementary to a polynucleotide which is at least at least 88% identical to said SEQ ID NO. 1, 2, 3, 4, 32, 33, 34, 35 or 36, e.g. a polynucleotide which is complementary to a polynucleotide which is at least at least 89% identical to said SEQ ID NO. 1, 2, 3, 4, 32, 33, 34, 35 or 36, e.g. a polynucleotide which is complementary to a polynucleotide which is at least at least 90% identical to said SEQ ID NO. 1, 2, 3, 4, 32, 33, 34, 35 or 36, e.g. a polynucleotide which is complementary to a polynucleotide which is at least at least 91% identical to said SEQ ID NO. 1, 2, 3, 4, 32, 33, 34, 35 or 36, e.g. a polynucleotide which is complementary to a polynucleotide which is at least at least 92% identical to said SEQ ID NO. 1, 2, 3, 4, 32, 33, 34, 35 or 36, e.g. a polynucleotide which is complementary to a polynucleotide which is at least at least 93% identical to said SEQ ID NO. 1, 2, 3, 4, 32, 33, 34, 35 or 36, e.g. a polynucleotide which is complementary to a polynucleotide which is at least at least 94% identical to said SEQ ID NO. 1, 2, 3, 4, 32, 33, 34, 35 or 36, e.g. a polynucleotide which is complementary to a polynucleotide which is at least at least 95% identical to said SEQ ID NO. 1, 2, 3, 4, 32, 33, 34, 35 or 36, e.g. a polynucleotide which is complementary to a polynucleotide which is at least at least 96% identical to said SEQ ID NO. 1, 2, 3, 4, 32, 33, 34, 35 or 36, e.g. a polynucleotide which is complementary to a polynucleotide which is at least at least 97% identical to said SEQ ID NO. 1, 2, 3, 4, 32, 33, 34, 35 or 36, e.g. a polynucleotide which is complementary to a polynucleotide which is at least at least 98% identical to said SEQ ID NO. 1, 2, 3, 4, 32, 33, 34, 35 or 36, e.g. a polynucleotide which is complementary to a polynucleotide which is at least at least 99% identical to said SEQ ID NO. 1, 2, 3, 4, 32, 33, 34, 35 or 36, e.g. a polynucleotide which is complementary to a polynucleotide which has a sequence selected from the group consisting of SEQ ID NO. 1, 2, 3, 4, 32, 33, 34, 35 and 36.

The method of discriminating between Vel negative and Vel positive individuals as outlined above can utilise any suitable tool or method known in the art which tool or method is suitable for analysing biomolecules such as DNA, RNA and proteins. In one embodiment of the present invention, the method used for analysing SMIM1 composition of an individual or a sample is carried out by a process which may be selected from the group consisting of: gene specific PCR, allele specific PCR, PCR-RFLP, allele-specific probe hybridization, allele-specific primer extension, allele-specific amplification, sequencing, 5' nuclease digestion, molecular beacon assay, oligonucleotide ligation assay, size analysis, and single-stranded conformation polymorphism.

In one embodiment the method for discriminating Vel positive and Vel negative samples or individuals is gene specific PCR.

In one embodiment the gene specific PCR method comprises the steps of:

i) providing a biological sample,
ii) amplifying a SMIM1 polynucleotide by applying a first and a second oligonucleotide primer, thus obtaining an amplicon,
iii) performing qualitative and/or quantitative analysis of the SMIM1 amplicon obtained in step ii), and
iv) comparing the length of the amplicon, to at least one Vel positive control, wherein a length differing from the Vel positive control indicates that the sample is from a Vel negative subject.

Any suitable oligonucleotide primer pairs capable of hybridizing with the target polynucleotide are within the scope of the present invention.

In one embodiment, the first oligonucleotide primer is at least 80%, preferably at least 90%, more preferably at least 95%, more preferably at least 96%, more preferably at least 97% identical, more preferably at least 98% identical, more preferably at least 99%, more preferably at least 100% identical to SEQ ID NO: 22 (LOCex3f_screen), and the second oligonucleotide primer is at least 80%, preferably at least 90%, more preferably at least 95%, more preferably at least 96%, more preferably at least 97% identical, more preferably at least 98% identical, more preferably at least 99%, more preferably at least 100% identical to SEQ ID NO: 23 (LOCex3r_screen). Under high stringency hybridization conditions, said first and said second oligonucleotide primer are capable of hybridizing to said SMIM1 polynucleotide.

In another embodiment the method for discriminating Vel positive and Vel negative samples or individuals is by allele specific PCR.

In one embodiment the allele specific PCR method comprises the steps of:

i) providing a biological sample,
ii) amplifying a SMIM1 polynucleotide by applying a first and a second oligonucleotide primer, thus obtaining an amplicon,
iii) performing qualitative and/or quantitative analysis of the SMIM1 amplicon obtained in step ii), and
iv) comparing the length of the amplicon, to at least one Vel positive control, wherein a length differing from the Vel positive control indicates that the sample is from a Vel negative subject.

In one embodiment, the oligonucleotide primers of the above allele specific PCR method, are selected from the group consisting of oligonucleotide primers being at least 80%, preferably at least 90%, more preferably at least 95%, more preferably at least 96%, more preferably at least 97% identical, more preferably at least 98% identical, more preferably at least 99%, more preferably at least 100% identical to SEQ ID NO: 15 (388588int2f), SEQ ID NO: 19 (388588int3R2), SEQ ID NO. 20 (388588wtex3f) and SEQ ID NO. 21 (388588mutex3f), wherein, under high stringency hybridization conditions, said oligonucleotide primers are capable of hybridizing to said SMIM1 polynucleotide.

In another embodiment the method for discriminating Vel negative from Vel positive samples or individuals is by allele PCR-RFLP.

In one embodiment the gene specific PCR-RFLP method comprises the steps of i) amplifying a SMIM1 polynucleotide by applying at least two oligonucleotide primers,
ii) digesting the amplicon of step i) by a restriction enzyme, iii) performing qualitative and/or quantitative analysis of the digested amplicon of step ii), and iv) comparing the length of the digested amplicon(s), to at least one Vel positive control, wherein a length differing from the Vel positive control indicates that the sample is from a Vel negative subject.

Any suitable restriction may be used. In one embodiment the restriction enzyme is StyI.

In one embodiment, the oligonucleotide primers of the above PCR-RFLP method, the first oligonucleotide primer is at least 80%, preferably at least 90%, more preferably at least 95%, more preferably at least 96%, more preferably at least 97% identical, more preferably at least 98% identical, more preferably at least 99%, more preferably at least 100% identical to SEQ ID NO: 15 (388588int2f), and the second oligonucleotide primer is at least 80%, preferably at least 90%, more preferably at least 95%, more preferably at least 96%, more preferably at least 97% identical, more preferably at least 98% identical, more preferably at least 99%, more preferably at least 100% identical to SEQ ID NO: 19 (388588int3R2), wherein under high stringency hybridization conditions, said first and said second oligonucleotide primer are capable of hybridizing to said SMIM1 polynucleotide.

As mentioned herein above, the method of the present invention is based on molecular discrimination between Vel negative and Vel positive individuals or samples from such individuals. Thus, in one embodiment the method of the present invention comprises the steps:

i) providing a biological sample comprising genomic DNA, ii) contacting the sample comprising genomic DNA with a first and a second PCR oligonucleotide primer, wherein said first primer comprises at least 10 nucleotides being complementary to at least 10 consecutive nucleotides selected from the sequence identified as SEQ ID NO. 1 and located upstream (5') of nucleotide position 2667 of SEQ ID NO. 1, and wherein said second primer comprises at least 10 nucleotides being complementary to at least 10 consecutive nucleotides selected from the sequence identified as SEQ ID NO: 1 and located downstream (3') of nucleotide position 2649 of SEQ ID NO. 1, with the proviso that said first and said second primer are not both selected from a sequence being complementary to SEQ ID NO. 31;

iii) obtaining an amplicon;

iv) performing qualitative and/or quantitative analysis of the amplicon of step iii);

v) comparing the length of the amplicon, to at least one Vel positive control, wherein a length differing from the Vel positive control indicates that the sample is Vel negative.

The qualitative and/or quantitative analysis performed in the method of the present invention can be made by any suitable tool or method known by those of skill in the art. In one embodiment the qualitative and/or quantitative analysis is performed by gel electrophoresis.

The reference control used in the method of the present invention may be any suitable molecular marker, such as a molecular marker based on Mw. In one embodiment of the present invention, the reference control is a polynucleotide reference composition comprising one or more polynucleotides selected from polynucleotides consisting of 161 and 178 nucleotides. In one embodiment the Vel positive control is a polynucleotide comprising exon 3 (SEQ ID NO. 30) of SMIM1.

It is an object of the present invention to amplify a part of the SMIM1 gene of a Vel negative individual, which part comprises a non-sense mutation leading to a non-functional Vel antigen. This means that the size of the amplicon may vary depending on how the oligonucleotide primers are selected. In one embodiment the amplified genetic material (amplicon) is between about 5 and about 4000 nucleotides in length, such as between 10 and 100 nucleotides in length, e.g. 17 nucleotides in length.

In one aspect, the present invention concerns a method of detection and/or quantitation of a splice variant of SMIM1 in a sample, the method comprising making complementary DNA (cDNA) from messenger RNA (mRNA) in the sample, amplifying the entire or portions of the cDNA corresponding to the SMIM1 gene, such as SEQ ID NO. 3 or 4, or parts thereof and detecting and quantifying the amplified cDNA in order to detect or quantify the splice variant.

In one aspect, the invention concerns a method of identifying a subject presenting a Vel antigen, comprising the steps:

a) performing amplification of a polynucleotide of the subject by contacting a polynucleotide from a cell of the subject with an oligonucleotide primer having a sequence being complementary to at least 10 consecutive nucleotides of a polynucleotide encoding the Vel antigen;

b) detecting an amplicon from step (a), whereby the detection of an amplicon identifies the subject as a Vel antigen.

In another aspect the present invention concerns a method of detecting in a sample, a cell that expresses a Vel antigen, comprising detection in the sample of a polynucleotide that encodes a Vel antigen.

In one embodiment the method of detection and/or quantitation of a splice variant of SMIM1 in a sample, comprises making complementary DNA (cDNA) from messenger RNA(mRNA) in the sample, amplifying portions of the cDNA corresponding to the SMIM1 gene or parts thereof and detecting and quantifying the amplified cDNA in order to detect or quantify the splice variant.

The present inventors have generated data which further characterizes the protein encoded by the SMIM1 (LOC388588) gene as well as the demographic distribution of the mutation causing the Vel negative phenotype. Thus far, no gene homologues to the human Vel protein have been found. However, the gene appears to be evolutionarily conserved as it has orthologous homologues in other species, from primates to zebrafish.

The SMIM1 gene which typically comprises SEQ ID NO. 1 or a fragment or sequence variant thereof, encodes a polypeptide which is associated with the Vel antigen. Expression of the Vel blood group antigen on red blood cells is dependent on expression of the SMIM1 gene, the mRNA of which encodes a type 1 transmembrane protein. The Vel-negative phenotype occurs when this protein cannot be expressed, for instance due to the 17-bp deletion. While a main aspect of the present invention is to avoid laborious and expensive traditional serological methods for identifying Vel negative samples or individuals, the findings of the present inventors of the connection between SMIM1 and the Vel antigen provides a number of antibody and cell based applications which are useful for e.g. in vitro testing purposes.

The method according to the present invention can in principle be applied to any biological sample comprising genetic material. Thus the sample may be from cell scrapings, a biopsy tissue or a body fluid such as, but not limited to blood, bone marrow, plasma, serum, cerebrospinal fluid, saliva, sperm, sputum, urine and stool.

Vel Antigen and Anti-Vel Antibodies

The present inventors have provided the molecular nexus between the SMIM1 gene and the Vel antigen.

Following this discovery, the inventors have also designed and tested peptides corresponding to the putative protein and tested Vel positive and Vel negative RBCs with rabbit antibodies raised to these peptides. One such antibody demonstrates exquisite specificity for Vel positive RBCs by Western blotting technique.

In one embodiment, the antibody being detected by said method is anti-Vel, and the antigen is a peptide selected from the group consisting of SEQ ID NO. 5, 6, 7, 8, 9 and 10.

The Vel antigen identified by the present inventors is represented by the polypeptide having SEQ ID NO. 5, or a sequence variant or fragment thereof. The antigen is a useful tool in the methods of the present invention. Accordingly in one aspect, the present invention concerns an isolated polypeptide having the sequence of SEQ ID NO. 5, or a fragment or a variant thereof, wherein said fragment comprises at least 20, such as at least 25, such as at least 30, such as at least 35, such as at least 40, such as at least 45, such as at least 50, such as at least 55, such as at least 60, such as at least 65, such as at least 70, such as at least 75 consecutive amino acid residues of SEQ ID NO. 5, and wherein said variant is at least 80% identical to SEQ ID NO. 5, and wherein said variant comprises at least one Serine and/or Threonine residue, and wherein at least one Serine and/or Threonine residue of said SEQ ID NO. 5 or said fragment or variant thereof, is O-glycosylated.

Expression of the Vel blood group antigen on red blood cells is dependent on expression of the SMIM1 gene, the mRNA of which encodes a type 1 transmembrane protein. The Vel-negative phenotype occurs when this protein cannot be expressed, for instance due to the 17-bp deletion as discussed herein above. Important polypeptide fragments associated with the Vel antigen include fragments of SEQ ID NO. 5. Thus in one aspect, the present invention concerns an isolated peptide having a sequence selected from the group consisting of SEQ ID NOs. 6, 7, 8, 9 and 10, or a fragment or variant thereof, wherein the variant is at least 50%, preferably at least 55%, preferably at least 60%, preferably at least 65%, preferably at least 70%, preferably at least 75%, preferably at least 80%, preferably at least 81%, preferably at least 82%, preferably at least 83%, preferably at least 84%, preferably at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, preferably at least 96%, preferably at least 97%, preferably at least 98%, preferably at least 99% identical to a sequence selected from the group consisting of SEQ ID NOs. 6, 7, 8, 9 and 10.

In one aspect the present invention concerns a homodimer comprising two identical polypeptide chains, each having the sequence of SEQ ID NO. 5, or a fragment or a variant thereof, wherein said fragment comprises at least 20 consecutive amino acid residues of SEQ ID NO. 5, and wherein said variant is at least 80%, preferably at least 81%, preferably at least 82%, preferably at least 83%, preferably at least 84%, preferably at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, preferably at least 96%, preferably at least 97%, preferably at least 98%, preferably at least 99% identical to identical to SEQ ID NO. 5.

In one embodiment the polypeptide fragment defining the Vel antigen is an isolated polynucleotide, encoding upon expression a peptide having a sequence selected from the group consisting of SEQ ID NOs. 6, 7, 8, 9 and 10 is also an aspect of the present invention.

The antigen may under certain circumstances be glycosylated, typically O-glycosylated on a Serine or Threonine residue. Thus in one aspect, the present invention concern an isolated polypeptide having the sequence of SEQ ID NO. 5, or a fragment or a variant thereof, wherein said fragment comprises at least 20 consecutive amino acid residues of SEQ ID NO. 5, and wherein said variant is at least 80% identical, preferably at least 81%, preferably at least 82%, preferably at least 83%, preferably at least 84%, preferably at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, preferably at least 96%, preferably at least 97%, preferably at least 98%, preferably at least 99% identical to SEQ ID NO. 5, and wherein said variant comprises at least one Serine and/or Threonine residue, and wherein at least one Serine and/or Threonine residue of said SEQ ID NO. 5 or said fragment or variant thereof, is O-glycosylated.

In one embodiment at least one Serine and/or Threonine residue of the above polypeptide is O-glycosylated.

In a further embodiment the O-glycosylation of the at least one Serine and/or Threonine residue is individually and independently selected from the group consisting of:

Tn antigen (GalNAcαSer/Thr),
Sialyl-Tn antigen (Siaα2-6GalNAcαSer/Thr),
STn/sialyl-Tn (Neu5Acα2-6GalNAc-α-Ser/Thr),
ST/sialyl-T (Neu5Acα2-3GalβGalNAc-Ser/Thr),
Core 1 or T antigen (Galβ1-3GalNAcαSer/Thr),
Core 2 (GlcNAcβ1-6(Galβ1-3)GalNAcαSer/Thr),
Core 3 (GlcNAcβ1-3GalNAcαSer/Thr),
Core 4 (GlcNAcβ1-6(GlcNAcβ1-3)GalNAcαSer/Thr),
Core 5 (GalNAcα1-3GalNAcαSer/Thr),
Core 6 (GlcNAcβ1-6GalNAcαSer/Thr),
Core 7 (GalNAcα1-6GalNAcαSer/Thr), and
Core 8 (Galα1-3GalNAcαSer/Thr).

As mentioned herein above, it is a main aspect of the present invention to provide tools and methods for genetically based bloodgrouping of the Vel blood group. Tools for such purposes include antibodies, antigens and antigen fragments as well as cells presenting said antigens or antigen fragments.

Accordingly, in one such aspect, the present invention concerns a method of detecting in a sample an antibody directed to a Vel antigen, comprising the steps:

a) contacting red blood cells having a Vel antigen with the sample;

b) detecting agglutination of the red blood cells, whereby agglutination of the red blood cells indicates the presence in the sample of an antibody to a Vel antigen.

In another aspect, the present invention concerns a method of detecting in a sample an antibody directed to a Vel antigen, comprising the steps:

a) contacting a sample with a peptide or polypeptide selected from the group consisting of SEQ ID NOs. 5, 6, 7, 8, 9 and 10, or an O-glycosylated peptide sequence selected from SEQ ID NOs. 5, 6, 7, 8, 9 and 10;

b) detecting interaction between i) said polypeptide or peptide and ii) an anti-Vel antibody, whereby interaction indicates the presence in the sample of an antibody to a Vel antigen.

In one embodiment the interaction is detected by studying agglutination. In another embodiment the interaction is detected by BIACORE. In another embodiment the interaction is detected by ELISA based methods. All of the above methods of detecting interaction are well known by those of skill in the art.

In another aspect, the present invention concerns a method of detecting a Vel antigen on red blood cells, comprising the steps:

a) contacting the red blood cells with an antibody directed to the Vel antigen;

b) detecting agglutination of the red blood cells, whereby agglutination of the red blood cells indicates the presence of the Vel antigen.

In another aspect the present invention concerns a method of detecting in a sample a Vel antigen, comprising the steps:

a) contacting the sample with an antibody directed to a Vel antigen;

b) detecting an antigen/antibody complex, whereby detection of the antigen/antibody complex indicates the presence of the Vel antigen in the sample.

In another aspect the present invention concerns a method of identifying a subject presenting a Vel antigen, comprising the steps:

a) performing amplification of a polynucleotide of the subject by contacting a polynucleotide from a cell of the subject with an oligonucleotide primer having a sequence being complementary to at least 10 consecutive nucleotides of a polynucleotide encoding the Vel antigen;

b) detecting an amplicon from step (a), whereby the detection of an amplicon identifies the subject as a Vel antigen.

In yet another aspect the present invention concerns a method of detecting in a sample, a cell that expresses a Vel antigen comprising detecting in the sample a polynucleotide that encodes a Vel antigen.

It is also within the scope of the present invention to provide antibodies for in vitro testing as well as verification of the genetic methods outlined above. Thus in one aspect the present invention concerns an antibody capable of recognising an epitope of a Vel antigen, wherein the epitope is defined by a peptide sequence selected from the group consisting of SEQ ID NOs. 6, 7, 8, 9 and 10, or an O-glycosylated peptide sequence selected from SEQ ID NOs. 6, 7, 8, 9 and 10.

In one embodiment the antibody is capable of recognising an O-glycosylated peptide sequence selected from SEQ ID NOs. 6, 7, 8, 9 and 10 which comprises at least one Serine and/or Threonine residue wherein the at least one Serine and/or Threonine residue individually and independently is O-glycosylated with a glycan selected from the group consisting of:

Tn antigen (GalNAcαSer/Thr),
Sialyl-Tn antigen (Siaα2-6GalNAcαSer/Thr),
STn/sialyl-Tn (Neu5Acα2-6GalNAc-α-Ser/Thr),
ST/sialyl-T (Neu5Acα2-3Gal 3GalNAc-Ser/Thr),
Core 1 or T antigen (Galβ1-3GalNAcαSer/Thr),
Core 2 (GlcNAcβ1-6(Galβ1-3)GalNAcαSer/Thr),
Core 3 (GlcNAcβ1-3GalNAcαSer/Thr),
Core 4 (GlcNAcβ1-6(GlcNAcα1-3)GalNAcαSer/Thr),
Core 5 (GalNAcα1-3GalNAcαSer/Thr),
Core 6 (GlcNAcβ1-6GalNAcαSer/Thr),
Core 7 (GalNAcα1-6GalNAcαSer/Thr), and
Core 8 (Galα1-3GalNAcαSer/Thr).

The antibody is either monoclonal or polyclonal.

The present invention also concerns a method of making a polyclonal antibody, the method comprising:

a) immunizing a mammal with the polypeptide or peptide as defined herein above, under conditions to elicit an antibody response;

b) isolating mammal antibodies;

c) screening the isolated antibodies with the polypeptide or polypeptide fragment thereby identifying a polyclonal antibody that binds specifically to the polypeptide or polypeptide fragment of step a).

The present invention also concerns a method of making a monoclonal antibody, the method comprising:

a) immunizing a mammal with the polypeptide or peptide as defined herein above, under conditions to elicit an antibody response;

b) isolating antibody producing cells from the mammal;

c) fusing the antibody producing cells with immortalized cells in culture to form monoclonal antibody-producing hybridoma cells;

d) culturing the hybridoma cells;

e) isolating from the culture monoclonal antibodies which bind specifically to the polypeptide or polypeptide fragment of step a).

Blood Transfusion

The method of the present invention is particularly useful in a clinical setting involving blood transfusions. Thus in one embodiment the above methods further comprises the steps of:

a) electing from a donor or blood bank i) Vel positive blood if the method of a) determines that the patient is Vel positive, or ii) Vel negative blood if the method as defined herein above determines that the patient is Vel negative;

b) transfusing the patient with the blood elected in a).

In one aspect the present invention concerns a blood transfusion method comprising the steps:

a) applying the method as defined herein above to a patient;

b) electing from a donor or blood bank i) Vel positive blood if the method of a) determines that the patient is Vel positive, or ii) Vel negative blood if the method of a) determines that the patient is Vel negative;

c) transfusing the patient with the blood elected in b).

Blood transfusions are useful in the treatment of blood disorders. The present invention is particularly useful during therapy in relation to treatment of a disease or disorder associated with erythrocytes wherein the invention concerns a method comprising the steps:

a) applying the detection/identification method defined herein above to a patient;

b) electing from a donor or blood bank i) Vel positive if the method of a) determines that the patient is Vel positive, or ii) Vel negative blood if the method of a) determines that the patient is Vel negative;

c) transfusing the patient with the blood elected in b).

Prophylactic Treatment of Pregnant Female Individuals

Pregnant Vel negative females (mother) may carry Vel positive foetuses. If erythrocytes from the Vel positive foetus is transferred to the Vel negative mother, this may result in an immune response of the mother thus raising anti-Vel antibodies against the Vel positive erythrocytes. This is potentially lethal for the foetus, especially during a second or subsequent pregnancy of the Vel negative female.

Accordingly, in one aspect the present invention concerns a method of prophylactic treatment of a Vel negative pregnant female individual comprising:

a) identifying a Vel negative individual by applying the method as defined herein above, and b) administering to said Vel negative pregnant female individual a therapeutically effective amount of an anti-Vel antibody, thus neutralizing Vel positive erythrocytes originating from the a Vel positive foetus carried by said Vel negative pregnant female individual.

Similarly, the present invention also concerns an anti-Vel antibody for use in a method of prophylactic treatment of a Vel negative pregnant female individual comprising:

a) identifying a Vel negative individual by applying the method as defined herein above, and b) administering to said Vel negative pregnant female individual the anti-Vel antibody, thus neutralizing Vel positive erythrocytes originating from the a Vel positive foetus carried by said Vel negative pregnant female individual.

Screening Platforms

The primary use of the present invention is in the field of transfusion medicine where described nucleotide deletion will be used as a basis for screening of blood donors in order to identify compatible blood for patients who have developed antibodies to the Vel antigen. High throughput genotyping platforms for donor testing exist in the routine laboratory today and thus in one embodiment the present invention is incorporated into these platforms.

Accordingly in one aspect the present invention concerns a kit for detecting a Vel antigen, or discriminating between Vel negative and Vel positive samples, wherein said kit comprises the antibody as defined herein above. The kit typically comprises a microchip array wherein the antibodies defined above are conjugated to the microchip array.

In one aspect the present invention concerns a kit for detecting a Vel antigen and/or discriminating between samples from Vel negative and Vel positive individuals, said kit comprising at least two isolated oligonucleotide primers selected from the group consisting of SEQ ID NO. 11, 12, 13, 14, 15, 16, 17, 18, 19, 20, 21, 22 and 23.

In another aspect the invention concerns a kit comprising a microchip array comprising one or more polynucleotides selected from the group consisting of SEQ ID NO. 1, 2, 3, 4, 11, 12, 13, 14, 15, 16, 17, 18, 19, 20, 21, 22, 23, 32, 33, 34, 35 and 36 or one or more fragments of said polynucleotide.

The kit including or excluding the microchip array may include a combination of one or more of polynucleotides, oligonucleotides, peptides and polypeptides defined herein.

In one aspect, the present invention concerns a kit comprising a microchip array comprising one or more peptides or polypeptides selected from the group consisting of SEQ ID NO. 5, 6, 7, 8, 9 and 10, or one or more fragments of said peptide or polypeptide wherein said fragment comprises at least 5 consecutive amino acids of said SEQ ID NO. 5, 6, 7, 8, 9 and 10.

In one embodiment of the kit defined herein above at least one Serine and/or Threonine residue of said peptide in said kit is O-glycosylated, such wherein at least one of said Serine and/or Threonine residue is independently and optionally O-glycosylated by a glycan selected from the group consisting of Tn antigen (GalNAcαSer/Thr),
Sialyl-Tn antigen (Siaα2-6GalNAcαSer/Thr),
STn/sialyl-Tn (Neu5Acα2-6GalNAc-α-Ser/Thr),
ST/sialyl-T (Neu5Acα2-3Galβ3GalNAc-Ser/Thr),
Core 1 or T antigen (Galβ1-3GalNAcαSer/Thr),
Core 2 (GlcNAcβ1-6(Galβ1-3)GalNAcαSer/Thr),
Core 3 (GlcNAcβ1-3GalNAcαSer/Thr),
Core 4 (GlcNAcβ1-6(GlcNAcβ1-3)GalNAcαSer/Thr),
Core 5 (GalNAcα1-3GalNAcαSer/Thr),
Core 6 (GlcNAcβ1-6GalNAcαSer/Thr),
Core 7 (GalNAcα1-6GalNAcαSer/Thr), and
Core 8 (Galα1-3GalNAcαSer/Thr).

In one aspect, the kit described herein above comprises red blood cells presenting a Vel antigen.

In certain aspects the invention concerns the following embodiments.

Embodiment 1

A method of determining the Vel phenotype of an individual, said method comprising discriminating between Vel positive and Vel negative phenotypes by analysing in a biological sample the composition of a) a SMIM1 gene, and/or
b) a transcript of a SMIM1 gene, and/or
c) a polypeptide encoded by a SMIM1 gene.

Embodiment 2

The method according to embodiment 1, wherein the SMIM1 gene comprises the sequence of SEQ ID NO: 1 or a sequence variant thereof wherein the sequence variant is between at least 60%, such as at least 70%, such as at least 80%, such as at least 90%, such as at least 95%, such as at least 96%, such as at least 97%, such as at least 98%, such as at least 99%, such as between 99.1 and 99.9%, between 99.4 and 99.6%, such as 100% identical to i) SEQ ID NO. 1 or ii) a sequence being complementary to SEQ ID NO. 1.

Embodiment 3

The method according to any one of the preceding embodiments, wherein the discrimination by analysing the SMIM1 composition comprises identifying:

subjects whose genome comprises SEQ ID NO. 1, said subjects being Vel positive, and subjects whose genome comprises SEQ ID NO. 2, or a fragment or variant thereof, wherein the variant is at least 90% identical to said SEQ ID NO. 2, said subjects being Vel negative.

Embodiment 4

The method according to embodiment 1, wherein the method comprises:

a) providing a biological sample comprising a SMIM1 polynucleotide,
b) amplifying at least a fragment of the SMIM1 polynucleotide, wherein the SMIM1 polynucleotide has a sequence selected from the group consisting of SEQ ID NO. 1, 2, 3, 4, 32, 33, 34, 35 and 36 or a fragment or variant thereof wherein the variant is at least 90% identical to said sequence selected from the group consisting of SEQ ID NO. 1, 2, 3, 4, 32, 33, 34, 35 and 36;
c) obtaining an amplicon,
d) analysing the length of the amplicon, and
e) discriminating between amplified Vel negative and Vel positive polynucleotide fragments based on polynucleotide length.

Embodiment 5

The method according to embodiment 1 comprising the steps:

i) providing a biological sample comprising genomic DNA, ii) contacting the sample comprising genomic DNA with a first and a second PCR oligonucleotide primer,
   wherein said first primer comprises at least 10 nucleotides being complementary to at least 10 consecutive nucleotides selected from the sequence identified as SEQ ID NO. 1 and located upstream (5') of nucleotide position 2667 of SEQ ID NO. 1, and
   wherein said second primer comprises at least 10 nucleotides being complementary to at least 10 consecutive nucleotides selected from the sequence identified as SEQ ID NO: 1 and located downstream (3') of nucleotide position 2649 of SEQ ID NO. 1,
   with the proviso that said first and said second primer are not both selected from a sequence being complementary to SEQ ID NO. 31;

iii) obtaining an amplicon;

iv) performing qualitative and/or quantitative analysis of the amplicon of step iii).

Embodiment 6

A method of detection and/or quantitation of a splice variant of SMIM1 in a sample, the method comprising making complementary DNA (cDNA) from messenger RNA (mRNA) in the sample, amplifying portions of the cDNA corresponding to the SMIM1 gene or parts thereof and detecting and quantifying the amplified cDNA in order to detect or quantify the splice variant.

Embodiment 7

An isolated polynucleotide comprising a sequence variant of SEQ ID NO. 1, or an isolated polynucleotide comprising a sequence variant of a sequence being complementary to said SEQ ID NO. 1, wherein the sequence variant comprises at least one mutation, wherein mutation results in abolished transcription and/or protein translation and/or absence of a polypeptide encoded by SEQ ID NO. 1 on the surface of an erythrocyte.

Embodiment 8

The isolated polynucleotide according to embodiment 7, wherein the sequence variant has the sequence selected from the group consisting of SEQ ID NO. 2 and 4.

Embodiment 9

An isolated polypeptide having the sequence of SEQ ID NO. 5, or a fragment or a variant thereof, wherein said fragment comprises at least 20 consecutive amino acid residues of SEQ ID NO. 5, and wherein said variant is at least 80% identical to SEQ ID NO. 5, and wherein said variant comprises at least one Serine and/or Threonine residue, and wherein at least one Serine and/or Threonine residue of said SEQ ID NO. 5 or said fragment or variant thereof, is O-glycosylated.

Embodiment 10

An isolated peptide having a sequence selected from the group consisting of SEQ ID NOs. 6, 7, 8, 9 and 10.

EXAMPLES

Example 1: Sequences

```
SEQ ID NO. 1: SMIM1 gene
   1     (cagagacgcg gggacacag)g tgaggcgcgc ggggtccggg ctgcggcttc ccggtgcggc

  61     cgcagtgggc aggtgcgact gtgcgcggcc tcgctggctg agaactggcg ggggtggggg

 121     cgtgccctgg actgaccccc accggcctaa cccgcggtgc ggggccaggg ccggaactgc

 181     ccgcccggct ccttgcccgg ctccttgtgg ctgctgggga cccccgacac cagccacttt

 241     cccttcccgg cccttagcaa gatcggcttc tccggtcacc tttatttttt tag(gctcgag

 301     gcgtctgccg cacctcagcc cacgacctgc cccgctggga ggtgcgggcc gctggccagg

 361     ccctgaccgc aacctggccc agaggcccca gccctcaggc aaggttctcc gg)gtaagtgt

 421     ggggccctga ggcgctgtgg ggtgaagagg tctatggagg ggcgcctgtg tacctagggc

 481     cttcctgcac tcacaagccc ccaggaggtg ccaggatccg ggagcctccc agggcctgga

 541     ggggagtccc tgatgggttc ctgccgccac acctgtgacc atcacatgag tgtggagaga

 601     cgtttactga gcaagtgagg gaggccagcc tcaagggccg gctctggtgg ctgtgcaccg

 661     gggtgacttg ggaacaacgt gttctacgtc agcaagacag gaacccatga tcccagagtt

 721     gaacacactg ggcttgaccc ctcccaccgg gaggcccatg gtgggctgct gctgtggact

 781     tggagcctca gcactcccga gactaatgct gcgtggatgt cgggttgcaa ggcggctgct

 841     gcagctccag cagctccagc catcacgtcg agtctggaag aaggaggtgg ctgctgctgc

 901     tttcacagaa gcaaactctc ccatcccctg ctgcaccctg gctcctggac cccagctggg

 961     tgacttggga aagcaggggt ggtggtatta agcttgtctt acccgggtca tggctgttac

1021     ctggggctgg cacattgctg ctgggaccag aatgggattc tgcacaccag gcaagagggc

1081     gtgaacctcg ggtaggcagc tgaccgctcc acatgctccg ggaaaacagc acccatactc
```

-continued 1141 cagtagaggc tgggcctctc cgggcctgag tgccaggctg cactgagcca gggctcccac 1201 cgaaggcaca ctttatggct ttgagacagc tccttctgcc tctctgggct ttgggggaag 1261 gcagacatgg aagtgccggg agtctcagaa ctgcctgggg cctgagtttc tgagctggct 1321 tcttgcaggg gagtggctgc tgtgccttta ggcctctgtg ccgatgacct gggaggaagg 1381 tcagccttcc ccgctggagg gggcccagca aagcctcagc tcctagaagt gaggggcctg 1441 ccattgcctg cccgaggacc ccactcctgg gggccagatg ctgagagggg acactggggg 1501 cccagcagac cagagagctg accccagtcc cacagcctgg gtgggttgtc aacttctcgt 1561 gccccctcca actcctccac ccccacaccc ccttaggtaa ataggaggtc gaaacagagg 1621 ccagagggta aaggaggtgc ttagagtccg ggctggctca ggccggccgg gcagctgtgc 1681 tagtgcttgg agttcctgct cagtccccgt ggtctcctcg cccctctggg cacttgggct 1741 gccaggcacc gagctgagtg ccgagatgca aagatgagtc ccaggtctgc aggagttgga 1801 gcccagcagg gagctggcct tggggccggg cccctcctgc tctgggcagc cacccagccc 1861 tacgaccctc ctgtctctgt agggcctccc caaggccttg aatccacccc ggccccgtgc 1921 tcagtgcatc atgcccccca agccccagcc ctcctagagg tgtgggtggg ggaggggctg 1981 caacccacac aggctgagga cacagctgct gccactgcct ggggccagcc acgcatcctc 2041 cccagacagg gaccggtcta gctgtaccag ccgctgcccc ggacctgctg ccctgcccca 2101 cccccccctc ccctggccag cctccccaga ggccagaagg cgccttatcg ggcagggtta 2161 aggaggggga cagttatcag gggctgcagc ctagattggg ccacaatgtc ctcgtctctt 2221 gagggtggca ggctgtgcag gctccctgat aaaagcaccg gggaagggag gctcctggag 2281 tgtgctggaa ggaaacactg gcctcccaca tgcctgaggt cagggcttgg cctgagatgg 2341 aattctcgct tggtcccatc ctcccggcct gaccctgggc aaatgactct accactttgt 2401 gtctaggtca cctgttaagt caggcgacag acccggtgag ggagtcagcc cccgaccctt 2461 agtgcccctc tcctaacagc agcctcagag gggtcttgga ctgccgccct ccatccgctt 2521 gttttacag(t gaagccacag cctggccacc tgtcttgatc tccccaccga gaaggccccg 2581 cccctcccgc tgcagcccca cagcatgcag ccccaggaga gccacgtcca ctatagtagg 2641 tgggaggacg gcagcaggga cggagtc*agc ctaggggctg tgtc*cagcac agaagaggcc 2701 tcacgctgcc gcag)gtgagg ggcctgaggg cagcctgcca gccatagcag gctggtgtct 2761 ccctccagag acgcctgccc taacccctgc taccggcccc atcaccctcc accccatcct 2821 ggctgggagc ccacggtcca gcagctcagc aaaccgcagc ctttggcctt ccctctggtt 2881 ggctgtgggc ggggagagct tcctct*tg*ac tccagcagag cgcccaggcc cctcccccctg 2941 acccagacca acggccacag tccacttagg gggcccctca tgcggccctg gcctggggct 3001 cacctccagt tggttctcac cccag(gatct cccagaggct gtgcacgggc aagctgggca 3061 tcgccatgaa ggtgctgggc ggcgtggccc tcttctggat catcttcatc ctgggctacc 3121 tcacaggcta ctatgtgcac aagtgcaaat aaatgctgcc ccgcatgcac gcggggggct 3181 ggccgca)

Portions within parentheses indicate exons; underline indicates the start and stop codons; bold italics indicates the 17 bp deletion identified in the mutant phenotype in exon 3 and also the polymorphic nucleotides in intron 3 (c.110+193t/c and c.110+194g/a; nucleotides 2907 & 2908 in the sequence above) both of which are invariantly mutated in the mutant phenotype.

SEQ ID NO. 2: SMIM1-mutant phenotype (17 bp deletion)

1 (cagagacgcg gggacacag)g tgaggcgcgc ggggtccggg ctgcggcttc ccggtgcggc

-continued

```
61    cgcagtgggc aggtgcgact gtgcgcggcc tcgctggctg agaactggcg ggggtggggg
121   cgtgccctgg actgaccccc accggcctaa cccgcggtgc ggggccaggg ccggaactgc
181   ccgcccggct ccttgcccgg ctccttgtgg ctgctgggga cccccgacac cagccacttt
241   cccttcccgg cccttagcaa gatcggcttc tccggtcacc tttatttttt tag(gctcgag
301   gcgtctgccg cacctcagcc cacgacctgc cccgctggga ggtgcgggcc gctggccagg
361   ccctgaccgc aacctggccc agaggcccca gccctcaggc aaggttctcc gg)gtaagtgt
421   ggggccctga ggcgctgtgg ggtgaagagg tctatggagg ggcgcctgtg tacctagggc
481   cttcctgcac tcacaagccc ccaggaggtg ccaggatccg ggagcctccc agggcctgga
541   ggggagtccc tgatgggttc ctgccgccac acctgtgacc atcacatgag tgtggagaga
601   cgtttactga gcaagtgagg gaggccagcc tcaagggccg gctctggtgg ctgtgcaccg
661   gggtgacttg ggaacaacgt gttctacgtc agcaagacag gaacccatga tcccagagtt
721   gaacacactg ggcttgaccc ctcccaccgg gaggcccatg gtgggctgct gctgtggact
781   tggagcctca gcactcccga gactaatgct gcgtggatgt cgggttgcaa ggcggctgct
841   gcagctccag cagctccagc catcacgtcg agtctggaag aaggaggtgg ctgctgctgc
901   tttcacagaa gcaaactctc ccatcccctg ctgcaccctg gctcctggac cccagctggg
961   tgacttggga aagcaggggt ggtggtatta agcttgtctt acccgggtca tggctgttac
1021  ctggggctgg cacattgctg ctgggaccag aatgggattc tgcacaccag gcaagagggc
1081  gtgaacctcg ggtaggcagc tgaccgctcc acatgctccg ggaaaacagc acccatactc
1141  cagtagaggc tgggcctctc cgggcctgag tgccaggctg cactgagcca gggctcccac
1201  cgaaggcaca ctttatggct ttgagacagc tccttctgcc tctctgggct ttgggggaag
1261  gcagacatgg aagtgccggg agtctcagaa ctgcctgggg cctgagtttc tgagctggct
1321  tcttgcaggg gagtggctgc tgtgccttta ggcctctgtg ccgatgacct gggaggaagg
1381  tcagccttcc ccgctggagg gggcccagca aagcctcagc tcctagaagt gaggggcctg
1441  ccattgcctg cccgaggacc ccactcctgg gggccagatg ctgagagggg acactggggg
1501  cccagcagac cagagagctg accccagtcc cacagcctgg gtgggttgtc aacttctcgt
1561  gccccctcca actcctccac ccccacaccc ccttaggtaa ataggaggtc gaaacagagg
1621  ccagagggta aaggaggtgc ttagagtccg ggctggctca ggccggccgg gcagctgtgc
1681  tagtgcttgg agttcctgct cagtccccgt ggtctcctcg cccctctggg cacttgggct
1741  gccaggcacc gagctgagtg ccgagatgca aagatgagtc ccaggtctgc aggagttgga
1801  gcccagcagg gagctggcct tggggccggg cccctcctgc tctgggcagc cacccagccc
1861  tacgaccctc ctgtctctgt agggcctccc caaggccttg aatccacccc ggccccgtgc
1921  tcagtgcatc atgcccccca agccccagcc ctcctagagg tgtgggtggg ggaggggctg
1981  caacccacac aggctgagga cacagctgct gccactgcct ggggccagcc acgcatcctc
2041  cccagacagg gaccggtcta gctgtaccag ccgctgcccc ggacctgctg ccctgcccca
2101  cccccccctc ccctggccag cctccccaga ggccagaagg cgccttatcg ggcagggtta
2161  aggaggggga cagttatcag gggctgcagc ctagattggg ccacaatgtc ctcgtctctt
2221  gagggtggca ggctgtgcag gctccctgat aaaagcaccg gggaagggag gctcctggag
2281  tgtgctggaa ggaaacactg gcctcccaca tgcctgaggt cagggcttgg cctgagatgg
2341  aattctcgct tggtcccatc ctcccggcct gaccctgggc aaatgactct accactttgt
2401  gtctaggtca cctgttaagt caggcgacag acccggtgag ggagtcagcc cccgaccctt
2461  agtgcccctc tcctaacagc agcctcagag gggtcttga ctgccgccct ccatccgctt
```

-continued

```
2521  gttttacag(t gaagccacag cctggccacc tgtcttgatc tccccaccga gaaggccccg
2581  cccctcccgc tgcagcccca cagcatgcag ccccaggaga gccacgtcca ctatagtagg
2641  tgggaggacg gcagcaggga cggagtc                 cagcac agaagaggcc
2684  tcacgctgcc gcag)gtgagg ggcctgaggg cagcctgcca gccatagcag gctggtgtct
2744  ccctccagag acgcctgccc taacccctgc taccggcccc atcaccctcc accccatcct
2804  ggctgggagc ccacggtcca gcagctcagc aaaccgcagc ctttggcctt ccctctggtt
2864  ggctgtgggc ggggagagct tcctctcaac tccagcagag cgcccaggcc cctcccccctg
2924  acccagacca acggccacag tccacttagg gggcccctca tgcggccctg gcctggggct
2984  cacctccagt tggttctcac cccag(gatct cccagaggct gtgcacgggc aagctgggca
3044  tcgccatgaa ggtgctgggc ggcgtggccc tcttctggat catcttcatc ctgggctacc
3104  tcacaggcta ctatgtgcac aagtgcaaat aaatgctgcc ccgcatgcac gcggggggct
3164  ggccgca)
```

Portions within parentheses indicate exons based on the wild type structure however the deletion extends the open reading frame and the sequence in blue indicates the potential new translated sequence until the next in-frame stop codon. Underline indicates the start and stop codons. Bold italics indicate the polymorphic nucleotides in intron 3 that are invariantly mutated (c.110+193t>c and c.110+194g>a) in the mutant phenotype.

Nucleotides (SNPs) 2872 and 2873 are invariably associated with Vel negative but individually are not restricted to Vel negative.

SEQ ID NO. 3: cDNA based on SEQ ID NO. 1

```
  1  GGTGAGGCGC GCGGGGTCCG GGCTGCGGCT TCCCGGTGCG GCCGCAGTGG GCAGGCTCGA
 61  GGCGTCTGCC GCACCTCAGC CCACGACCTG CCCCGCTGGG AGGTGCGGGC CGCTGGCCAG
121  GCCCTGACCG CAACCTGGCC CAGAGGCCCC AGCCCTCAGG CAAGGTTCTC CGGTGAAGCC
181  ACAGCCTGGC CACCTGTCTT GATCTCCCCA CCGAGAAGGC CCCGCCCCTC CCGCTGCAGC
241  CCCACAGCAT GCAGCCCCAG GAGAGCCACG TCCACTATAG TAGGTGGGAG GACGGCAGCA
301  GGGACGGAGT CAGCCTAGGG GCTGTGTCCA GCACAGAAGA GGCCTCACGC TGCCGCAGGA
361  TCTCCCAGAG GCTGTGCACG GGCAAGCTGG GCATCGCCAT GAAGGTGCTG GGCGGCGTGG
421  CCCTCTTCTG GATCATCTTC ATCCTGGGCT ACCTCACAGG CTACTATGTG CACAAGTGCA
481  AATAAATGCT GCCCCGCATG CACGCGGGGG GCTGGCCGCA AAAAAAAAAA
```

Note: This full-length mRNA sequence has been determined experimentally by 3' RACE. The bold italics indicate the deletion identified in the genomic sequence of all Vel negative individuals sequenced to date. Underline indicates the start and stop codons.

SEQ ID NO. 4: cDNA based on SEQ ID NO. 2 (17-bp deletion not present)

```
  1  GGTGAGGCGC GCGGGGTCCG GGCTGCGGCT TCCCGGTGCG GCCGCAGTGG GCAGGCTCGA
 61  GGCGTCTGCC GCACCTCAGC CCACGACCTG CCCCGCTGGG AGGTGCGGGC CGCTGGCCAG
121  GCCCTGACCG CAACCTGGCC CAGAGGCCCC AGCCCTCAGG CAAGGTTCTC CGGTGAAGCC
181  ACAGCCTGGC CACCTGTCTT GATCTCCCCA CCGAGAAGGC CCCGCCCCTC CCGCTGCAGC
241  CCCACAGCAT GCAGCCCCAG GAGAGCCACG TCCACTATAG TAGGTGGGAG GACGGCAGCA
301  GGGACGGAGT CCAGCACAGA AGAGGCCTCA CGCTGCCGCA GGATCTCCCA GAGGCTGTGC
361  ACGGGCAAGC TGGGCATCGC CATGAAGGTG CTGGGCGGCG TGGCCCTCTT CTGGATCATC
```

-continued

```
421    TTCATCCTGG GCTACCTCAC AGGCTACTAT GTGCACAAGT GCAAATAAAT GCTGCCCCGC

481    ATGCACGCGG GGGGCTGGCC GCAAAAAAAA AAA
```

SEQ ID NO. 5: Translated SMIM1 protein
MQPQESHVHYSRWEDGSRDGVSLGAVSSTEEASRCRRISQRLCTGKLGIAMK(VLG
GVALFWIIFILGYLTGYYVH)KCK The portion within parentheses indicates predicted membrane-spanning domain as predicted by TMHMM (www.cbs.dtu.dk/services/TMHMM/)

SEQ ID NO. 6: Peptide 1
MQPQESHVHYSRWED

SEQ ID NO. 7: Peptide 2
SRWEDGSRDGVSLGA

SEQ ID NO. 8: Peptide 3
GVSLGAVSSTEEASR

SEQ ID NO. 9: Peptide 4
EASRCRRISQRLCTG

SEQ ID NO. 10: Peptide 5 (scrambled peptide 1)
CPESWHSYMRVQHEQD

SEQ ID NO. 11: cDNA primer 388588cDNAf
CGCACCTCAGCCCACGAC

SEQ ID NO. 12: cDNA primer 388588cDNAr
TCCAGGCCTGTGCTCTCAC

SEQ ID NO. 13: Vel negativeF PCR primer
GCCGAATTCGCCACCATGCAGCCCCAGGAGAGC

SEQ ID NO. 14: Vel negativeR2 PCR primer
GCCGGATCCCCCTTATTTGCACTTGTGCACATA

SEQ ID NO. 15: 388588int2f PCR primer
TCTCCTAACAGCAGCCTCAG

SEQ ID NO. 16: 388588ex4r PCR primer
TGTCTCCAGGCCTGTGCTC

SEQ ID NO. 17: 388588int3f PCR primer
CAGCTCAGCAAACCGCAGC

SEQ ID NO. 18: 388588int3r PCR primer
GGCGCTCTGCTGGAGTCA

SEQ ID NO. 19: 388588int3r2 PCR primer
CTGGGCGCTCTGCTGGAG

SEQ ID NO. 20: Allele specific PCR primer-388588wtex3f
CGGAGTCAGCCTAGGGGC

SEQ ID NO. 21: Allele specific PCR primer-388588mutex3f
GGACGGAGTCCAGCACAG

SEQ ID NO. 22: LOCex3f_screen PCR primer
ACAGCCTGGCCACCTGTCTTG

SEQ ID NO. 23: LOCex3r_screen PCR primer
CTGCGGCAGCGTGAGGC

SEQ ID NO. 24: RACE primer Vel 59F
GGCCGCAGTGGGCAGGCTC

SEQ ID NO. 25: RACE primer Vel 176F
CTCAGGCAAGGTTCTCCGGTGA

SEQ ID NO. 26: RACE primer Vel 280F
AGGAGAGCCACGTCCACTATAG

SEQ ID NO. 27: RACE primer Vel 332R
GCAGCGTGAGGCCTCTTCTGTG

-continued

SEQ ID NO. 28: RACE primer Vel 355R
CACAGCCTCTGGGAGATCCTGC

SEQ ID NO. 29: RACE primer Vel 376R
GATGCCCAGCTTGCCCGTGC

SEQ ID NO. 30: Exon 3 of SMIM1
TGAAGCCAC AGCCTGGCCA CCTGTCTTGA TCTCCCCACC GAGAAGGCCC CGCCCCTCCC

GCTGCAGCCC CACAGCATGC AGCCCCAGGA GAGCCACGTC CACTATAGTA GGTGGGAGGA

CGGCAGCAGG GACGGAGTC*A GCCTAGGGGC TGTGTC*CAGC ACAGAAGAGG CCTCACGCTG

CCGCAG

SEQ ID NO. 31: 17 bp deletion
AGCCTAG GGGCTGTGTC

SEQ ID NO. 32: SMIM1-mutant phenotype extended to subsequent stop codon

```
   1   (ggtgaggcgc gcggggtccg ggctgcggct tcccggtgcg gccgcagtgg gcag)gtgcga

  61   ctgtgcgcgg cctcgctggc tgagaactgg cgggggtggg ggcgtgccct ggactgaccc

 121   ccaccggcct aacccgcggt gcggggccag ggccggaact gcccgcccgg ctccttgccc

 181   ggctccttgt ggctgctggg gacccccgac accagccact ttcccttccc ggcccttagc

 241   aagatcggct tctccggtca cctttatttt tttag(gctcg aggcgtctgc cgcacctcag

 301   cccacgacct gccccgctgg gaggtgcggg ccgctggcca ggccctgacc gcaacctggc

 361   ccagaggccc cagccctcag gcaaggttct ccgg)gtaagt gtggggccct gaggcgctgt

 421   ggggtgaaga ggtctatgga ggggcgcctg tgtacctagg gccttcctgc actcacaagc

 481   ccccaggagg tgccaggatc cgggagcctc ccagggcctg gaggggagtc cctgatgggt

 541   tcctgccgcc acacctgtga ccatcacatg agtgtggaga gacgtttact gagcaagtga

 601   gggaggccag cctcaagggc cggctctggt ggctgtgcac cggggtgact tgggaacaac

 661   gtgttctacg tcagcaagac aggaacccat gatcccagag ttgaacacac tgggcttgac

 721   ccctcccacc gggaggccca tggtgggctg ctgctgtgga cttggagcct cagcactccc

 781   gagactaatg ctgcgtggat gtcgggttgc aaggcggctg ctgcagctcc agcagctcca

 841   gccatcacgt cgagtctgga agaaggaggt ggctgctgct gctttcacag aagcaaactc

 901   tcccatcccc tgctgcaccc tggctcctgg accccagctg ggtgacttgg gaaagcaggg

 961   gtggtggtat taagcttgtc ttacccgggt catggctgtt acctggggct ggcacattgc

1021   tgctgggacc agaatgggat tctgcacacc aggcaagagg gcgtgaacct cgggtaggca

1081   gctgaccgct ccacatgctc cgggaaaaca gcacccatac tccagtagag gctgggcctc

1141   tccgggcctg agtgccaggc tgcactgagc cagggctccc accgaaggca cactttatgg

1201   ctttgagaca gctccttctg cctctctggg ctttggggga aggcagacat ggaagtgccg

1261   ggagtctcag aactgcctgg ggcctgagtt tctgagctgg cttcttgcag gggagtggct

1321   gctgtgcctt taggcctctg tgccgatgac ctgggaggaa ggtcagcctt ccccgctgga

1381   gggggcccag caaagcctca gctcctagaa gtgaggggcc tgccattgcc tgcccgagga

1441   ccccactcct gggggccaga tgctgagagg ggacactggg ggcccagcag accagagagc

1501   tgaccccagt cccacagcct gggtgggttg tcaacttctc gtgccccctc caactcctcc

1561   acccccacac ccccttaggt aaataggagg tcgaaacaga ggccagaggg taaaggaggt

1621   gcttagagtc cgggctggct caggccggcc gggcagctgt gctagtgctt ggagttcctg

1681   ctcagtcccc gtggtctcct cgcccctctg ggcacttggg ctgccaggca ccgagctgag

1741   tgccgagatg caaagatgag tcccaggtct gcaggagttg gagcccagca gggagctggc

1801   cttggggccg ggcccctcct gctctgggca gccacccagc cctacgaccc tcctgtctct
```

-continued 1861 gtagggcctc cccaaggcct tgaatccacc ccggccccgt gctcagtgca tcatgccccc 1921 caagccccag ccctcctaga ggtgtgggtg ggggaggggc tgcaacccac acaggctgag 1981 gacacagctg ctgccactgc ctggggccag ccacgcatcc tccccagaca gggaccggtc 2041 tagctgtacc agccgctgcc ccggacctgc tgccctgccc caccccccc tcccctggcc 2101 agcctcccca gaggccagaa ggcgccttat cgggcagggt taaggagggg gacagttatc 2161 aggggctgca gcctagattg ggccacaatg tcctcgtctc ttgagggtgg caggctgtgc 2221 aggctccctg ataaaagcac cggggaaggg aggctcctgg agtgtgctgg aaggaaacac 2281 tggcctccca catgcctgag gtcagggctt ggcctgagat ggaattctcg cttggtccca 2341 tcctcccggc ctgaccctgg gcaaatgact ctaccacttt gtgtctaggt cacctgttaa 2401 gtcaggcgac agacccggtg agggagtcag cccccgaccc ttagtgcccc tctcctaaca 2461 gcagcctcag agggggtctt gactgccgcc ctccatccgc ttgttttaca g(tgaagccac 2521 agcctggcca cctgtcttga tctccccacc gagaaggccc cgcccctccc gctgcagccc 2581 cacagcatgc agccccagga gagccacgtc cactatagta ggtgggagga cggcagcagg 2641 gacggagtcc agcacagaag aggcctcacg ctgccgcag)g tgaggggcct gagggcagcc 2701 tgccagccat agcaggctgg tgtctccctc cagagacgcc tgccctaacc cctgctaccg 2761 gccccatcac cctccacccc atcctggctg ggagcccacg gtccagcagc tcagcaaacc 2821 gcagcctttg gccttccctc tggttggctg tgggcgggga gagcttcctc tcaactccag 2881 cagagcgccc aggcccctcc ccctgaccca gaccaacggc cacagtccac ttaggggggcc 2941 cctcatgcgg ccctggcctg ggctcacct ccagttggtt ctcaccccag (gatctcccag 3001 aggctgtgca cgggcaagct gggcatcgcc atgaaggtgc tgggcggcgt ggccctcttc 3061 tggatcatct tcatcctggg ctacctcaca ggctactatg tgcacaagtg caaataaatg 3121 ctgccccgca tgcacgcggg gggctggccg cacacgtgag agcacaggcc tggagaca)ca 3181 ccccttgtac acatggaccc ccccacagac acggaccctg cggcacacac agcgcacagg 3241 gcacacgcgc tggcagccag gcacacgaag acaccaggtg cacagctgtc ateggcccca 3301 cacgggggcg cacaaacacc tggcacacag cccttcaaag gacctacaaa cagctgggca 3361 cacgtggctg ggaggcctgg gcccagcctc agcaggagct gcaggacaca cccaggctgg 3421 gccctgcggc ctggagcccc cagctacagc ctcctctctc ccagggccca gccccttccc 3481 ttgtgaaggc caggatgagg ggttccttca gcggacaaac cgagcccacc tccctggcag 3541 ccccccgggg tgggatcctc ccggctgctt tcctccgtgg gagcagtgtg cagagctgtg 3601 tggccctggg caggcccctg tcctctctgg gcctttctga ctcctggttt tgtaagggtg 3661 gctatgtgtc ccccgccctt gtctcagatg caccatatct tccttagtaa gtgggcacag 3721 ttcttcctag gcagcccacc acgcgcagag gctgggtgtg tccctcttgg ggccggcg..

In this mutant sequence, the wt stop codon is abolished and the premise is that the transcript is extended until the next predicted stop codon; in this case 590 bp downstream of the wild type stop codon.

SEQ ID NO. 33: SMIM1 var 1 (chr1:3691980 A/G)

1 (ggtgaggcgc gcggggtccg ggctgcggct tcccggtgcg gccgcagtgg gcag)gtgcga 61 ctgtgcgcgg cctcgctggc tgagaactgg cgggggtggg ggcgtgccct ggactgaccc 121 ccaccggcct aacccgcggt gcggggccag ggccggaact gcccgcccgg ctccttgccc 181 ggctccttgt ggctgctggg gacccccgac accagccact ttcccttccc ggcccttagc -continued 241 aagatcggct tctccggtca cctttatttt tttag(gctcg aggcgtctgc cgcacctcag 301 cccacgacct gccccgctgg gaggtgcggg ccgctggcca ggccctgacc gcaacctggc 361 ccagaggccc cagccctcag gcaaggttct ccgg)gtaagt gtggggccct gaggcgctgt 421 ggggtgaaga ggtctatgga ggggcgcctg tgtacctagg gccttcctgc actcacaagc 481 ccccaggagg tgccaggatc cgggagcctc ccagggcctg gaggggagtc cctgatgggt 541 tcctgccgcc acacctgtga ccatcacatg agtgtggaga gacgtttact gagcaagtga 601 gggaggccag cctcaagggc cggctctggt ggctgtgcac cggggtgact tgggaacaac 661 gtgttctacg tcagcaagac aggaacccat gatcccagag ttgaacacac tgggcttgac 721 ccctcccacc gggaggccca tggtgggctg ctgctgtgga cttggagcct cagcactccc 781 gagactaatg ctgcgtggat gtcgggttgc aaggcggctg ctgcagctcc agcagctcca 841 gccatcacgt cgagtctgga agaaggaggt ggctgctgct gctttcacag aagcaaactc 901 tcccatcccc tgctgcaccc tggctcctgg accccagctg ggtgacttgg gaaagcaggg 961 gtggtggtat taagcttgtc ttacccgggt catggctgtt acctggggct ggcacattgc 1021 tgctgggacc agaatgggat tctgcacacc aggcaagagg gcgtgaacct cgggtaggca 1081 gctgaccgct ccacatgctc cgggaaaaca gcacccatac tccagtagag gctgggcctc 1141 tccgggcctg agtgccaggc tgcactgagc cagggctccc accgaaggca cactttatgg 1201 ctttgagaca gctccttctg cctctctggg ctttggggga aggcagacat ggaagtgccg 1261 ggagtctcag aactgcctgg ggcctgagtt tctgagctgg cttcttgcag gggagtggct 1321 gctgtgcctt taggcctctg tgccgatgac ctgggaggaa ggtcagcctt ccccgctgga 1381 gggggcccag caaagcctca gctcctagaa gtgaggggcc tgccattgcc tgcccgagga 1441 ccccactcct gggggccaga tgctgagagg ggacactggg ggcccagcag accagagagc 1501 tgaccccagt cccacagcct gggtgggttg tcaacttctc gtgccccctc caactcctcc 1561 acccccacac cccccttaggt aaataggagg tcgaaacaga ggccagaggg taaaggaggt 1621 gcttagagtc cgggctggct caggccggcc gggcagctgt gctagtgctt ggagttcctg 1681 ctcagtcccc gtggtctcct cgcccctctg ggcacttggg ctgccaggca ccgagctgag 1741 tgccgagatg caaagatgag tcccaggtct gcaggagttg gagcccagca gggagctggc 1801 cttggggccg ggcccctcct gctctgggca gccacccagc cctacgaccc tcctgtctct 1861 gtagggcctc cccaaggcct tgaatccacc ccggccccgt gctcagtgca tcatgccccc 1921 caagccccag ccctcctaga ggtgtgggtg ggggaggggc tgcaacccac acaggctgag 1981 gacacagctg ctgccactgc ctggggccag ccacgcatcc tccccagaca gggaccggtc 2041 tagctgtacc agccgctgcc ccggacctgc tgccctgccc caccccccc tcccctggcc 2101 agcctcccca gaggccagaa ggcgccttat cgggcagggt taaggagggg gacagttatc 2161 aggggctgca gcctagattg ggccacaatg tcctcgtctc ttgagggtgg caggctgtgc 2221 aggctccctg ataaaagcac cggggaaggg aggctcctgg agtgtgctgg aaggaaacac 2281 tggcctccca catgcctgag gtcagggctt ggcctgagat ggaattctcg cttggtccca 2341 tcctcccggc ctgaccctgg gcaaatgact ctaccacttt gtgtctaggt cacctgttaa 2401 gtcaggcgac agacccggtg agggagtcag cccccgaccc ttagtgcccc tctcctaaca 2461 gcagcctcag agggggtctt gactgccgcc ctccatccgc ttgttttaca g(tgaagccac 2521 agcctggcca cctgtcttga tctccccacc gagaaggccc cgcccctccc gctgcagccc 2581 cacagcatgc agccccagga gagccacgtc cactatagta ggtgggagAa cggcagcagg -continued 2641 gacggagtc*a gcctaggggc tgtgtc*cagc acagaagagg cctcacgctg ccgcag)gtga 2701 ggggcctgag ggcagcctgc cagccatagc aggctggtgt ctccctccag agacgcctgc 2761 cctaacccct gctaccggcc ccatcaccct ccaccccatc ctggctggga gcccacggtc 2821 cagcagctca gcaaaccgca gcctttggcc ttccctctgg ttggctgtgg gcggggagag 2881 cttcctcttg actccagcag agcgcccagg cccctccccc tgacccagac caacggccac 2941 agtccactta gggggcccct catgcggccc tggcctgggg ctcacctcca gttggttctc 3001 accccag(gat ctcccagagg ctgtgcacgg gcaagctggg catcgccatg aaggtgctgg 3061 gcggcgtggc cctcttctgg atcatcttca tcctgggcta cctcacaggc tactatgtgc 3121 acaagtgcaa ataaatgctg ccccgcatgc acgcgggggg ctggccgcac acgtgagagc 3181 acaggcctgg agaca)

SEQ ID NO. 34: SMIM1 var 2 (chr1:3691980 A/G)

1 (ggtgaggcgc gcggggtccg ggctgcggct tcccggtgcg gccgcagtgg gcag)gtgcga 61 ctgtgcgcgg cctcgctggc tgagaactgg cgggggtggg ggcgtgccct ggactgaccc 121 ccaccggcct aacccgcggt gcggggccag ggccggaact gcccgcccgg ctccttgccc 181 ggctccttgt ggctgctggg gacccccgac accagccact ttcccttccc ggcccttagc 241 aagatcggct tctccggtca cctttatttt tttag(gctcg aggcgtctgc cgcacctcag 301 cccacgacct gccccgctgg gaggtgcggg ccgctggcca ggccctgacc gcaacctggc 361 ccagaggccc cagccctcag gcaaggttct ccgg)gtaagt gtggggccct gaggcgctgt 421 ggggtgaaga ggtctatgga ggggcgcctg tgtacctagg gccttcctgc actcacaagc 481 ccccaggagg tgccaggatc cgggagcctc ccagggcctg gaggggagtc cctgatgggt 541 tcctgccgcc acacctgtga ccatcacatg agtgtggaga gacgtttact gagcaagtga 601 gggaggccag cctcaagggc cggctctggt ggctgtgcac cggggtgact tgggaacaac 661 gtgttctacg tcagcaagac aggaacccat gatcccagag ttgaacacac tgggcttgac 721 ccctcccacc gggaggccca tggtgggctg ctgctgtgga cttggagcct cagcactccc 781 gagactaatg ctgcgtggat gtcgggttgc aaggcggctg ctgcagctcc agcagctcca 841 gccatcacgt cgagtctgga agaaggaggt ggctgctgct gctttcacag aagcaaactc 901 tcccatcccc tgctgcaccc tggctcctgg accccagctg ggtgacttgg gaaagcaggg 961 gtggtggtat taagcttgtc ttacccgggt catggctgtt acctggggct ggcacattgc 1021 tgctgggacc agaatgggat tctgcacacc aggcaagagg gcgtgaacct cgggtaggca 1081 gctgaccgct ccacatgctc cgggaaaaca gcacccatac tccagtagag gctgggcctc 1141 tccgggcctg agtgccaggc tgcactgagc cagggctccc accgaaggca cactttatgg 1201 ctttgagaca gctccttctg cctctctggg ctttggggga aggcagacat ggaagtgccg 1261 ggagtctcag aactgcctgg ggcctgagtt tctgagctgg cttcttgcag gggagtggct 1321 gctgtgcctt taggcctctg tgccgatgac ctgggaggaa ggtcagcctt ccccgctgga 1381 gggggcccag caaagcctca gctcctagaa gtgaggggcc tgccattgcc tgcccgagga 1441 ccccactcct gggggccaga tgctgagagg ggacactggg ggcccagcag accagagagc 1501 tgaccccagt cccacagcct gggtgggttg tcaacttctc gtgccccctc caactcctcc 1561 acccccacac ccccttaggt aaataggagg tcgaaacaga ggccagaggg taaaggaggt 1621 gcttagagtc cgggctggct caggccggcc gggcagctgt gctagtgctt ggagttcctg 1681 ctcagtcccc gtggtctcct cgcccctctg ggcacttggg ctgccaggca ccgagctgag 1741 tgccgagatg caaagatgag tcccaggtct gcaggagttg gagcccagca gggagctggc -continued 1801 cttggggccg ggcccctcct gctctgggca gccacccagc cctacgaccc tcctgtctct 1861 gtagggcctc cccaaggcct tgaatccacc ccggccccgt gctcagtgca tcatgccccc 1921 caagccccag ccctcctaga ggtgtgggtg ggggaggggc tgcaacccac acaggctgag 1981 gacacagctg ctgccactgc ctggggccag ccacgcatcc tccccagaca gggaccggtc 2041 tagctgtacc agccgctgcc ccggacctgc tgccctgccc caccccccc tcccctggcc 2101 agcctcccca gaggccagaa ggcgccttat cggcagggt taaggagggg gacagttatc 2161 aggggctgca gcctagattg ggccacaatg tcctcgtctc ttgagggtgg caggctgtgc 2221 aggctccctg ataaaagcac cggggaaggg aggctcctgg agtgtgctgg aaggaaacac 2281 tggcctccca catgcctgag gtcagggctt ggcctgagat ggaattctcg cttggtccca 2341 tcctcccggc ctgaccctgg gcaaatgact ctaccacttt gtgtctaggt cacctgttaa 2401 gtcaggcgac agacccggtg agggagtcag cccccgaccc ttagtgcccc tctcctaaca 2461 gcagcctcag agggggtctt gactgccgcc ctccatccgc ttgttttaca g(tgaagccac 2521 agcctggcca cctgtcttga tctccccacc gagaaggccc cgcccctccc gctgcagccc 2581 cacagcatgc agccccagga gagccacgtc cactatagta ggtgggagga cggcagcagg 2641 gacggagtc*a* *gcctaggggc tgtgtc*cagc acagaagagg cctcacgctg ccgcag)gtga 2701 ggggcctgag ggcagcctgc cagccatagc aggctggtgt ctccctccag agacgcctgc 2761 cctaacccct gctaccggcc ccatcaccct ccaccccatc ctggctggga gcccacggtc 2821 cagcagctca gcaaaccgca gcctttggcc ttccctctgg ttggctgtgg gcggggagag 2881 cttcctcttg actccagcag agcgcccagg cccctccccc tgacccagac caacggccac 2941 agtccactta gggggcccct catgcggccc tggcctgggg ctcacctcca gttggttctc 3001 accccag(gat ctcccagagg ctgtgcacgg gcaagctggg catcgccatg aaggtgctgg 3061 gcggcgtggc cctcttctgg atcatcttca tcctgggcta cctcacaggc tactatAtgc 3121 acaagtgcaa ataaatgctg ccccgcatgc acgcgggggg ctggccgcac acgtgagagc 3181 acaggcctgg agaca)

SEQ ID NO. 35: cDNA of SMIM1 variant (transcript according to 5' and 3' RACE in blood)

1 CAGAGACGCG GGGACACAGg ctcgaggcgt ctgccgcacc tcagcccacg acctgccccg 61 ctgggaggtg cgggccgctg gccaggccct gaccgcaacc tggcccagag gccccagccc 121 tcaggcaagg ttctccggtg aagccacagc ctggccacct gtcttgatct ccccaccgag 181 aaggccccgc ccctcccgct gcagccccac agcatgcagc cccaggagag ccacgtccac 241 tatagtaggt gggaggacgg cagcagggac ggagtcagcc taggggctgt gtccagcaca 301 gaagaggcct cacgctgccg caggatctcc cagaggctgt gcacgggcaa gctgggcatc 361 gccatgaagg tgctgggcgg cgtggccctc ttctggatca tcttcatcct gggctacctc 421 acaggctact atgtgcacaa gtgcaaataa atgctgcccc gcatgcacgc ggggggctgg 481 ccgcaaaaaa aaaaaaa SEQ ID NO. 36: cDNA of SMIM1 variant (transcript according to 5' and 3' RACE in blood; 17 bp deletion)

1 CAGAGACGCG GGGACACAGg ctcgaggcgt ctgccgcacc tcagcccacg acctgccccg 61 ctgggaggtg cgggccgctg gccaggccct gaccgcaacc tggcccagag gccccagccc 121 tcaggcaagg ttctccggtg aagccacagc ctggccacct gtcttgatct ccccaccgag 181 aaggccccgc ccctcccgct gcagccccac agcatgcagc cccaggagag ccacgtccac 241 tatagtaggt gggaggacgg cagcagggac ggagtc cagcaca 284 gaagaggcct cacgctgccg caggatctcc cagaggctgt gcacgggcaa gctgggcatc -continued

```
344    gccatgaagg tgctgggcgg cgtggccctc ttctggatca tcttcatcct gggctacctc

404    acaggctact atgtgcacaa gtgcaaataa atgctgcccc gcatgcacgc ggggggctgg

464    ccgcaaaaaa aaaaaaa
```

Example 2: Identification of the Vel Antigen

Background

The Vel blood group antigen is located on red blood cells and is one of a few so-called orphan blood group antigens for which the molecular basis is unknown. It is clinically important and thus identification of the carrier molecule would permit the development of a screening assay to identify blood donors appropriate for immunized Vel negative/negative patients, and also patients at risk of producing an unwanted antibody.

The present inventors provided understanding of the molecular and genetic basis of the Vel blood group antigen. This has been achieved through a range of serological and biochemical investigations, including investigations of candidate genes. These investigations resulted in estimates of the size of the red blood cell protein carrying the Vel antigen and a likely homodimer configuration.

A hypothesis that the gene encoding the Vel blood group antigen could potentially be triangulated via genome-wide genetic screening using single-nucleotide polymorphism (SNP) arrays was based on three observations:

(a) the Vel negative/negative phenotype is believed to be more common in Sweden (1:1700, compared to approx. 1:4000 in other populations), (b) the Vel negative phenotype is inherited in an autosomal-recessive manner, and (c) the gene encoding the Vel antigen, like several other blood group genes, could be preferentially expressed on erythrocytes.

Together, these observations made the inventors suggest that the Vel negative phenotype could be caused by a single founder mutation in the Swedish population, in which case a genome-wide genetic screen could succeed despite the relatively limited number of DNA samples from Vel negative individuals available.

Accordingly, genome-wide SNP profiles of Vel negative donors were collected using Illumina Human Omni 2.5M-Quad microarrays. Using a computational strategy conceived and executed collaboratively by the present inventors, a region on chromosome 1 containing 5 genes was identified.

Following review of the characteristics of these genes, it was determined that SMIM1 (LOC388588) was the most promising because:

(a) its predicted structure corresponded to a transmembrane protein, (b) its predicted size matched the size estimates of the inventor's earlier biochemical studies, and (c) analyses of pre-existing gene expression microarray data retrieved from public data bases indicated that it was preferentially expressed in red blood cell precursors.

With this information in hand, the inventors determined the DNA sequence of SMIM1 (LOC388588) in Vel negative donors and found a 17-basepair deletion that destroys the protein, causing a so-called null or knock-out phenotype.

Subsequent genetic studies have identified the exact same 17-base-pair deletion in all Vel negative donors from Sweden, UK, Switzerland, Israel and the USA tested to date, suggesting that it is indeed the predominating cause of the Vel negative phenotype. Additional sequence analysis revealed homozygosity for the 17-base-pair deletion in a further five Vel-samples of Swiss origin and 2 samples of Israeli origin. This has set the stage for identification of Vel negative blood donors by genetic testing.

Samples

Approvals from The Regional Ethics Review Board at Lund University were obtained for bone marrow collection and genetic blood group analysis on blood samples from blood donors. Anticoagulated blood samples from Swedish Vel negative and Vel positive donors were drawn under informed consent according to routine blood donation practice. Other Vel negative samples used were from a rare donor collection assembled from an international rare sample exchange scheme, SCARF (http://scarfex.iove.Drohostina-.com/); or sent directly to our reference laboratory for investigation by other reference laboratories. DNA sample panels used for screening to establish mutation prevalence were anonymized samples from normal Swedish blood donors.

TABLE 1

Discovery cohort of Vel negative and Vel positive samples analysed on the Illumina HumanOmni 2.5M BeadChip microarray.

| Sample number<br>Sample number | Vel phenotype<br>Vel phenotype | Comments<br>Comments | Origin |
|---|---|---|---|
| 1 | Vel negative | Blood donor | Sweden |
| 2 | Vel negative | Sibling of #1 | Sweden |
| 3 | Vel positive | Sibling of #1 | Sweden |
| 4 | Vel positive | Child of #1 | Sweden |
| 5 | Vel positive | Child of #1 | Sweden |
| 6 | Vel negative | Blood donor | Sweden |
| 7 | Vel negative | Sibling of #6 | Sweden |
| 8 | Vel negative | Sibling of #6 | Sweden |
| 9 | Vel positive | Sibling of #6 | Sweden |
| 10 | Vel negative | Unrelated blood donor | Sweden |
| 11 | Vel negative | Unrelated blood donor | Sweden |
| 12 | Vel negative | Unrelated blood donor | Sweden |
| 13 | Vel positive | Unrelated blood donor | Sweden |
| 14 | Vel negative | Unrelated blood donor | Sweden |
| 15 | Vel negative | Unrelated blood donor | Sweden |
| 16 | Vel negative | Unrelated blood donor | Sweden |
| 17 | Vel negative | Unrelated blood donor | Sweden |
| 18 | Vel negative | Unrelated blood donor | Sweden |
| 19 | Vel negative | Unrelated blood donor | Sweden |
| 20 | Vel negative | Unrelated blood donor | Sweden |
| 21 | Vel negative | Unrelated blood donor | Sweden |
| 22 | Vel negative | Unrelated blood donor | Sweden |
| 23 | Vel positive | Unrelated blood donor | Sweden |
| 24 | Vel negative | Unrelated blood donor | USA |
| 25 | Vel negative | Unrelated blood donor | USA |
| 26 | Vel negative | Unrelated blood donor | USA |
| 27 | Vel positive | Unrelated blood donor | USA |
| 28 | Vel positive | Unrelated blood donor | Sweden |

Nucleic Acid Extraction

Genomic DNA was prepared either using a modified salting-out procedure and diluted to 100 ng/uL in water; or using the QIAamp DNA Blood Mini Kit (Qiagen AB, Sollentuna, Sweden) and used undiluted. Total RNA was extracted from whole blood or from cell lines using Trizol®

LS reagent (Life Technologies Europe BV, Stockholm, Sweden) according to the manufacturers instructions.

Generation and Analysis of Single-Nucleotide Polymorphism Array Data

Genomic DNA from 20 Vel negative and 8 Vel positive samples (Table 1) were subjected to genome-wide genotyping with respect to 2,443,179 single-nucleotide polymorphisms (SNPs) using Illumina HumanOmni 2.5M BeadChip microarrays (Illumina Inc, San Diego, Calif., USA; genotyping and genotype calling performed at the SCIBLU facility, Lund University, Sweden). Genotypes were called in GenomeStudio (Illumina Inc). Call rate was at least 99.5% for all samples. Four samples were genotyped twice on separate arrays with a concordance of at least 99.3%. Only the result in one of the arrays was subsequently analyzed.

Autosomal, unambiguous SNPs were selected for association testing. To find SNPs compatible with an autosomal recessive inheritance, we then applied a filter that selected SNPs where the Vel negative samples within each family were homozygous and identical whereas their Vel positive family members where heterozygous, or homozygous but non-identical. After applying this filter, 8,780 SNPs remained. All familial Vel negative samples (n=5) were removed prior to association testing. Association testing was carried out using the EUR panel subjects (n=379) in the final phase 1 release of the 1000 Genomes Project as controls. Genotype frequencies in the non-related Vel negative samples (n=15) where compared to controls using Fisher's exact test in R 2.14.1.

Breakpoints of the detected haplotype block were estimated from inspection of unfiltered genotype call data.

Sequencing of SMIM1

Genomic DNA from 31 Vel negative and 10 Vel positive samples were amplified and sequenced with primers 388588int2f (SEQ ID NO. 15) and 388588ex4r (SEQ ID NO. 16) which flanked exons 3 and 4 containing the SMIM1 open reading frame. (see Table 2; FIG. 1).

Amplified products were run on 3% agarose gel, excised, eluted, and sequenced using the BigDye Terminator v3.1 Cycle Sequencing Kit (Applied Biosystems, Life Technologies) on an ABI 3500 Dx Genetic Analyser. Sequence analysis was performed with SeqEd software v1.0 (Applied Biosystems).

Total RNA isolated from whole blood or cell lines was converted to cDNA using the High Capacity Kit (Applied Biosystems) according to the protocol. Amplification of mRNA was performed with the Expand High Fidelity PCR Kit (Roche Diagnostics Corporation, Indianapolis, Ind., USA) using primers 388588cDNAf (SEQ ID NO. 11) and 388588cDNAr (SEQ ID NO. 12). Products were sequenced as described above.

Genotyping Assays

Figure 2:
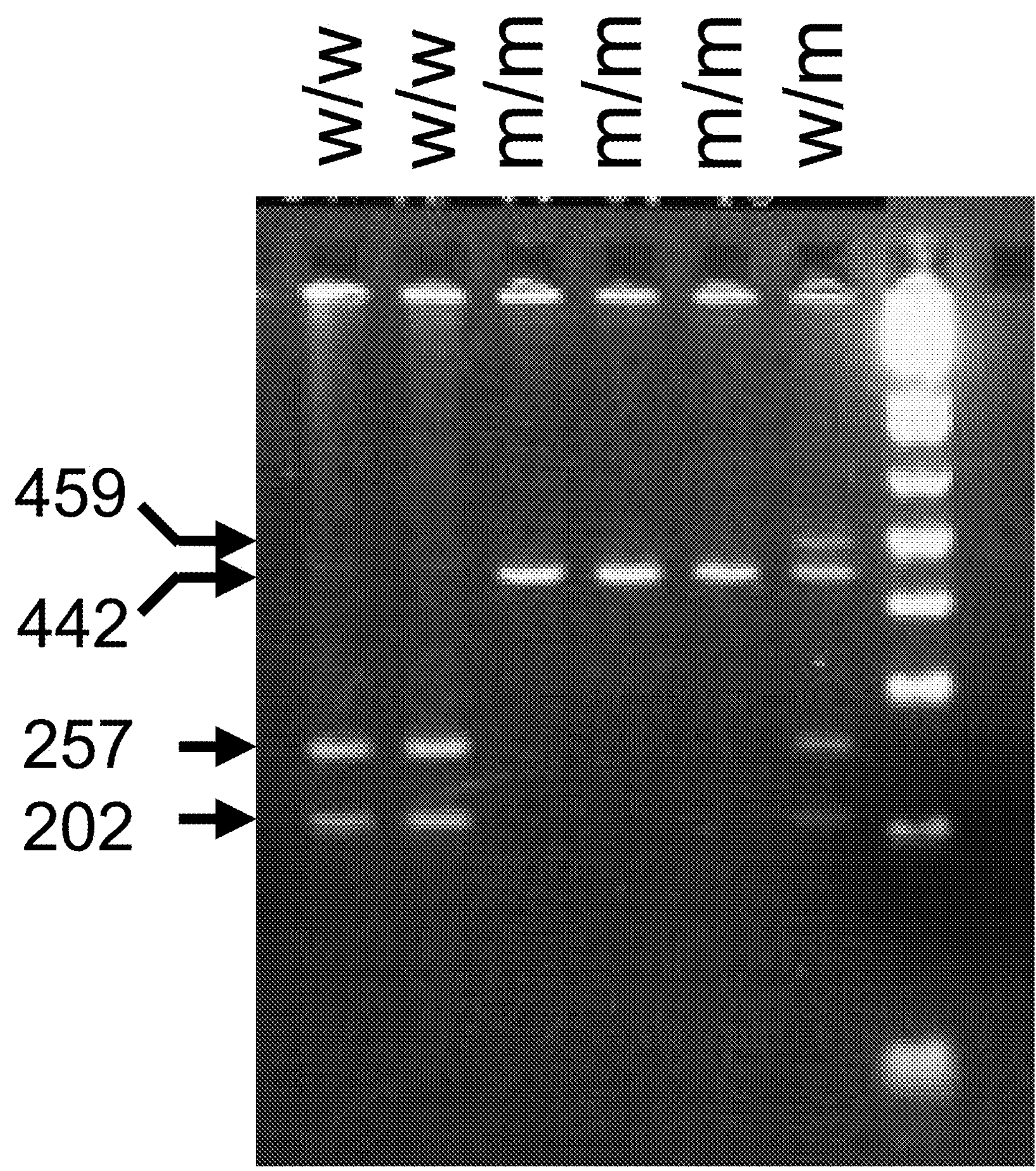
FIG. 2. PCR-RFLP of SMIM1 exon 3 using StyI. The wild type amplicon is digested into two fragments; whilst the mutated amplicon is not digested by the enzyme. Additionally, this amplicon can be distinguished on the gel by size, based on the 17-bp difference.
Figure 3:
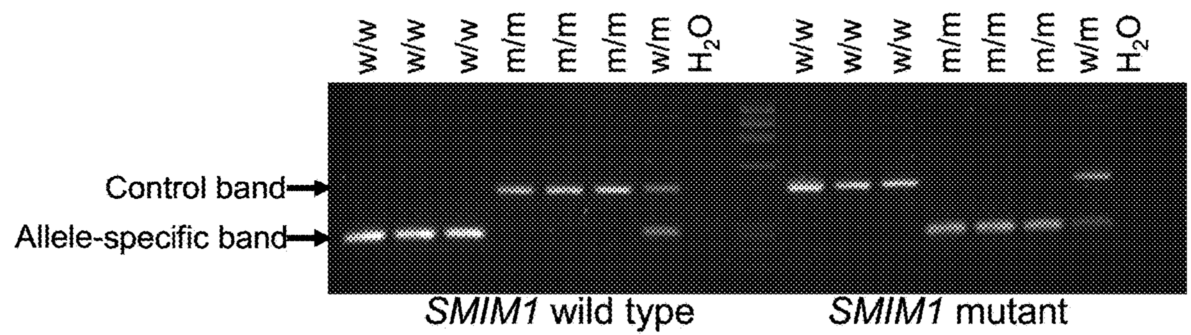
FIG. 3. Allele-specific PCR (ASP) of genomic DNA from individuals determined by sequencing to be w/w, w/m or m/m. The control band is generated by amplification of a region of SMIM1 encompassing the 17 bp deletion in the absence of allele-specific amplification.
Figure 4:
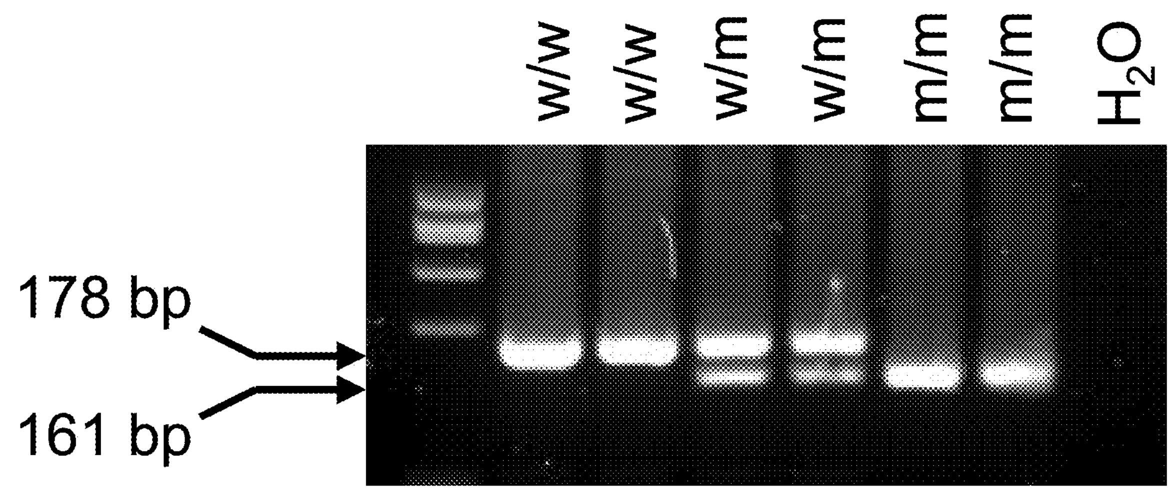
FIG. 4. Gene-specific PCR (GSP). Amplification of the region surrounding the 17-bp deletion permits discrimination of w/w, m/m and w/m samples on 3% agarose gel based solely on band size.

Assays to discriminate the wild type and mutant alleles were designed. All primers were synthesized by Life Technologies and used at a concentration of 10 pM unless otherwise stated. See table 2 for primer sequences.

i) PCR-RFLP: genomic DNA was amplified with primers 388588int2f (SEQ ID NO. 15) and 388588int3R2 (SEQ ID NO. 19). In this assay, the amplified bands are 459 and 442 bp respectively however, the size of the amplicon is arbitrary and other gene-specific primers surrounding the deletion could be designed by the person of skill in the art. The products were digested with StyI at 37° C. for two hours. Products were analysed on a 3% agarose gel. (see FIG. 2). The restriction site was abolished in the mutated sequence. In this assay, the amplified bands are 459 and 442 bp respectively however, the size of the amplicon is arbitrary and other gene-specific primers surrounding the deletion could be used.

ii) Allele-specific PCR (ASP): genomic DNA was amplified with primers 388588int2f (SEQ ID NO. 15) (1 pM), 388588int3R2 (SEQ ID NO. 19) and either 388588wtex3f (SEQ ID NO. 20) or 388588mutex3f (SEQ ID NO. 21). An internal control band was provided by the amplification of a 460 bp (wild type) or 443 bp (mutant) product. Allele-specific bands of 266 bp (wild type) or 249 bp (mutant) were specifically amplified by their respective primers (see FIG. 3)

iii) Gene-specific PCR (GSP): genomic DNA was amplified with primers LOCex3f_screen (SEQ ID NO. 22) and LOCex3r_screen (SEQ ID NO. 23) which flanked SMIM1 exon 3. Allele-specific PCR products of 178 bp (wild type) or 161 bp (mutant) were discriminated based on size by electrophoresis for 75 minutes at 165V on a 3% agarose gel (see FIG. 4) A total of 520 random genomic DNA samples were tested by GSP. Thirty heterozygote samples were identified. Thus the allele frequency in the southern Swedish population is 1 in 17 and the calculated frequency of individuals homozygous for the Vel mutation is 1 in 1200.

Reel-Time PCR and Data Analysis

Real-time quantitative PCR was performed on 3 μl cDNA with TaqMan probes and the 7500 sequence detection systems (Applied Biosystems), according to the manufacturer's instructions. Data was analyzed using the 7500 Sequence Detection Software version 1.3.1 (Applied Biosystems). SMIM1 transcripts were detected with a TaqMan® Gene Expression Assay (Hs01369635_g1, Applied Biosystems, binding to exon 3-4 boundary). Transcript target quantities were normalized to 18S ribosomal RNA (assay Hs99999901_s1). All samples were run in triplicates. The sample with the lowest $C_T$ value was used as calibrator. We considered as positive the results from any sample with at least two detected ($C_T$<40) values within the triplicate.

Rapid Amplification of cDNA Ends (RACE)

Messenger RNA was isolated from total RNA extracted from bone marrow cells cultured towards erythropoietic maturation as described previously by an mRNA Isolation Kit (Roche Diagnostics Corporation). RACE was performed with the FirstChoice RLM-RACE kit (Ambion) according to the manufacturer's recommendations. In the 5'-RACE, cDNA was synthesized with random primers provided with the kit Gene-specific primers Vel 332R (SEQ ID NO. 27), Vel 355R (SEQ ID NO. 28) and Vel 376R (SED ID NO. 29) were used for PCR amplification together with the 5'-RACE primers provided in the kit. For the 3'-RACE, PCR was performed with primers VEL 59F (SEQ ID NO. 24), VEL 176F (SEQ ID NO.25) and VEL 280F (SEQ ID NO. 26), together with the 3'-primers included in the kit. Primer sequences are shown in Table 2.

SMIM1 Knock-Down with shRNA Lentiviral Clones

SMIM1 was stably knocked-down in Human Erythroleukemic (HEL) and JK-1 cell lines by lentivirus-based shRNA vectors specific for SMIM1. The following libraries were purchased from SIGMA: TRCN0000365551, TRCN0000365607, TRCN0000365620, TRCN0000376652, TRCN0000376653, TRCN0000376654, TRCN0000422700 at a titer of $10^6$ in pLKO.1 vector. The transduction was performed according to the manufacturers' instructions. Briefly, $1.6\times10^4$ of HEL and JK-1 cells stably expressing SMIM1 were seeded in 96-well plate in 100 μl growth media per well at the day of transduction. Hexadimethyrine bromide was added to each well at a final concentration of 8 μg/ml. Transduction with shRNA lentiviral clones were carried out at a MOI (multiplicity of infection) ranging between 0.5 to 5. Lentiviral particles of a non-human transduction control (SH202V, SIGMA), a transduction efficiency control (SHC203V, SIGMA) and shRNA Lenti-viral particles for SMIM1 were added to the wells containing cells. The plate was centrifuged at 2300 rpm for 30 min at 37° C. Post 4-5 h transduction, wells were replenished with RPMI-1640 with 10 and 20% FCS for HEL and JK-1 cells, respectively.

Figure 9:
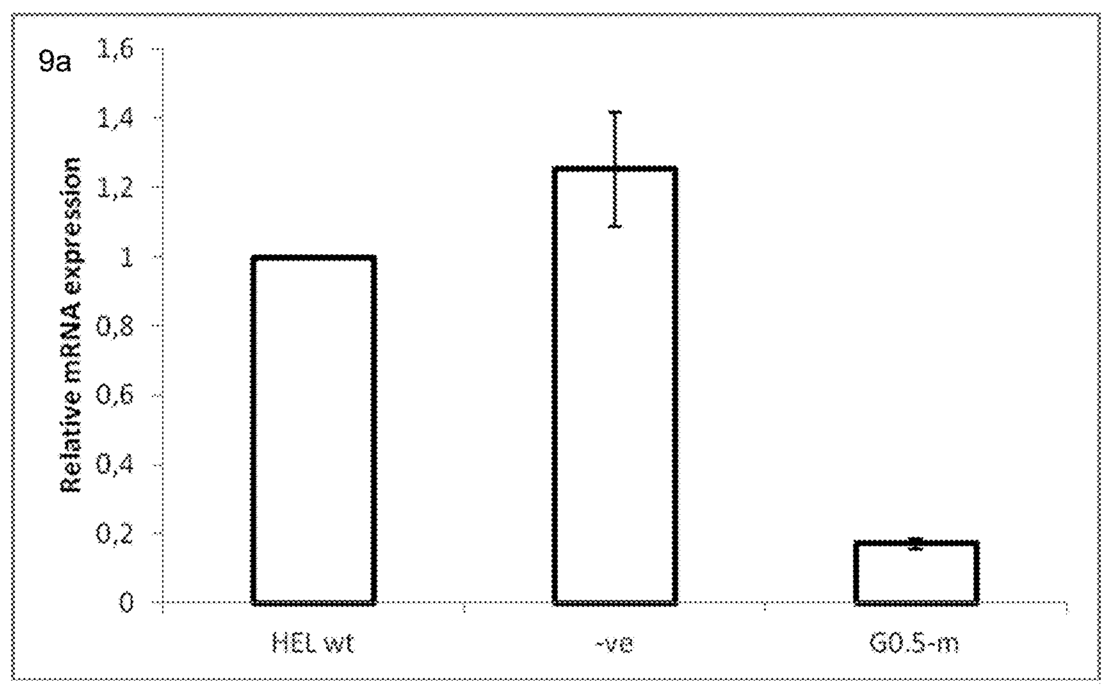
FIG. 9. Results of SMIM1 knockdown in HEL cell line stably expressing SMIM1. 9a shows the relative mRNA expression following transduction of HEL cells with a transduction controls (HEL wt and −ve), and with shRNA clone G at an MOI (multiplicity of infection) of 0.5 U (G0.5-M).
Figure 9:
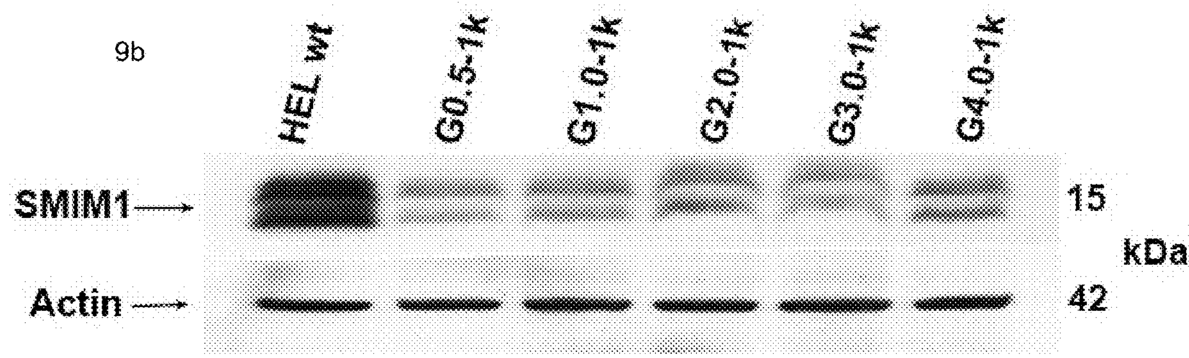

The transduced cells were incubated at 37° C. in a humidified incubator in an atmosphere of 5% $CO_2$ for 48 h. The media containing lentiviral particles was removed and fresh media was added. Puromycin was added at a concentration of 1.75 μg/ml and 0.25 μg/ml for HEL and JK-1 cells, respectively. The media containing drug was replaced after every two days for a period of 8 days. Thereafter, clones were allowed to proliferate till confluent for further analysis. The cell lines were analysed by real time PCR, Western blot and flow cytometry (FIG. 9).

TABLE 2

Primers used in the investigation of SMIM1

| Primer name (SEQ ID NO.) | Sequence 5' to 3' | Purpose | Product size (bp) wt/mut |
|---|---|---|---|
| 388588cDNAf (SEQ ID NO. 11) | CGCACCTCAGCCCACGAC | Amplification & Sequencing | 472/455 |
| 388588cDNAr (SEQ ID NO. 12) | TCCAGGCCTGTGCTCTCAC | | |
| Vel negativeF (SEQ ID NO. 13) | GCCGAATTCGCCACCATGCAGCCCCAGGAGAGC | Cloning & expression | 257/240 |
| Vel negativeR2 (SEQ ID NO. 14) | GCCGGATCCCCCTTATTTGCACTTGTGCACATA | | |
| 388588int2f (SEQ ID NO. 15) | TCTCCTAACAGCAGCCTCAG | Amplification and sequencing | 745/728 |
| 388588ex4r (SEQ ID NO. 16) | TGTCTCCAGGCCTGTGCTC | | |
| 388588int3f (SEQ ID NO. 17) | CAGCTCAGCAAACCGCAGC | Sequencing | |
| 388588int3r (SEQ ID NO. 18) | GGCGCTCTGCTGGAGTCA | | |
| 388588int3r2 (SEQ ID NO. 19) | CTGGGCGCTCTGCTGGAG | Sequencing; ASP | 266 |
| 388588wtex3f (SEQ ID NO. 20) | CGGAGTCAGCCTAGGGGC | ASP screening | |
| 388588mutex3f (SEQ ID NO. 21) | GGACGGAGTCCAGCACAG | | 249 |
| LOCex3f screen (SEQ ID NO. 22) | ACAGCCTGGCCACCTGTCTTG | GSP Screening | 178/161 |
| LOCex3r screen (SEQ ID NO. 23) | CTGCGGCAGCGTGAGGC | | |
| RACE primer Vel 59F (SEQ ID NO. 24) | GGCCGCAGTGGGCAGGCTC | 3' RACE | |
| RACE primer Vel 176F (SEQ ID NO. 25) | CTCAGGCAAGGTTCTCCGGTGA | | |
| RACE primer Vel 280F (SEQ ID NO. 26) | AGGAGAGCCACGTCCACTATAG | | |
| RACE primer Vel 332R (SEQ ID NO. 27) | GCAGCGTGAGGCCTCTTCTGTG | 5' RACE | |
| RACE primer Vel 355R (SEQ ID NO. 28) | CACAGCCTCTGGGAGATCCTGC | | |
| RACE primer Vel 376R (SEQ ID NO. 29) | GATGCCCAGCTTGCCCGTGC | | |

Example 3: Generation of Rabbit Antibodies

Four overlapping peptides were designed from the predicted extracellular domain of SMIM1 (SEQ ID NO. 5) as follows:

```
Peptide 1
                                        (SEQ ID NO. 6)
MQPQESHVHYSRWED

Peptide 2
                                        (SEQ ID NO. 7)
SRWEDGSRDGVSLGA

Peptide 3
                                        (SEQ ID NO. 8)
GVSLGAVSSTEEASR

Peptide 4
                                        (SEQ ID NO. 9)
EASRCRRISQRLCTG

Peptide 5
                                       (SEQ ID NO. 10)
CPESWHSYMRVQHEQD (scrambled peptide 1)
```

Peptides 1 and 3 were used to immunize rabbits to produce a polyclonal antibody to the predicted protein. Peptide synthesis and antibody production was purchased as a service from Innovagen AB (Lund, Sweden). Post-immunization sera were tested by hemagglutination and by Western blotting. Neither antibody was specifically reactive by routine serological hemagglutination techniques (described below) however, anti-peptide 1 was highly specific as indicated in the section describing the Western blotting experiments below.

ELISA

ELISA was performed to determine whether polyclonal anti-Vel specifically recognized the linear peptides 1-4. Peptide 5 was a scrambled sequence of peptide 1. A concentration of 0.01 ug/mL of each peptide was used to coat microplates overnight. Following coating, the plates were blocked in 1% PBS/BSA, washed and incubated with anti-Vel. An unrelated antibody, anti-K and inert plasma (AB serum) were used as controls. Unbound antibody was washed off, and the plate incubated with HRP-labelled goat anti-human IgG (BioRad Laboratories). Following washing, the reaction were developed with TMB Single Solution chromogen for ELISA (Invitrogen) and stopped with 1 M HCl. Reactions were read at 450 nm by an ELISA reader.

SDS-PAGE and Western Blot Analysis of the Rabbit Anti-Peptide 1

Figure 6:
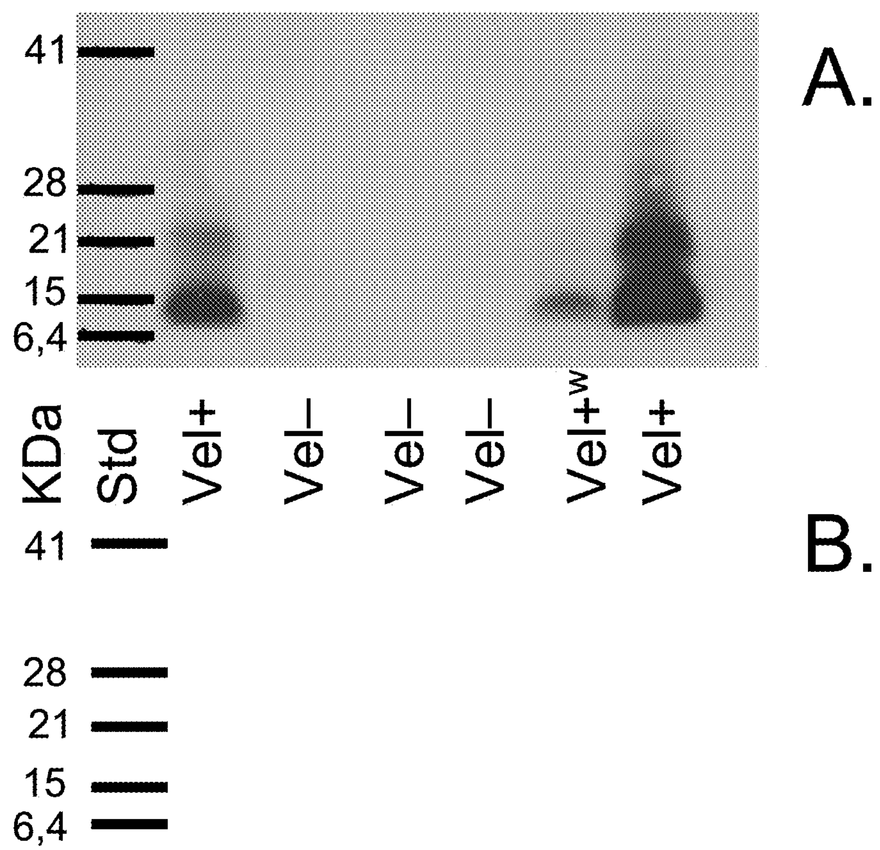
FIG. 6. Panel A is a Western blot showing the highly specific Vel antigen discriminating ability of the rabbit anti-peptide 1 (peptide 1=SEQ ID NO. 6). Panel B shows the same membrane stripped and reprobed with anti-GAPDH as a loading control. Vel positive samples are genotypically wild type homozygotes; Vel negative samples are genotypically mutant homozygotes. The Vel weakly positive ($^{w}$) sample was a genotypically determined wild type/mutant heterozygote which expresses SMIM1 weakly.

Erythrocyte membranes were prepared as described previously: and solubilised with 1% Nonidet P-40. The solubilizate was mixed with equal volumes of Laemmli sample buffer with or without the addition of 5% mercaptoethanol depending on the conditions required. Prior to loading, samples were heated to 95° C. for 5 minutes. Solubilised RBC membranes (15 μL) were run on NuPAGE) 4-12% Bis-Tris gels (Novex, Life Technologies) for ~75 minutes at 150 v until the dye front reached the bottom of the gel. The gel was either stained with SimplyBlue™ SafeStain (Life Technologies), or the proteins were transferred onto polyvinylidene difluoride (PVDF) membranes. The membranes were blocked in 5% non-fat milk/phosphate-buffered saline (PBS) for 1 hour at room temperature, then rinsed in PBS before incubation with anti-peptide 1 (bleed #2, diluted 1:20,000) for 2 hours at room temperature. Following incubation, the membranes were washed 3×10 minutes in PBS/Tween (PBST), then incubated for 1 hour at room temperature with horseradish peroxidise (HRP)-labelled goat anti-rabbit IgG (Agrisera, Vannas, Sweden) diluted 1:10000 in PBS-T. The PVDF membranes were washed as before and then developed with ECL reagent (Life Technologies) according to the manufacturer's instructions. The labelled membranes were sealed in plastic and then exposed to film (Hyperfilm ECL, Life Technologies) for an appropriate time, as determined by an initial 60 second exposure, and developed manually. The membranes were reprobed with a murine anti-GAPDH (clone 6C5, Millipore, Solna, Sweden), diluted 1:5000, washed and incubated with HRP-labelled goat anti-mouse IgG diluted 1:10000 in PBS-T; and visualised as above (FIG. 6). The results show that the antibody generated to the N-terminal sequence of the SMIM1 proteins specifically recognised a protein that was present in Vel positive individuals but absent in Vel negative individuals.

Example 4: Flow Cytometry

Flow cytometry was performed on RBCs, cell lines and transfected cells. A suspension of approximately $0.5\times10^6$ RBCs or $10^6$ cultured cells in PBS containing 1% bovine serum albumin (PBS/BSA) were tested with polyclonal human anti-Vel, diluted 1:4 in PBS/BSA. AB serum was included as a control for unspecific binding. After washing unbound primary antibody, cells were incubated with FITC-conjugated $F(ab')_2$ Fragment Rabbit Anti-Human IgG (Dako, Electra-Box Diagnostica AB, Stockholm) diluted 1:4 (RBCs) or with R-Phycoerythrin (PE)-conjugated AffiniPure $F(ab')_2$ Fragment Goat Anti-Human IgG (Jackson Immunoresearch Europe Ltd, Newmarket, England) diluted 1:40 (cell lines and transfected cells). The cells were washed twice as before and resuspended in 300 μl PBS. Analysis was performed with the FACSCalibur cell cytometer (Becton Dickinson, Calif., USA) using CellQuest™ 3.3 software (Becton Dickinson); 10,000 events were analysed for RBCs and 50,000 events for transfected cells. PE-conjugated anti-CD33 (Dako, Life Technologies) and 7AAD (BD Pharmingen) were used as positive compensation controls in tricolour FACS analysis of transfected K562 cells. Viable cells were gated for double-positive signal in the GFP- and PE-channels and assumed to be Vel positive.

Figure 7:
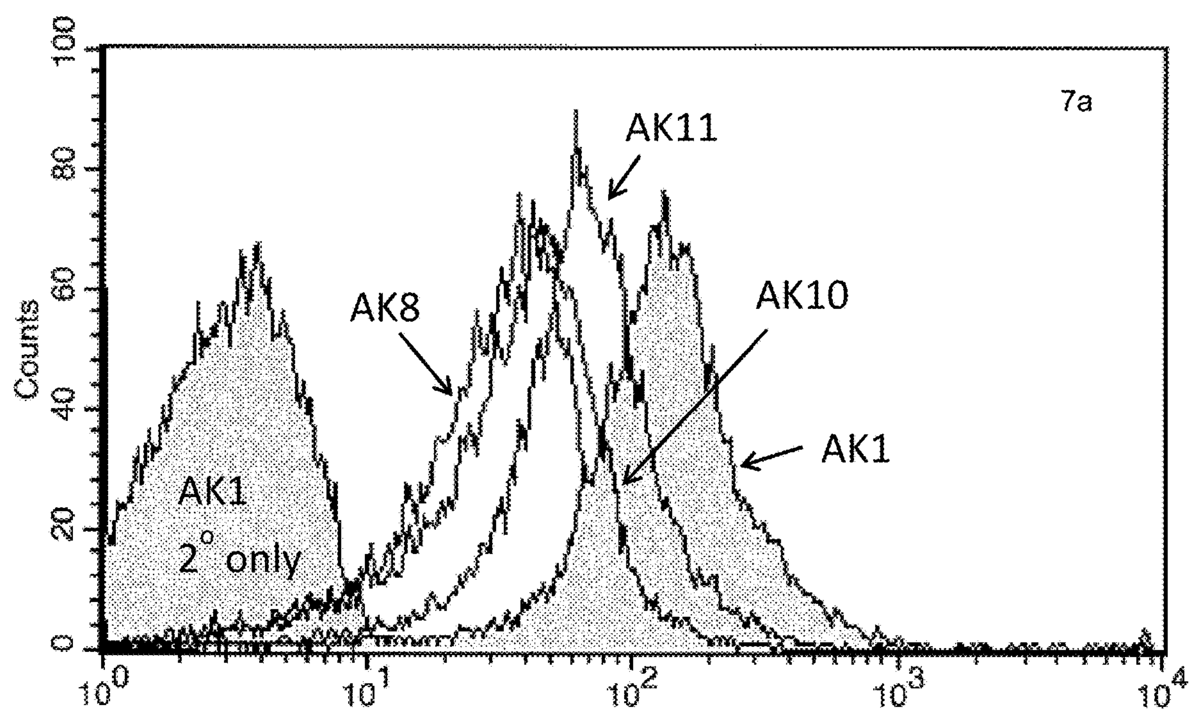
FIG. 7. Flow cytometric analysis of the Vel antigen with human polyclonal anti-Vel. 7*a*: Histogram showing the natural variation in Vel antigen expression on normal RBCs homozygous for wild type SMIM1. The black lines represent different examples of Vel-positive RBCs (labelled AK1, AK8, AK10, AK11) tested with anti-Vel, followed by a FITC-labelled anti-human IgG (2o antibody). The shaded histograms indicate reactivity of AK1 RBCs tested with anti-human IgG only (left), and with anti-Vel (right). 7*b*: Figure to show the influence of SMIM1 zygosity on Vel antigen expression. 7*c*: Over-expression of SMIM1 (referred to as LOC here) in K562 cells demonstrated strong Vel antigen expression compared to the mock transfected (control) and mutant (Vel negative) constructs. The y axis shows the relative number of Vel positive cells, where the percentage of positive cells in the control was set to 1.
Figure 8:
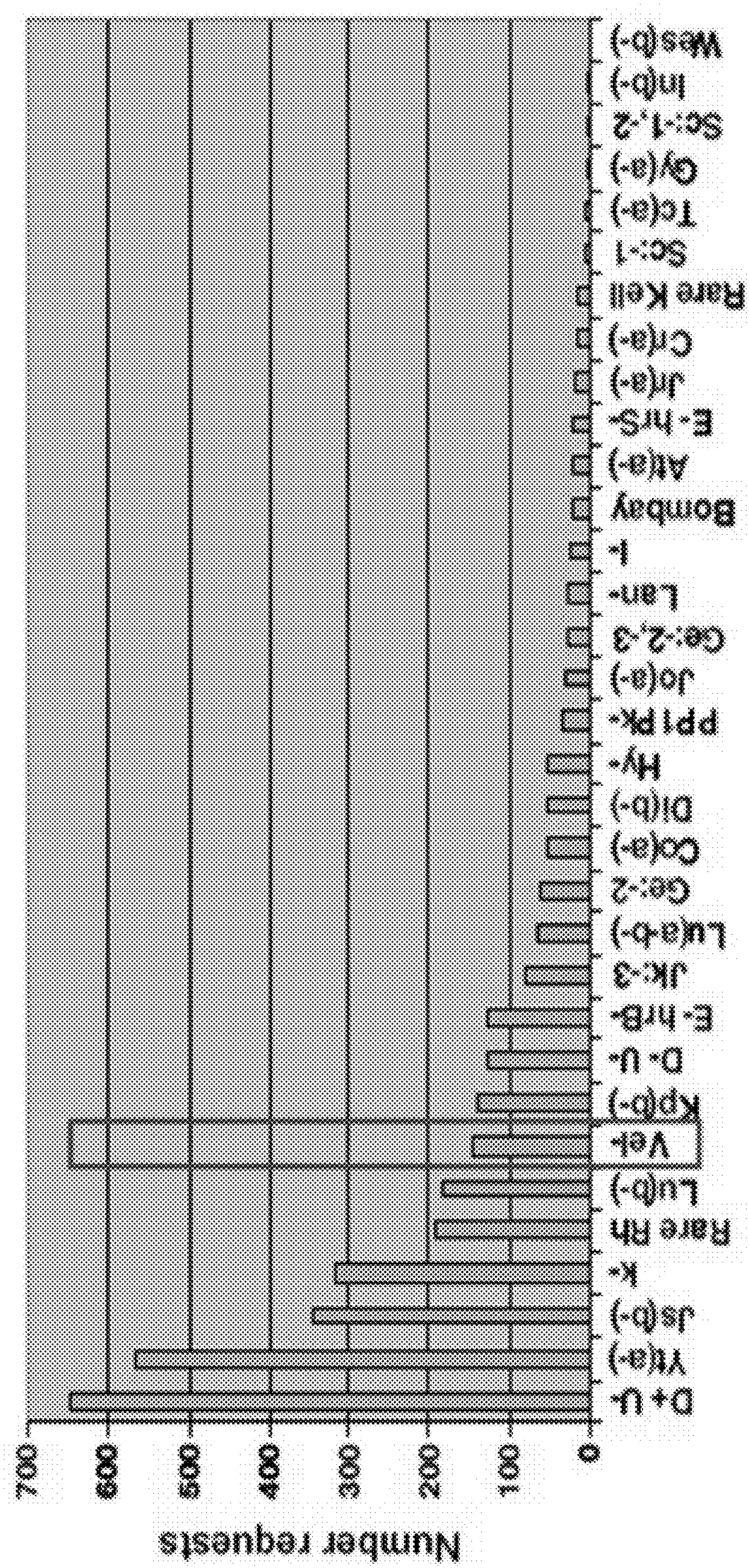
FIG. 8. Overview of requested high-incidence-antigen-negative blood over the period 2005 to 2010 from the American Rare Donor Program. Vel negative blood bar boxed for clarity. Vel negative blood is the most frequently requested blood type negative for an orphan blood group, i.e. where typing, selection and confirmation cannot be done by nucleic-acid-based methods.

Vel antigen expression is well-known in the field to vary between the RBCs of one Vel positive individual and another. FIG. 7*a* shows the variation between RBCs from normal blood donors known to be homozygous for wild type SMIM1. FIG. 7*b* shows the mean antigen expression obtained by flow cytometric analysis from 37 blood donor samples (16 w/m; 21 w/w genotype). FIG. 7*c* shows the Vel antigen expression following over-expression of full-length SMIM1.

Serologic Analysis

Standard agglutination techniques were used for identification of anti-Vel, RBC phenotyping and hemagglutination/inhibition tests. Anti-Vel was affinity-purified by adsorption onto and elution from Vel positive RBCs. Eluates were prepared using the Elu-Kit II kit (Immucor Inc., Norcross, USA).

Example 5: Expression of SMIM1 in K562 Cells

Plasmids

The full cDNA sequence (exons 1-4) of the SMIM1 gene were amplified from Vel positive and Vel negative blood donors and inserted into the green fluorescent protein (GFP)-positive plasmid vector pIRES2-ZsGreen1 by restriction enzyme digestion using EcoR1 and BamH1. Following re-ligation, One Shot® TOP10 chemically competent *E. coli* (Invitrogen) cells were transformed with the new constructs and incubated overnight on agar plates containing Kanamycin. Colonies were PCR-amplified and sequenced to confirm the presence and orientation of the insert. Colonies containing the wild type sequence (pEF1α-LOCwt), the mutant sequence (pEF1α-LOCmut) or empty vector (pEF1α-IRES-ZsGreen1) were cultured overnight in multiple 15 ml tubes containing 5 ml LB medium and 5 μl Kanamycin. Minipreps were prepared using GeneJET Plasmid Miniprep Kit (Thermo Scientific, # K0502). Plasmid DNA concentration and purity measurements were assessed using the Quant-iT™ dsDNA Broad-Range Assay Kit (Invitrogen, Life Technologies), and were re-sequenced to confirm the presence of the correct insert.

Cell Culturing and Transfection

K562 cells were cultured in RPMI 1640 medium (Gibco, Life Technologies) supplemented with 10% fetal bovine serum (FBS; Gibco) at 37° C. and humidified atmosphere containing 5% $CO_2$. Cultured K562 cells were mixed with 10 μg plasmid containing wild type, mutant or control vectors and electroporated using the Gene Pulser II electroporation system (BioRad Inc. Carlsbad, Calif.) and incubated for 48 h before being analysed by flow cytometry.

Example 6: Method for Screening for Vel Negative/Negative Blood (Donors/Recipients)

Assays to discriminate the wild type and mutant alleles have been designed. It is important to note that the primers given in table 2 are not the only primers that can be used for assays 1 and 2, however it is important that the amplicon contains the sequence in which the 17 bp deletion occurs to obtain specificity. Three manual methods are already in use:

1) Gene-specific PCR (GSP): genomic DNA can be amplified with primers LOCex3f_screen (SEQ ID NO. 22) and LOCex3r_screen (SEQ ID NO. 23) which flank SMIM1 exon 3. Allele-specific PCR products of 178 bp (wild type) or 161 bp (mutant) are readily discriminated based on size by electrophoresis for 75 minutes at 165V on a 3% agarose gel (see FIG. 4).
2) PCR-RFLP: genomic DNA can be amplified with primers 388588int2f (SEQ ID NO. 15) and 388588int3R2 (SEQ ID NO. 19).

In this assay, the amplified bands are 459 and 442 bp respectively however, the size of the amplicon is arbitrary and other gene-specific primers surrounding the deletion could be used.

Figure 5:
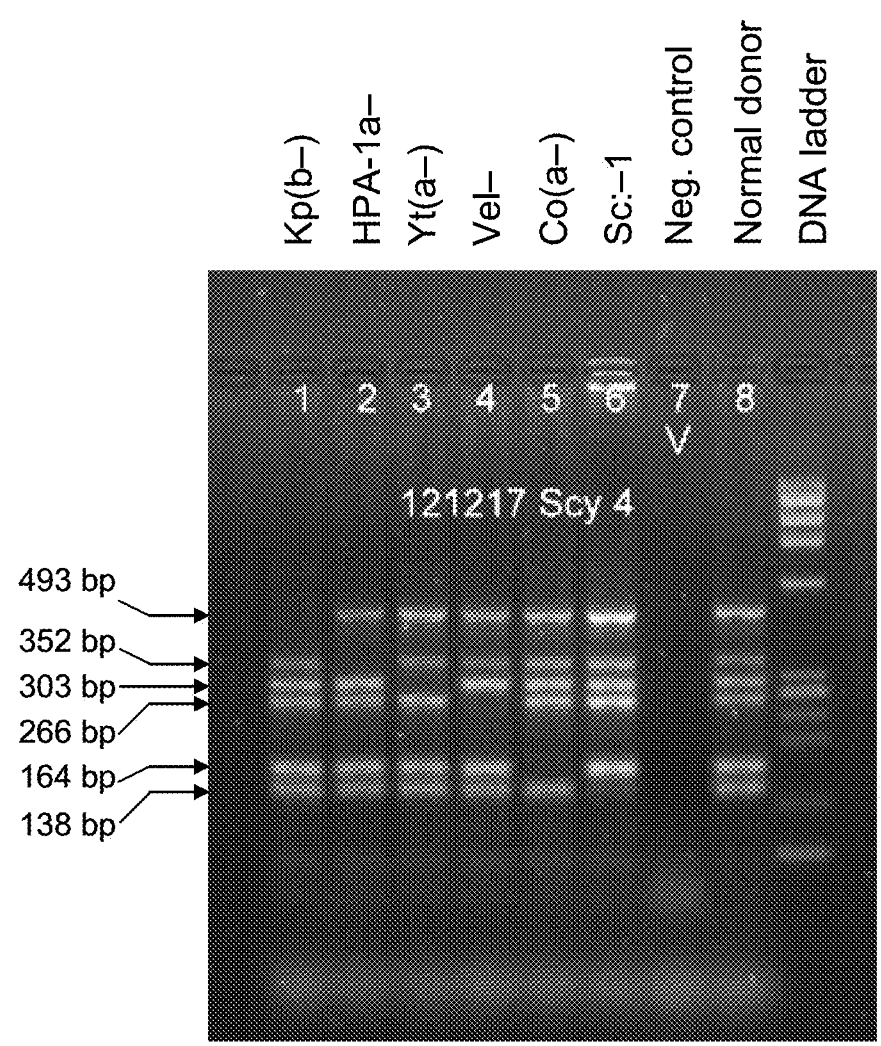
FIG. 5. Medium-throughput screening. An assay to detect six clinically relevant blood group polymorphisms was developed to amplify DNA directly from whole blood. These alleles are differentiated by amplicon size and can be readily identified by gel electrophoresis (shown here) or by fragment analysis using labelled probes (data not shown). Primers that amplify wild type SMIM1 have been incorporated into the assay and DNA from Vel− individuals are not amplified by the SMIM1 primers as indicated in lane 4.

The products were digested with StyI at 37° C. for two hours. Products were analysed on a 3% agarose gel. (see FIG. 2). The restriction site was abolished in the mutated sequence.
3) Allele-specific PCR (ASP): genomic DNA can be amplified with primers 388588int2f (SEQ ID NO. 15) (1 pM), 388588int3R2 (SEQ ID NO. 19) and either 388588wtex3f (SEQ ID NO. 20) or 388588mutex3f (SEQ ID NO. 21). An internal control band was provided by the amplification of a 460 bp (wild type) or 443 bp (mutant) product. Allele-specific bands of 266 bp (wild type) or 249 bp (mutant) were specifically amplified by their respective primers (see FIG. 3). Based on this principle, primers amplifying the 266 bp wild type SMIM1 fragment (388588int3R2 (SEQ ID NO. 19) and 388588wtex3f (SEQ ID NO. 20)) have been incorporated into a medium-thoughput, albeit manual, screening method for high-prevalence blood group alleles (see FIG. 5). Vel− individuals, i.e. homozygous SMIM1 mutants are identified by the absence of the SMIM1-specific band in the presence of the remaining five bands specific for other blood group loci.

Further methods useful include semi-automated (medium- and high-throughput) genotyping-based assays which readily incorporate screening for Vel into their platforms. This is achieved by incorporating a probe that span the deleted sequence such that routine genotyping gives a negative signal in the absence of the wild type sequence. This is the simplest method for detecting Vel negative samples however; software that distinguishes homozygotes from heterozygotes could raise the level of sophistication through the incorporation of a wild-type and normal probe into the technology. Probe sequences that are useful (and which have already demonstrated allele-specificity in example 6, method 3 above) are primer sequences 388588wtex3f (SEQ ID NO. 20) and 388588mutex3f (SEQ ID NO. 21).

Example 7: Integrating the Present Methods into Screening Platforms

BLOODChip (Progenika Biopharma, SA) is a microarray platform that incorporates allele-specific probes (usually based on single nucleotide polymorphisms) that capture labelled PCR products containing the allele of interest. For example, a multiplex PCR reaction amplifies from genomic DNA selected regions of different blood group genes that contain antigen-defining polymorphisms. The PCR products are labelled and annealed to the microarray that is printed with both permutations of an allele. The PCR product will anneal to the probe containing the allele-specific SNP at a specific position. Positive reactions are determined by a laser reader. Probe sequences that could be incorporated into such a platform would include SEQ ID NO. 20 for detection of the Vel wild type allele (i.e. Vel+), and SEQ ID NO. 21 for detection of the Vel mutant allele (i.e. Vel negative). Depending on the requirements of the system, i.e. oligonucleotide primers longer than 18 base pairs, the probes could be elongated at either end with the consensus sequence without affecting specificity.

HEA BeadChip™ Kit (Immucor, Inc.) is a technology which employs beads to which allele-specific oligonucleotide probes are attached to coloured beads. The colour determines the signature of each bead, and post production, they are sorted to a silicon wafer which is the test platform. As above, a multiplex PCR reaction amplifies from genomic DNA selected regions of different blood group genes that contain antigen-defining polymorphisms. These products are mixed with the beads, and in contrast to the above, the technology relies on allele-specific extension of the DNA strand and incorporation of the labelled PCR product Again, the 17-bp deletion in SMIM1 could be exploited by this technology using probes that incorporated SEQ ID NO. 20 or SEQ ID NO. 21 at the site of active synthesis.

MassARRAY® iPLEX® technology (Sequenom® GmbH) have developed a matrix-assisted laser desorption/ionisation time-of-flight mass spectrometry (MALDI-TOF) platform for the detection of specific blood group alleles. This technology bases detection of a specific allele on the mass difference between one allele and its counterpart and has been shown to be very specific [5]. It is a flexible technology that allows rapid incorporation of desirable alleles. Currently, Sequenom® GmbH have a platform in place for the detection of common blood group alleles and are looking to expand into the detection of alleles encoding other clinically significant blood group antigens.

In addition to the three platforms mentioned above, the present invention could be integrated into and make use of any solid or fluid phase matrix for genotyping that relies on the allele-specific annealing, extension or recognition could incorporate probes that include SEQ ID NO. 20 or SEQ ID NO. 21 for the specific determination of the Vel positive and Vel negative phenotype respectively.

Example 8: Case Study I

A 72-year-old woman, blood group B, RhD positive, is scheduled for repair of a carotid artery with little associated risk for bleeding. She had been transfused eight years previously following orthopaedic trauma at another regional hospital although the details were not available. At that time, irregular antibodies had been detected in her plasma and were attributed most likely due to an autoantibody. Due to the low likelihood that the patient would require blood, the surgery is started even though the current serological investigation is not complete and as previously, demonstrated the presence of irregular antibodies to an undetermined antigen. Perioperative bleeding is modest but the patient suffers from a myocardial infarction in day 1 post-surgery and a blood transfusion with one unit of compatible erythrocytes is started. After 50 mL of blood, the patient has a transfusion reaction, with chills and vomiting and the transfusion is stopped. The extended serological investigation demonstrates that the patient has an anti-Vel that was the cause of her transfusion reaction. The known variable expression of Vel antigen on erythrocytes and the relatively weak reactivity of the patient's antibody in vitro contributed to the patient receiving a unit of Vel positive blood. The present case study exemplifies the need for the improved genetic Vel blood group tests provided utilising the methods of the present invention Example 9: Case Study II Two units of RBCs were ordered for a 44-year-old woman with renal failure and cancer. A pre-transfusion antibody screen revealed that her plasma contained an irregular antibody reactive with all test RBCs by a routine indirect antiglobulin test however, the reactivity could be eliminated once the plasma was warmed to 37° C. Based on these results, the laboratory deemed the antibody not to be clinically significant ("cold-reactive antibody"), and the patient was transfused with 2 units of blood. The patient died 8 hours later following a haemolytic transfusion reaction. A post-mortem antibody investigation performed by a Reference laboratory demonstrated that the patient's plasma contained a potent, haemolytic anti-Vel which was the cause of the fatal transfusion reaction [6]. The present case study is a further example of the long felt need for improved Vel blood group tests such as the genetic test provided by the present invention to avoid potentially lethal consequences of the currently unsatisfactory tools and methods available for Vel phenotyping and anti-Vel identification.

REFERENCES

1 Miller S A, Dykes D D, Polesky H F: A simple salting out procedure for extracting DNA from human nucleated cells. Nucleic Acids Research. 1988; 16: 1215.

2 Edvardsson L, Dykes J, Olsson M L, Olofsson T: Clonogenicity, gene expression and phenotype during neutrophil versus erythroid differentiation of cytokine-stimulated CD34+ human marrow cells in vitro. BrJ Haematol. 2004; 127: 451-63.

3 Wester E S, Storry J R, Olsson M L: Characterization of Jk(a+(weak)): a new blood group phenotype associated with an altered JK*01 allele. Transfusion. 2011; 51: 380-92.

4 Judd W J, Johnson S T, Storry J R: *Judd's methods in immunohematology*: aaBB Press, Bethesda, Md., USA; 2008.

5 Gassner C, Meyer S, Frey B M, Volmert C. Matrix-assisted laser desorption/ionisation, time-of-flight mass spectrometry-based blood group genotyping—the alternative approach. Transfus Med Rev. 2013; 27:2-9.

6 Storry J R, Mallory D M: Misidentification of anti-Vel due to inappropriate use of techniques. Immunohematology. 1994; 10: 83-6.

7 Storry J R, Castilho L, Daniels G, Flegel W A, Garratty G, Francis C L, Moulds J M, Moulds J J, Olsson M L, Poole J, Reid M E, Rouger P, van der Schoot E, Scott M, Smart E, Tani Y, Yu L C, Wendel S, Westhoff C, Yalahom V, Zelinski T: International Society of Blood Transfusion Working Party on red cell immunogenetics and blood group terminology: Berlin report. Vox Sang. 2011; 101: 77-82.

The invention claimed is:

1. A method of detecting an anti-Vel antibody in a sample obtained from a subject to determine the blood type of the subject, which comprises:

a) contacting the sample with an antigen consisting of a fragment of at least 5 consecutive amino acid residues and at most 25 consecutive amino acid residues of a polypeptide having at least 87% identity to SEQ ID NO: 5, and b) detecting an antigen/antibody complex, whereby detection of the antigen/antibody complex indicates the presence of the anti-Vel antibody.

2. The method of claim 1, wherein the fragment consists of at least 87% identity to SEQ ID NO: 6, SEQ ID NO: 7, SEQ ID NO: 8, or SEQ ID NO: 9.

3. The method of claim 1, wherein the fragment is SEQ ID NO: 6, SEQ ID NO: 7, SEQ ID NO: 8, or SEQ ID NO: 9.

4. The method of claim 1, wherein the fragment comprises at least 20 consecutive amino acid residues of the polypeptide having at least 87% identity to SEQ ID NO: 5.

5. The method of claim 1, wherein the fragment consists of at least 20 consecutive amino acid residues of the polypeptide having at least 87% identity to SEQ ID NO: 5.

6. The method of claim 1, wherein the fragment comprises at least 15 consecutive amino acid residues of the polypeptide having at least 90% identity to SEQ ID NO: 5.

7. The method of claim 1, wherein the fragment consists of at least 15 consecutive amino acid residues of the polypeptide having at least 90% identity to SEQ ID NO: 5.

8. The method of claim 1, wherein the fragment comprises at least 15 consecutive amino acid residues of the polypeptide having at least 95% identity to SEQ ID NO: 5.

9. The method of claim 1, wherein the fragment consists of at least 15 consecutive amino acid residues of the polypeptide having at least 95% identity to SEQ ID NO: 5.

10. The method of claim 1, wherein the fragment is O-glycosylated.

11. The method of claim 1, wherein the sample is a blood sample.

12. The method of claim 1, wherein said method is performed prior to administering a blood transfusion to the subject.

13. The method of claim 1, wherein the antigen is conjugated to a microchip array.

14. The method of claim 1, wherein the antigen/antibody complex is detected by studying agglutination.

15. The method of claim 1, wherein the antigen/antibody complex is detected by surface plasmon resonance.

16. The method of claim 1, wherein the antigen/antibody complex is detected by ELISA based methods.

* * * * *